(12) United States Patent
Namba et al.

(10) Patent No.: US 8,179,597 B2
(45) Date of Patent: May 15, 2012

(54) BIOLOGICAL SPECIMEN IMAGING METHOD AND BIOLOGICAL SPECIMEN IMAGING APPARATUS

(75) Inventors: Akihiro Namba, Tokyo (JP); Hirobumi Suzuki, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/325,852

(22) Filed: Dec. 1, 2008

(65) Prior Publication Data
US 2009/0086314 A1    Apr. 2, 2009

Related U.S. Application Data

(63) Continuation of application No. PCT/JP2007/061139, filed on May 31, 2007.

(30) Foreign Application Priority Data

May 31, 2006  (JP) ................................. 2006-152676
Mar. 28, 2007 (JP) ................................. 2007-084914

(51) Int. Cl.
*G02B 21/00* (2006.01)
(52) U.S. Cl. ....................................... 359/383
(58) Field of Classification Search ........................ None
See application file for complete search history.

(56) References Cited

U.S. PATENT DOCUMENTS

| | | | | |
|---|---|---|---|---|
| 6,542,293 | B2 * | 4/2003 | Yahiro | 359/383 |
| 7,106,502 | B1 * | 9/2006 | McDowell | 359/368 |
| 7,139,415 | B2 | 11/2006 | Finkbeiner | |
| 2003/0103662 | A1 * | 6/2003 | Finkbeiner | 382/128 |
| 2003/0179445 | A1 * | 9/2003 | Maenle et al. | 359/368 |
| 2004/0051051 | A1 | 3/2004 | Kato et al. | |

FOREIGN PATENT DOCUMENTS

| | | |
|---|---|---|
| EP | 1 351 048 A1 | 10/2003 |
| JP | 10-048512 | 2/1998 |
| JP | 2002-541430 | 12/2002 |
| JP | 2002-542480 | 12/2002 |
| JP | 2004-500576 | 1/2004 |
| JP | 2004-354650 | 12/2004 |

(Continued)

OTHER PUBLICATIONS

Supplementary European Search Report mailed May 11, 2011 in corresponding European Patent Application No. 07744527.8.

*Primary Examiner* — Derek S Chapel
(74) *Attorney, Agent, or Firm* — Scully, Scott, Murphy & Presser, P.C.

(57) ABSTRACT

In a biological specimen imaging method, a biological specimen which is stored in a storing section of a substrate having plural storing sections and emitting a feeble light is imaged through an objective lens. The biological specimen imaging method includes moving any one of the substrate and the objective lens or both until the desired storing section falls within the field of view of the objective lens, measuring any one of a focal position at a near point and the focal position at a far point of the objective lens or both, determining the focal position of the objective lens focused on an observed target region in the biological specimen stored in the desired storing section based on the measured focal position, and adjusting the focal position of the objective lens to the determined focal position so as to image the biological specimen through the objective lens.

6 Claims, 32 Drawing Sheets

FOREIGN PATENT DOCUMENTS

| | | |
|---|---|---|
| JP | 2004-361158 | 12/2004 |
| JP | 2005-118050 | 5/2005 |
| JP | 2005-514589 | 5/2005 |
| JP | 2005-173288 | 6/2005 |
| JP | 2007-167057 | 7/2007 |
| WO | WO 96/01438 A1 | 1/1996 |
| WO | WO 00/63678 | 10/2000 |
| WO | WO 01/71009 A2 | 9/2001 |
| WO | WO 01/71009 A3 | 9/2001 |
| WO | WO 02/48693 A1 | 6/2002 |
| WO | WO 00/46590 | 8/2002 |
| WO | WO 03/067230 A1 | 8/2003 |
| WO | WO 2007/037439 A1 | 4/2007 |

* cited by examiner

FIG.3A
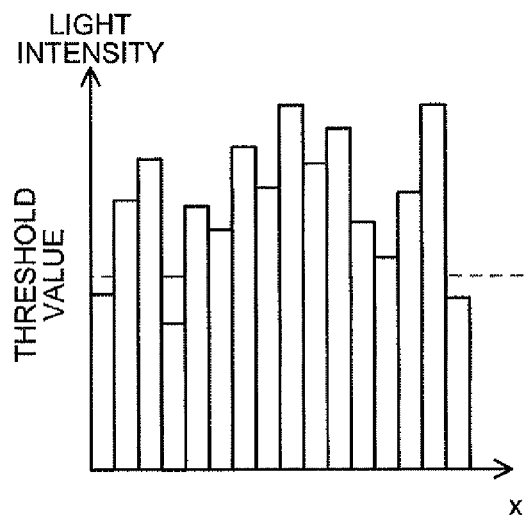
FIG.3B
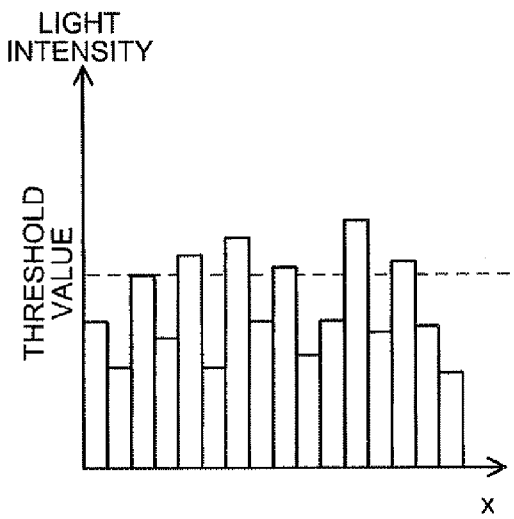
FIG.4
|  | x20 (NA1.36) | x40 (NA1.36) |
|---|---|---|
| FAR POINT SIDE | 10.512 mm | 10.590 mm |
| CENTRAL POINT | 10.507 | 10.506 |
| NEAR POINT SIDE | 10.500 | 10.503 |

ILLUMINATION
IMAGE

LUMINESCENT
IMAGE

ILLUMINATION IMAGE

LUMINESCENT IMAGE

ILLUMINATION
IMAGE

LUMINESCENT
IMAGE

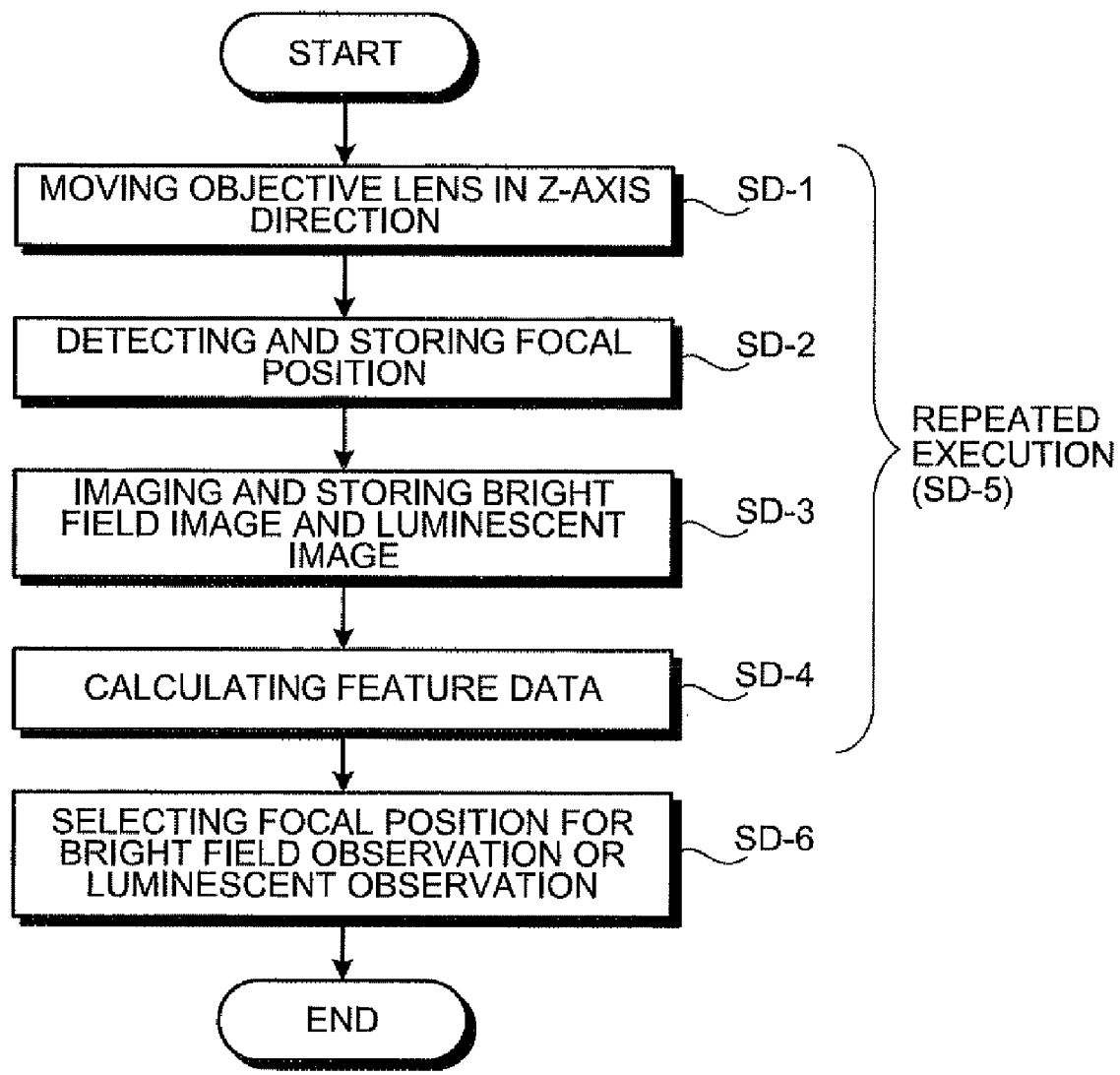

BIOLOGICAL SPECIMEN IMAGING METHOD AND BIOLOGICAL SPECIMEN IMAGING APPARATUS

CROSS-REFERENCE TO RELATED APPLICATIONS

This application is a continuation of PCT international application Ser. No. PCT/JP2007/61139 filed May 31, 2007 which designates the United States, incorporated herein by reference, and which claims the benefit of priority from Japanese Patent Application No. 2006-152676, filed May 31, 2006, Japanese Patent Application No. 2007-084914, filed Mar. 28, 2007, and all incorporated herein by reference.

BACKGROUND OF THE INVENTION

1. Field of the Invention

The present invention relates to a analyzing method and an analyzing apparatus for analyzing an observed target region in a biological specimen, emitting a feeble light, with a suitable resolution. The present invention incorporates herein the content of PCT/JP2006/319589, which is an international patent application filed by the present applicant, by applying the method and the apparatus disclosed in PCT/JP2006/319589 to the present application.

The present invention relates to a biological specimen imaging method and a biological specimen imaging apparatus for imaging an observed target region in a biological specimen that emits a feeble light.

The present invention relates to a method for detecting a biological activity in a biological specimen, such as a cell or a tissue, for a long time or continuously, without deteriorating the activity as much as possible.

The present invention includes software for an automated apparatus executed by the method.

2. Description of the Related Art

[I] In recent years, an imaging technique of a biological sample utilizing fluorescence has taken a great role for a research of a bioscience. A specific protein is marked, and light emission is utilized, whereby various life phenomena happening inside or outside a cell can be observed. Further, dynamic actions of various life phenomena can be known in real time. In recent days, in particular, the use of a fluorescent protein such as GFP (Green Fluorescent Protein) makes it possible to stably and easily realize an imaging of a structure in a cell, so that various life phenomena has been steadily unraveled.

Further, a luminescence-related gene that expresses a bioluminescent protein (specifically, luciferase, aequolin, or the like) has frequently been utilized for various function analyses in a cell (specifically, a luminescence-related gene has frequently been utilized as a reporter molecule of a protein expression). In performing the function analyses described above, it is extremely significant to describe a clear image by bringing a lens into focus on a specific region in a cell, or to efficiently receive light emitted from a specific bioluminescent protein transduced to a cell. However, since an intensity of light of self-luminescence from a biological specimen is generally extremely feebler the luminescence from the biological specimen cannot directly be confirmed with naked eyes in most cases. Even when an optical element (e.g., detection lens, etc.) is adjusted to a specimen emitting a feeble light, it is naturally difficult to bring a lens into focus on the specific region in the specimen with naked eyes.

In view of this, various methods for focusing light on a specimen in a specimen container have been disclosed. However, all of the methods are applicable to the case in which the light from a specimen can be confirmed (visually) with naked eyes. For example, JP-T-2002-541430 and JP-T-2002-542480 disclose a method in which a position of a bottom surface of a specimen container is detected, and light is focused on a specimen in the specimen container based on the detected positional information. In JP-T-2002-541430, light is irradiated to the bottom surface of the specimen container through an objective lens, the intensity of the mirror-reflected light from the bottom surface of the specimen container is sequentially detected while moving the light irradiation position vertically, the position of the bottom surface of the specimen container is detected based on the detected intensity of light, the position of the specimen in the specimen container is estimated based upon the detected positional information, and light is focused on the estimated position. In JP-T-2002-542480, light is diagonally irradiated to the bottom surface of the specimen container from below through an objective lens, a deviation amount of the mirror-reflected light from the bottom surface of the specimen container on an XY plane is detected by a photodetector, the position of the bottom surface of the specimen container on an optical axis is detected based upon the detected deviation amount, the position of the specimen in the specimen container is estimated based upon the detected positional information, and light is focused on the estimated position. Thus, the focal position of the objective lens can be focused on the specimen in the specimen container.

JP-A-2004-354650 and JP-A-2005-173288 disclose a method in which, with the use of a microscope for observing a phase object such as a cell with a bright field, the position of an objective lens is shifted in the forward or rearward direction from the general focusing position to be fixed to thereby obtain an observation image with a high contrast by defocus, in order to observe a cell. With this method, the observation image of the cell, which is the phase object, can be obtained with a high contrast.

[II] In the research of a biological science or a medical science, a technique of detecting a biological activity of a biological specimen such as a cell with a reporter assay has widely been utilized. The use of the reporter assay can make various biological activities, which cannot visually be examined, visible. In a conventional clinical examination, only biological materials (nucleic acid, blood, hormone, protein, etc.), which are to be examined, are isolated from the biological specimen by various isolation methods, and the amount or activity of the isolated biological material is reacted with a reagent. However, in a living body, it is the interaction among varied biological materials that exhibits the true biological activity. When a medical agent is studied or developed, the decisive condition for the agent is that the agent is most effectively acted on a biological activity in a living biological specimen. In the reporter assay targeted for a living biological specimen, it is more required that images of a biological specimen and a biological material to be examined are formed for observing a dynamic change at the inside or outside of the biological specimen over time.

Specifically, in a research field utilizing an observation using luminescence (bioluminescence, chemiluminescence) or fluorescence as a reporter substance, a time-lapse or an image-capture of a moving image is demanded in order to catch a dynamic functional expression of a protein molecule in a specimen. Under the present condition, a dynamic change in an image is observed by imaging a fluorescent specimen as a subject (e.g., a moving image of one protein molecule is observed by utilizing fluorescence). When a fluorescent specimen is imaged, it is difficult to take, over time, a stable image that can be used for a quantitative evaluation, because the amount of light emitted from the fluorescent specimen tends to decrease with the lapse of time due to the continuous irradiation of excited light, but a clear image, i.e., an image having high spatial resolution, can be imaged in a short exposure time. On the other hand, in the observation of a dynamic change over time according to an image of a luminescent specimen, the luminescent specimen is observed with the use of a CCD camera having an image intensifier mounted thereon, because the emission from the luminescent specimen is extremely feeble. In the case of imaging the luminescent specimen, a stable image that can be used for a quantitative evaluation can be taken over time, because there is no need to irradiate excited light.

The emission amount from a luminescent specimen is measured in the observation of a luminescent specimen. For example, in the observation of a cell to which luciferase gene is transduced, the light emission amount from the cell due to the luciferase activity is measured in order to examine the strength of the expression of the luciferase gene (specifically, the expression amount). The light emission amount from a cell according to a luciferase activity is measured as follows. Specifically, a cell lysate in which a cell is lysed and a substrate solution containing luciferin, ATP, magnesium, etc, are reacted, and then, the light emission amount from the cell lysate reacted with the substrate solution is quantified by means of a luminometer using a photomultiplier tube. In other words, the light emission amount is measured after the cell is lysed. Thus, the expression amount of the luciferase gene at a certain point can be measured as an average of the whole cell. The methods for transducing a luminescent gene such as a luciferase gene into a cell as a reporter gene include, for example, a calcium phosphate method, lipofection method, electroporation method, etc. Each method is used according to the purpose or a type of a cell. When the strength of the expression of the luciferase gene is examined, with the light emission amount from the cell according to the luciferase activity defined as an index, in a cell into which the luciferase gene is transduced as a reporter gene, a target DNA fragment is coupled to the upstream side or the downstream side of the luciferase gene that is transduced into the cell so as to examine the influence given by the DNA fragment to the transcription of the luciferase gene, and further, a gene, such as a transcription factor, that is considered to affect the transcription of the luciferase gene transduced to the cell is coupled to an expression vector so as to co-express the gene with the luciferase gene, whereby the influence given by the gene product of the gene to the expression of the luciferase gene can be examined.

In order to catch the amount of the expression of a luminescent gene with the lapse of time, it is necessary to measure a light emission amount from a living cell over time. The light emission amount from a living cell is measured over time as follows. Specifically, a function of a luminometer is provided to an incubator that cultivates a cell, and then, the light emission amount from all of the cultivated cell populations is quantified by the luminometer for every predetermined time. Thus, the expression rhythm with a constant periodicity can be measured, whereby the change in the amount of the expression of the luminescent gene in all the cells can be caught over time. On the other hand, when the expression of a luminescent gene is transient, the amounts of the expression in individual cells greatly vary For example, even in a cloned cultured cell such as HeLa cell, the response to an agent via a receptor on the surface of the cell membrane might vary in the individual cells. Specifically, although the response as the whole cell may not be detected, several cells might make a response. From this, it is important to measure the light emission amount over time from not the whole cell but the individual cell, in case where the expression of the luminescent gene is transient. Because light emission from each cell is significantly feeble, the measurement over time of the light emission amount from an individual living cell by means of a microscope is carried out by exposing the cell with a cooled CCD camera with a temperature level of a liquid nitrogen for a long timer or by using a CCD camera provided with an image intensifier and a photon counting apparatus. Thus, a change over time in an amount of expression of a luminescent gene in an individual living cell can be obtained.

In the description above, the analyzing method and apparatus for the expression of a gene, using a fluorescent protein as a reporter gene is disclosed in JP-T-2004-500576, for example. The analyzing method and apparatus for the expression of a gene with the use of a luminometer according to bioluminescence is disclosed in JP-A-2005-118050, for example.

SUMMARY OF THE INVENTION

One aspect of the present invention is a biological specimen imaging method in which a biological specimen which is stored in a storing section of a substrate having plural storing sections and emitting a feeble light is imaged through an objective lens. The biological specimen imaging method according to one aspect of the present invention includes moving any one of the substrate and the objective lens or both until the desired storing section falls within the field of view of the objective lens, measuring any one of a focal position at a near point and the focal position at a far point of the objective lens or both, determining the focal position of the objective lens focused on an observed target region in the biological specimen stored in the desired storing section based on the measured focal position, and adjusting the focal position of the objective lens to the determined focal position so as to image the biological specimen through the objective lens.

One aspect of the present invention is a biological specimen imaging method in which a biological specimen which is stored in a storing section of a substrate having plural storing sections and emitting a feeble light is imaged through an objective lens. The biological specimen imaging method according to one aspect of the present invention includes a moving step of moving any one of the substrate and objective lens or both until the desired storing section falls within the field of view of the objective lens, a light irradiating step of irradiating light to the biological specimen, a focal position changing step of changing the focal position of the objective lens, a focal position measuring step of measuring the changed focal position at the focal position changing step, a light-irradiated specimen imaging step of imaging the biological specimen to which the light is irradiated at the light irradiating step at the changed focal position at the focal position changing step, a feature data calculating step of calculating feature data which characterizes the imaged image based on the imaged image at the light-irradiated specimen imaging step, an executing step of repeatedly executing the focal position changing step, the focal position measuring step, the light-irradiated specimen imaging step, and the feature data calculating step, a focal position selecting step of selecting at least one focal position from the plural focal positions stored by the repeated execution at the executing step based on the plural feature data pieces stored by the repeated execution, a focal position determining step of determining the focal position of the objective lens focused to the observed target region in the biological specimen stored in the desired storing section based on the focal position selected at the focal position selecting step, a focus adjusting step of adjusting the focal position of the objective lens to the determined focal position at the focal position determining step, and a luminescent image acquiring step of imaging the biological specimen through the objective lens so as to acquire the luminescent image of the biological specimen.

One aspect of the present invention is a biological specimen imaging apparatus that images a biological specimen which is stored in a storing section of a substrate having plural storing sections and emitting a feeble light through an objective lens. The biological specimen imaging apparatus according to one aspect of the present invention includes a mover that moves any one of the substrate and objective lens or both until the desired storing section falls within the field of view of the objective lens, a light irradiator that irradiates light to the biological specimen, a focal position changer that changes the focal position of the objective lens, a focal position measurer that measures the focal position of the objective lens, a specimen imager that images the biological specimen, a feature data calculator that calculates feature data which characterizes the imaged image based on the image imaged by the specimen imager, a controller that controls the focal position changer, the focal position measurer, the specimen imager, and the feature data calculator so as to repeatedly execute the focal position changer, the focal position measurer, the specimen imager, and the feature data calculator, a focal position selector that selects at least one focal position from the plural focal positions stored by the repeated execution by the controller based on the plural feature data pieces stored by the repeated execution, and a focal position determining unit that determines the focal position of the objective lens focused to the observed target region in the biological specimen stored in the desired storing section based on the selected focal position by the focal position selector.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3A is a graph showing a distribution of light intensity of each pixel contained in a specific pixel array of the CCD camera when the cell is imaged at the position α in FIG. 2;

FIG. 3B is a graph showing a distribution of light intensity of each pixel contained in a specific pixel array of the CCD camera when the cell is imaged at the position β in FIG. 2;

FIG. 4 is a table showing the result of the measurement relating to a focal position on an optical axis of an objective lens when two illumination images are imaged and relating to a focal position on the optical axis of the objective lens when a luminescent image is imaged;

FIG. 41 is a flowchart for showing one example of the focal position determining process executed by the focal position determining apparatus that serves as the biological specimen imaging apparatus 1 according to the third embodiment.

DETAILED DESCRIPTION OF THE PREFERRED EMBODIMENTS

Figure 1:
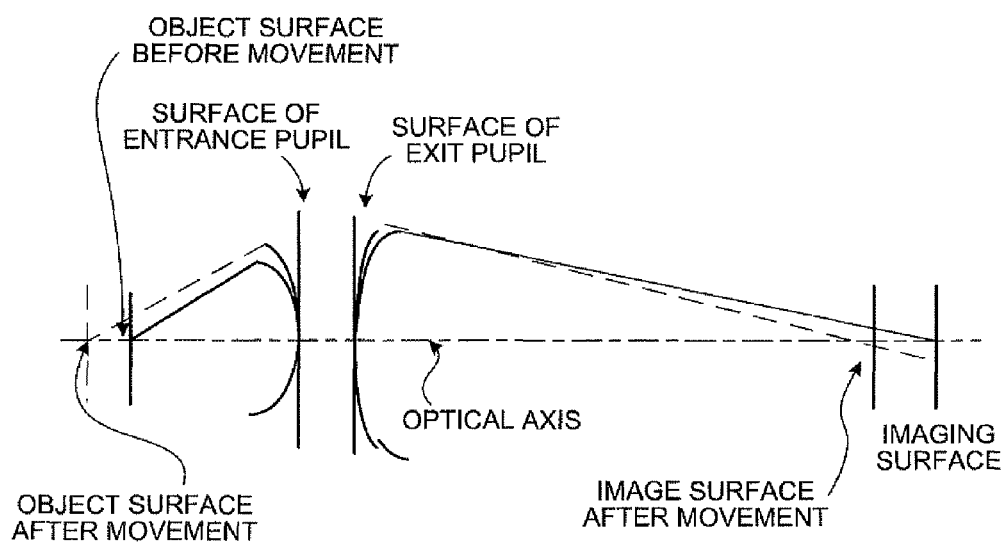
FIG. 1 is a view schematically showing an object point, and an entrance pupil, an exit pupil, and an imaging surface of an optical system.

[I] Embodiments (first embodiment, second embodiment and third embodiment) of a method and an apparatus of analyzing a feeble light image, a biological specimen imaging method and a biological specimen imaging apparatus will be explained below in detail with reference to the drawings. The present invention is not limited to these embodiments.

First Embodiment

1. Basic Principle of Present Invention

Firstly, a basic principle of the present invention will be explained in detail with reference to the drawings. The present invention determines a focal position of an objective lens, which is a reference, measures any one of the focal position (substantial focal position) at the near point of the objective lens and the focal position (substantial focal position) at the far point of the objective lens or both with the determined focal position defined as a reference, determines the focal position of the objective lens focused on an observed target region in a specimen based on the measured focal position, and adjusts (moves) the focal position of the objective lens to the determined focal position.

Specifically, the present invention executes: (1) irradiating light to the specimen; (2) any one of moving, for example, any one of the position of the specimen and the position of the objective lens or both in the optical axis direction, and changing the focal distance of the objective lens (in this case, a variable focus lens is employed) or both, so as to change the focal position of the objective lens by a fixed amount, for example; (3) measuring the changed focal position; (4) imaging the specimen, to which the light is irradiated, by using a CCD (Charge Coupled Device) camera at the changed focal position; (5) calculating feature data (e.g., contrast of the imaged image, integral value of the brightness of the imaged image, statistic amount obtained from the brightness distribution of the imaged image, ratio of the pixel number having the brightness exceeding a predetermined threshold value and a total pixel number of the imaged image, etc.) that characterize the imaged image based on the imaged image; (6) repeating the processes at (2) to (5); (7) selecting at least one focal position (specifically, any one of the focal position at the near point of the objective lens and the focal position at the far point of the objective lens or both) from the plural focal positions (coordinate values on the optical axis representing the focal positions of the objective lens) accumulated by the execution based on plural feature data accumulated by the execution; (8) determining the focal position of the objective lens focused on the observed target region in the specimen based on the selected focal position; and (9) any one of moving any one of the position of the specimen and the position of the objective lens or both, for example, in the optical axis direction, and changing the focal distance of the objective lens (in this case, the variable focus lens is employed) or both, so as to adjust (move) the focal position of the objective lens to the determined focal position.

In the above-described (7), the present invention may select two focal positions (specifically, the focal position (substantial focal position) at the near point of the objective lens and the focal position (substantial focal position) at the far point of the objective lens) from the plural focal positions accumulated by the execution based on the plural feature data accumulated by the execution, and in the above-described (8), the present invention may determine the central position (substantial central position) between the two focal positions as the focal position of the objective lens that is focused on the observed target region in the specimen, based on the selected two focal positions.

In the above-described (7), the present invention may select one focal position (specifically, the focal position (substantial focal position) at the near point of the objective lens or the focal position (substantial focal position) at the far point of the objective lens) from the plural focal positions accumulated by the execution based on the plural feature data accumulated by the execution, and in the above-described (8), the present invention may determine the position apart from the selected focal position by a predetermined distance as the focal position of the objective lens that is focused on the observed target region in the specimen, based on the selected one focal position and the predetermined distance.

The present invention may further execute: (10) imaging the luminescent image of the specimen by using the CCD camera at the focal position determined at (8); (11) calculating the feature data based on the imaged image; (12) changing the focal position determined at (8); (13) imaging the luminescent image of the specimen by using the CCD camera at the changed focal position; (14) calculating the feature data based on the imaged image; (15) comparing the feature data calculated at (11) and the feature data calculated at (14); (16) when the feature data calculated at (14) is greater as a result of the comparison, determining again the focal position changed at (12) as the focal position of the objective lens focused on the observed target region in the specimen.

In the present invention, an aperture may be arranged as decentered for example relative to the optical axis at the pupil position of an illumination optical system including the light source used at (1). Further, a narrow band-pass filter may be arranged at the illumination optical system including the light source used at (1). The present invention may use a light source emitting monochromatic visible light as the light source used in (1). The present invention may use a living cell or tissue as the specimen.

Taking the case in which a living cell is used as the specimen as one example, the principle of generating a contrast, proportional to the phase distribution of the living cell, to the imaged image (image obtained by illumination light) will be explained with reference to FIG. 1. FIG. 1 is a view schematically showing an object point, and an entrance pupil, an exit pupil, and an imaging surface of an optical system.

When a living cell (object) is arranged at a focusing position, and then, light is irradiated to the object, the light emitted from the object spreads spherically as indicated by a solid line to be incident on the entrance pupil. The light incident on the entrance pupil is emitted from the exit pupil, and the light emitted from the exit pupil becomes spherical converged light to be converged on the imaging surface as indicated by the solid line, whereby the image of the object is finally formed. During the process for forming the image, the difference in the optical paths (phase difference) of rays passing through the optical system is not produced, so that blur does not appear on the image. When the object point is then moved to the position indicated by a dotted line and light is irradiated to the object as shown in FIG. 1, the light emitted from the object spherically spreads to be incident on the entrance pupil as indicated by the dotted line. The light incident on the entrance pupil is emitted from the exit pupil, and the light emitted from the exit pupil becomes spherical converged light to be converted on the imaging surface after the movement as indicated by the dotted line, whereby the image of the object is finally formed. From the above, if the object is observed with the position of the imaging surface after the movement defined as an observation point, a difference in optical paths (phase difference) of the rays passing through the optical system is not produced, while if the object is observed with the position of the imaging surface at the beginning defined as the observation point, the difference in optical paths (phase difference) of the rays is produced.

A living cell can generally optically be treated as a phase object. A living cell has generally the similar shape. Therefore, when illumination light is incident on a cultured living cell distributed on a petri dish, the irradiation light is diffracted in the specific direction dependent on the shape of the living cell since the living cell functions as a diffraction grating, so that the diffraction light can be observed. Specifically, when illumination light is incident on the cell in the petri dish from the specific direction, the diffraction is caused on the incident light depending upon the cell. Therefore, zero-order diffraction light (transmitted light) is generated in the direction of the incident light, and further, first-order diffraction light is generated to the transmitted light in the direction of specific angle.

From the above, the living cell is arranged at the position deviated from the focusing position of the optical system, so as to be capable of producing the phase difference in the rays passing through the optical system. The living cell is observed at the position deviated in the front or to the rear from the focusing position of the observation optical system, whereby the phase difference according to the deviation amount (defocus amount) from the focusing position can be produced between the light transmitted through the living cell and the light diffracted in the living cell. Specifically, the objective lens is moved along the optical axis so as to be focused on the position where the focal position of the objective lens is defined as the focusing position in the ordinary observation, and the objective lens is moved from the moved position by a slight amount, whereby the phase difference proportional to the moving amount can be produced between the rays passing through the observation optical system. This phase difference becomes the greatest in the ray passing through the maximum NA of the objective lens. In this case, some diffraction lights are diffracted to the outside of the NA of the objective lens due to the oblique illumination, and hence, do not transmit through the observation optical system, resulting in that an image having a contrast and a relief-like texture can be formed, like the case of the refraction light.

Specifically, by utilizing the phenomena described above, a clear image of a living cell obtained by illumination light (illumination image) can be obtained, so that the observation same as that by a phase contrast microscope or a differential interference microscope can be carried out. As a result, the produced amount of the phase difference achieves the function equal to the function of a phase film used in the phase contrast observation method, whereby contrast proportional to the phase distribution of the living cell can be provided to the observation image. Consequently, a living cell that is colorless and transparent can be observed with a high contrast.

When a magnification of the observation optical system is reduced in a case where a living cell is observed with a higher contrast, an angle of diffraction light passing through the observation optical system is limited. Therefore, the contrast of the observation image can be increased.

When a phase object such as a living cell is observed, the contrast proportional to the phase distribution of the phase object is proportional to the phase amount of the phase object and the phase difference amount given between the transmitted light and the diffraction light. Further, the angle between the transmitted light and the diffraction light changes depending upon the shape of the phase object. When the angle between the transmitted light and the diffraction light changes, the phase difference amount produced between two beams differs, even if the defocus amounts are the same. In view of this, the aperture is arranged as decentered relative to the optical axis of the illumination optical system at the pupil position of the illumination optical system of the microscope, whereby illumination light that irradiates the object at a specific angle can be generated. Since the diffraction light that is more angled than the transmitted light, transmitting in the direction of the incident light to the object, by the degree of the decentering of the aperture can be incident on the entrance pupil of the optical system, the phase difference between the transmitted light and the diffraction light can be more increased. In other words, the aperture is arranged as decentered from the optical axis of the illumination optical system, whereby the diffraction light can be more angled than the transmitted light. Therefore, the phase difference between the transmitted light and the diffraction light can be more increased (see JP-A-2004-354650). Specifically, the contrast of the observation image can be more increased by increasing the phase difference between the transmitted light and the diffraction light according to these methods.

The sign of the phase difference between the beams generated by the defocus is different between the case in which the object is shifted toward the near point from the focusing position of the observation optical system and the case in which the object is shifted toward the far point. Therefore, the image of the object having a high contrast can be obtained at two positions on the optical axis by the defocus. The contrast of the image that is obtained by shifting the phase object such as a cultured cell toward the near point from the focusing position of the observation optical system to be observed and the contrast of the image that is obtained by shifting the phase object toward the far point to be observed are reversed to each other corresponding to the phase distribution of the phase object. Since the object absorbing light from dusts or the like adhered on the bottom surface of the petri dish is no more a phase object, the contrast of the image is not changed even if the phase difference is generated to the object by the defocus. Accordingly, a phase object can clearly be distinguished from an object that is not a phase object by the defocus. An inter-image operation is performed to the image obtained by shifting the object toward the near point and the image obtained by shifting the object toward the far point, whereby the image components that are not affected by the phase difference provided by the defocus can be separated. In particular by performing the subtraction between the pixels of two images, the contrast of the image component corresponding to the phase distribution of the object can be doubled. Therefore, the image components having no phase information such as dusts, foreign matters, illumination unevenness, etc. can be eliminated. Specifically, this method can more enhance the contrast of the observation image.

Figure 2:
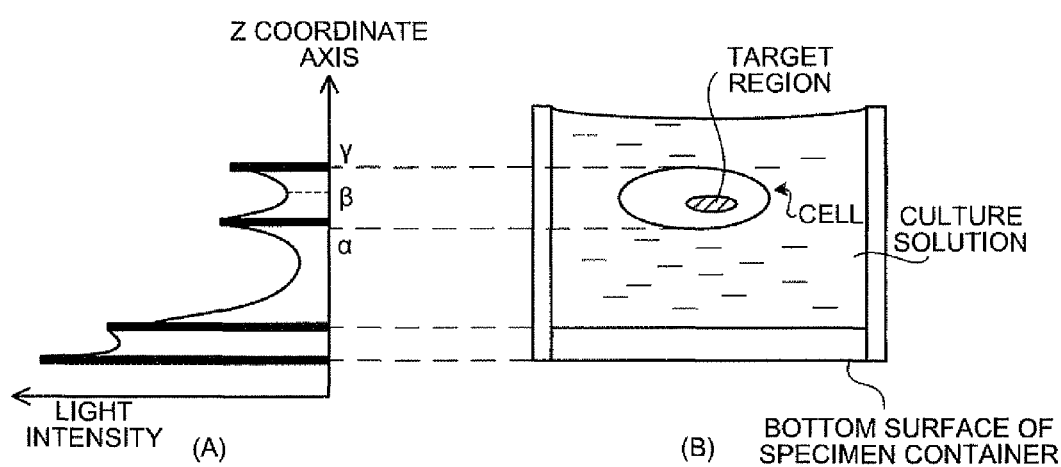
FIG. 2 is a view showing one example of a manner of change of an output signal from each pixel of a CCD camera when a cell is imaged by the CCD camera while moving an objective lens, and schematically showing a position of a petri dish and a position of the cell corresponding to the manner of the change.

Next explained with reference to FIGS. 2, 3A, and 3B are one example of a manner of the change in an output signal (a digital signal corresponding to the light intensity of light caught by each pixel) from each pixel of a CCD camera when a living cell is imaged by the CCD camera while moving the objective lens, and one example of a manner of determining the focal position of the objective lens focused on a specific region (an observed target region) in the living cell based upon the manner of the change in the output signal. When illumination light is irradiated to a living cell, which is immersed in culture solution put in the specimen container (petri dish), and the living cell is imaged by the CCD camera while moving the objective lens from the lower part to the upper part of the petri dish along the optical axis (z axis), the relationship between the integrated values of the output signals (light intensity, light detecting signal) from all pixels of the CCD camera and the focal position (coordinate on the z axis) of the objective lens shown in FIG. 2(A) is established. FIG. 2(B) is a view showing the schematic illustration of the position of the petri dish and the position of the living cell corresponding to FIG. 2(A).

Specifically, when the objective lens is moved upward along the optical axis, the integrated value of the light intensity from all pixels of the CCD camera becomes the maximum and the greatest at the position of the outer bottom surface of the specimen container where the illumination light is strongly reflected. When the objective lens is further moved upward along the optical axis, the integrated value of the light intensity from all pixels of the CCD camera gradually reduces, and then, again becomes the maximum at the position of the inner bottom surface of the specimen container. Since the difference in a refractive index of the inner bottom surface of the specimen container and the refractive index of the culture solution that comes in contact with the inner bottom surface is smaller than the difference in the refractive index of the outer bottom surface of the specimen container and the refractive index of the contact surface of air, the integrated value at the position of the inner bottom surface of the specimen container is smaller than the integrated value at the position of the outer bottom surface of the specimen container. When the objective lens is further moved upward along the optical axis, the integrated value of the light intensity from all pixels of the CCD camera sharply reduces, and then, becomes the maximum again at the position $\alpha$ shown in FIG. 2(A). This position $\alpha$ is the position on the z axis where the imaged image having a high contrast due to the defocus can be obtained. At the position $\alpha$, the objective lens is focused on the portion (lower peripheral edge portion) at the substantial lower edge of the living cell. When the objective lens is further moved upward along the optical axis, the integrated value of the light intensity from all pixels of the CCD camera reduces, and becomes the minimum at the position $\beta$ shown in FIG. 2(A). At this position $\beta$, the objective lens is focused on the approximate central position of the living cell. When the objective lens is further upward along the optical axis, the integrated value of the light intensity from all pixels of the CCD camera increases, and again becomes the maximum at the position $\gamma$ shown in FIG. 2(A). This position $\gamma$ is also the position on the z axis where the imaged image having a high contrast due to the defocus can be obtained. At the position $\gamma$, the objective lens is focused on the portion (upper peripheral edge portion) at the substantial upper edge of the living cell.

Specifically, within the region (including the position $\beta$) from the position $\alpha$ to the position $\gamma$ in FIG. 2(A), the objective lens is focused on the inside of the living cell, whereby the focal position of the objective lens focused on the specific region in the living cell can be determined based on the position $\alpha$ and the position $\gamma$. The position $\beta$ may be determined as the focal position of the objective lens focused on the predetermined region in the living cell.

The output signals exceeding a predetermined threshold value are selected as effective output signals from the output signal (digital signal corresponding to the intensity of the light caught by each pixel) from each pixel of the CCD camera when the living cell is imaged at the position $\alpha$ in FIG. 2(A) and the output signal from each pixel of the CCD camera when the living cell is imaged at the position $\beta$ in FIG. 2(A), and the intensity distribution of the selected each output signal is obtained (see FIGS. 3A and 3B). FIG. 3A is a view showing the distribution of the light intensity of each pixel contained in the specific pixel array of the CCD camera when the living cell is imaged at the position $\alpha$ in FIG. 2(A), and FIG. 3B is a view showing the distribution of the light intensity (the light intensity of the output signal at about the center of the inside of the cell) of each pixel contained in the specific pixel array of the CCD camera when the living cell is imaged at the position $\beta$ in FIG. 2(A). In FIGS. 3A and 3B, a dotted line indicates a threshold value. The intensity distribution shown in FIGS. 3A and 3B is statistically processed, whereby the focal position of the objective lens by which an image having a high contrast can be obtained can be determined. The number of the pixels of the light intensity exceeding a threshold value, which is greater than the threshold value shown in FIGS. 3A and 3B, may be calculated, and the ratio (calculated pixel number÷total pixel number) of the calculated number of pixels to the total pixel number may be calculated, with the focal position of the objective lens being moved along the optical axis, wherein the focal position of the objective lens where this ratio is the highest may be determined as the focal position of the objective lens by which an image having a highest contrast can be obtained.

Subsequently, to what degree the focal position of the objective lens, which is determined based on the focal positions of the objective lens when two images (illumination images) having a high contrast are imaged, is focused on the central region (e.g., the luminescent region) in the living cell, is confirmed by actually imaging the luminescent image of the cell. The living cell used here is a HeLa cell to which a luciferase gene (pGL3-control vector: (by Promega) is transduced with a luciferin in an amount of 1 mM added thereto. The luminescent image is obtained by imaging the HeLa cell after it is exposed for one minute at room temperature.

Figure 5:
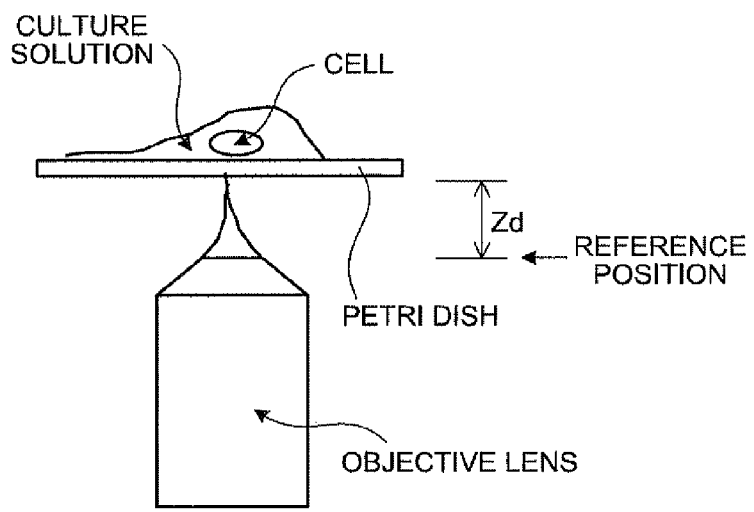
FIG. 5 is a view schematically showing the focal position of the objective lens when the objective lens is focused on the position of the outer bottom surface of the petri dish.

Firstly, as the objective lens is moved along the optical axis, the HeLa cell is imaged as irradiated with the illumination light source, in order to select the imaged image (illumination image) taken at the far point of the objective lens and having the highest contrast and the imaged image (illumination image) taken at the near point of the objective lens and having the highest contrast. On the other hand, the HeLa cell is imaged without being irradiated while moving the objective lens along the optical axis in order to select the imaged image (luminescent image) having the highest contrast. Then, the focal position of the objective lens (×20, ×40) on the optical axis when the selected two illumination images are imaged and the focal position of the objective lens (×20, ×40) on the optical axis when the selected luminescent image is imaged are measured. The result of the measurement is shown in FIG. 4. As shown in FIG. 5, the measured focal position is the same as the distance from the position (reference position) of the objective lens on the optical axis when the objective lens is focused on the position of the outer bottom surface of the specimen container (petri dish).

Figure 6A:
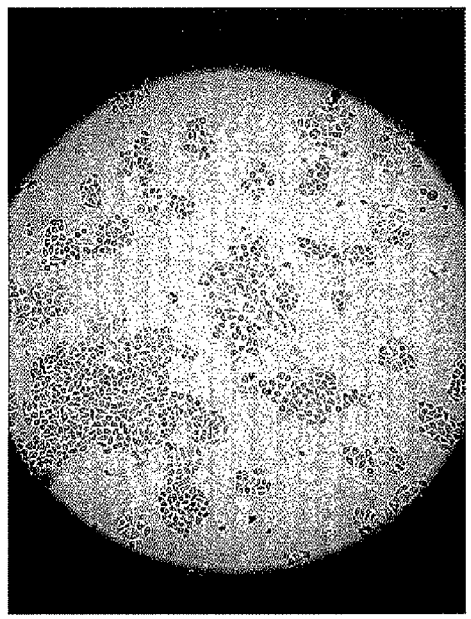
FIG. 6A is a view showing an illumination image having the highest contrast imaged at the near point.
Figure 6B:
FIG. 6B is a view showing a luminescent image having the highest contrast imaged at the near point.
Figure 7:
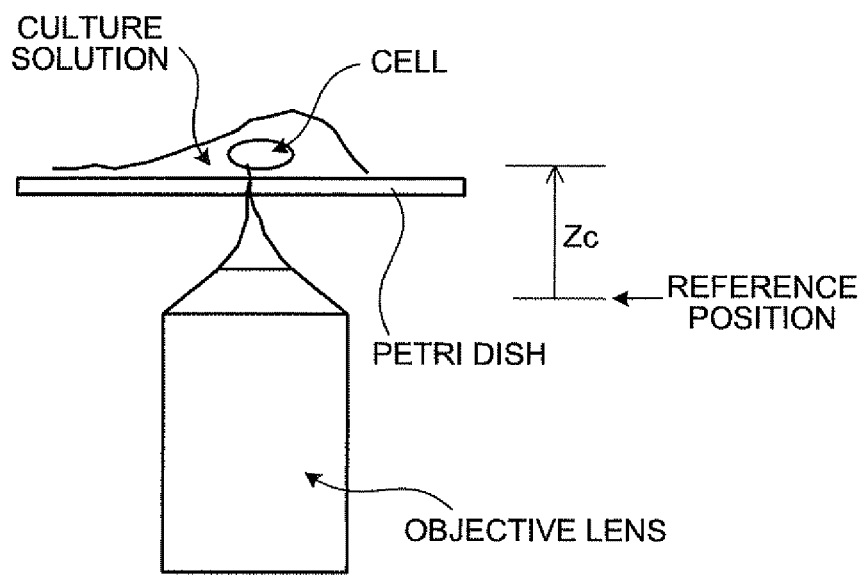
FIG. 7 is a view schematically showing the focal position of the objective lens when the images in FIG. 6A and FIG. 6B are imaged.
Figure 8A:
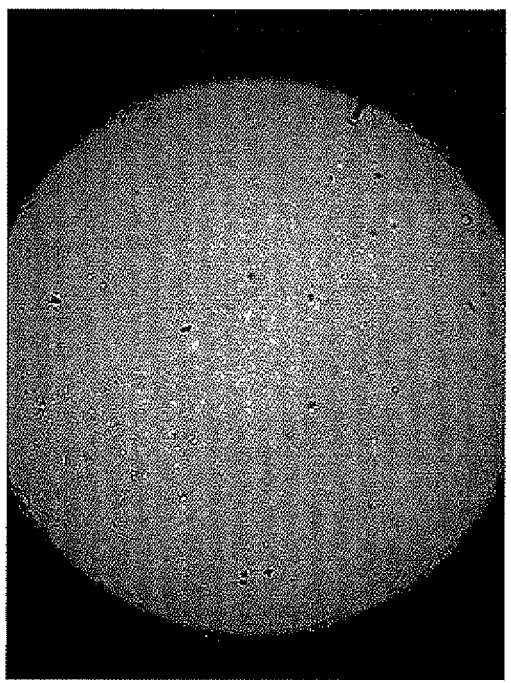
FIG. 8A is a view showing an illumination image having the highest contrast imaged at the central point.
Figure 8B:
FIG. 8B is a view showing a luminescent image having the highest contrast imaged at the central point.
Figure 9:
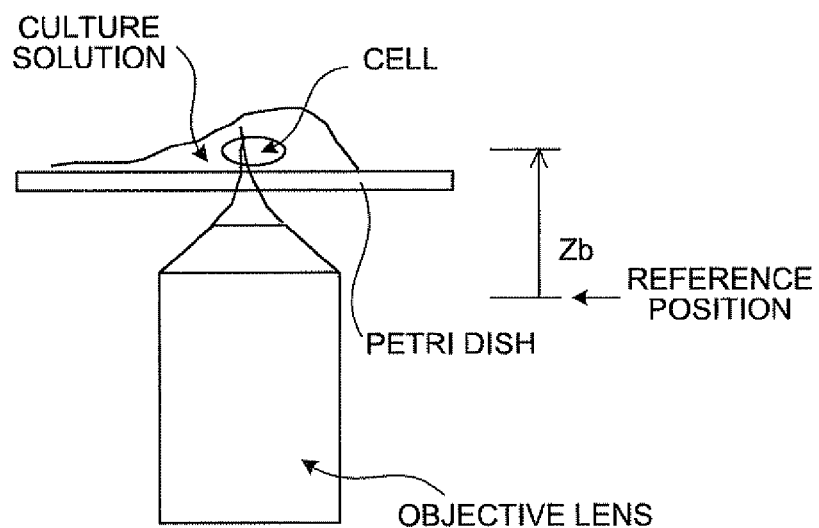
FIG. 9 is a view schematically showing the focal position of the objective lens when the images in FIG. 8A and FIG. 8B are imaged.
Figure 10A:
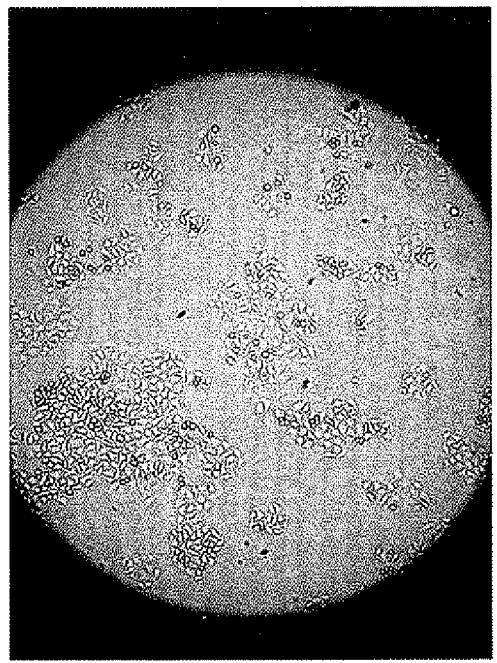
FIG. 10A is a view showing an illumination image having the highest contrast imaged at the far point.
Figure 10B:
FIG. 10B is a view showing a luminescent image having the highest contrast imaged at the far point.
Figure 11:
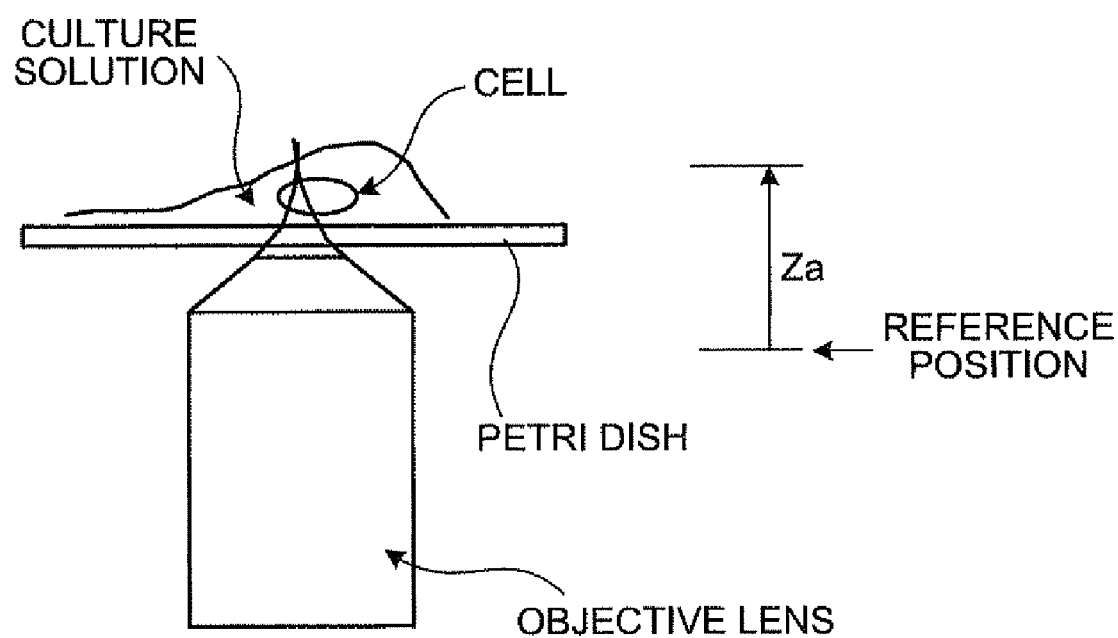
FIG. 11 is a view schematically showing the focal position of the objective lens when the images in FIG. 10A and FIG. 10B are imaged.

As shown in FIG. 4, the focal position (10.507, 10.506 described in the column of "central point" in FIG. 4; "Zb" illustrated in FIG. 9) of the objective lens when the selected luminescent image (FIG. 8B) is imaged is approximately the center of the focal position (10.512, 10.590 described in the column of "far point side" in FIG. 4; "Za" illustrated in FIG. 11) of the objective lens when the illumination image (FIG. 10A) corresponding to the far point is imaged and the focal position (10.500, 10.503 described in the column of "near point side" in FIG. 4; "Zc" illustrated in FIG. 7) of the objective lens when the illumination image (FIG. 6A) corresponding to the near point. Thus, it can be confirmed that the focal position of the objective lens determined based on the focal positions of the objective lens ("Zc" illustrated in FIG. 7 and "Za" illustrated in FIG. 11) when the selected two illumination images (FIG. 6A and FIG. 10A) are imaged is focused on the approximate central region (e.g., luminescent region) in the cell. Specifically, according to the above-mentioned calculation, the objective lens is focused on the approximate central region (e.g., luminescent region) in the cell. FIG. 6A is a view showing the illumination image having the highest contrast and imaged at the near point and FIG. 6B is a view showing the luminescent image having the highest contrast and imaged at the near point. FIG. 7 is a view schematically showing the focal position of the objective lens when the image shown in FIGS. 6A and 6B is imaged. FIG. 8A is a view showing the illumination image having the highest contrast and imaged at the central point and FIG. 8B is a view showing the luminescent image having the highest contrast and imaged at the central point. FIG. 9 is a view schematically showing the focal position of the objective lens when the image shown in FIGS. 8A and 8B is imaged. FIG. 10A is a view showing the illumination image having the highest contrast and imaged at the far point and FIG. 10B is a view showing the luminescent image having the highest contrast and imaged at the far point. FIG. 11 is a view schematically showing the focal position of the objective lens when the image shown in FIGS. 10A and 10B is imaged.

The explanation of the basic principle of the present invention is ended here.

2. Structure of Apparatus

Figure 12:
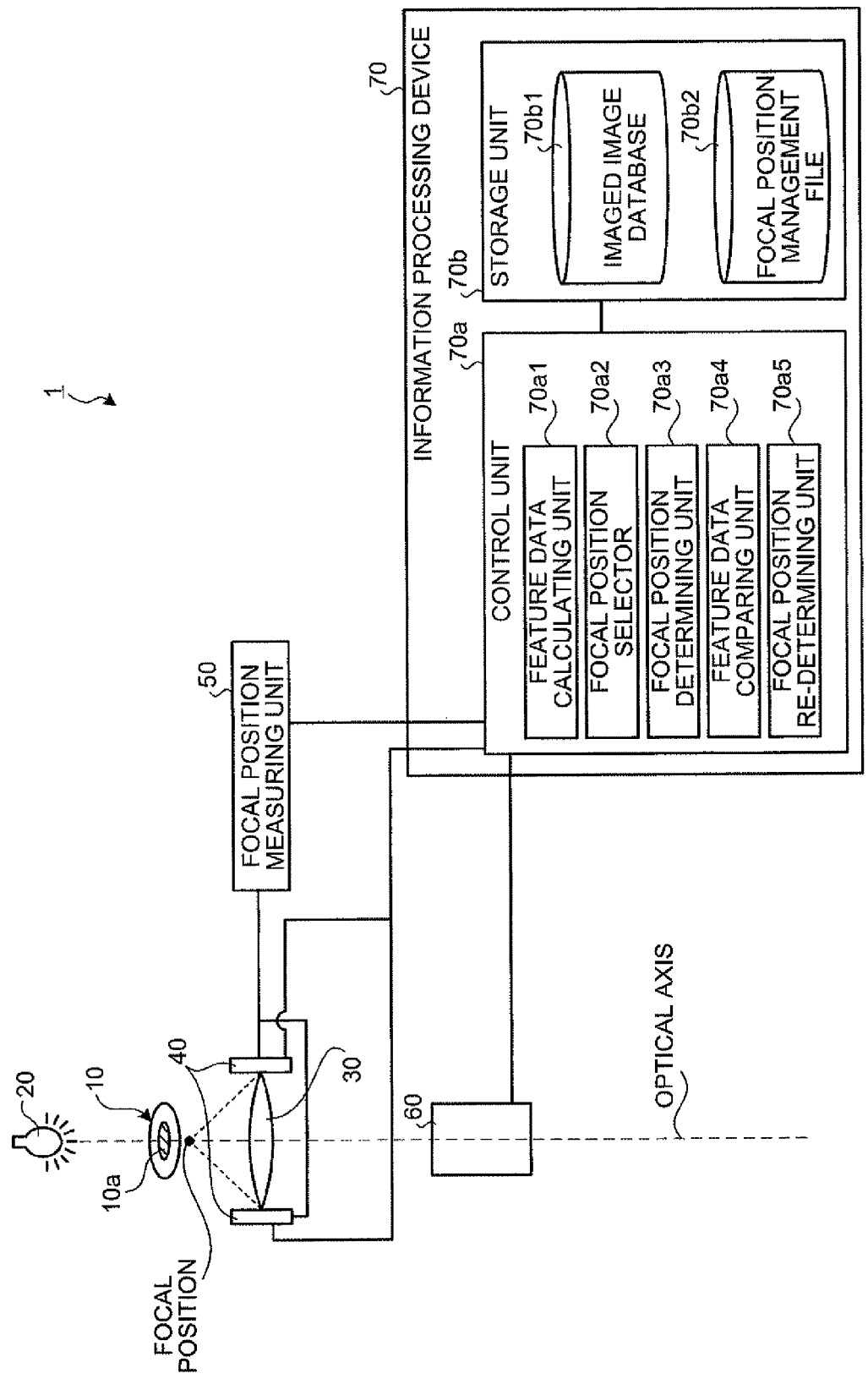
FIG. 12 is a view showing a basic configuration of a focal position determining apparatus 1 according to a first embodiment.

Next, the structure of the focal position determining apparatus 1 according to the first embodiment of the present invention will be explained in detail with reference to FIGS. 12 to 17. Firstly, the basic structure of the focal position determining apparatus 1 according to the first embodiment will be explained with reference to FIG. 12. FIG. 12 is a view showing a basic structure of the focal position determining apparatus 1 according to the first embodiment. The focal position determining apparatus 1 determines the focal position of an objective lens 30 focused on an observed target region 10a in a specimen 10 at the time of setting the specimen 10 such as a living cell or tissue for a luminescent observation. The focal position determining apparatus 1 includes, as shown in FIG. 12, a light irradiating unit 20, the objective lens 30, a focal position changing unit 40, a focal position measuring unit 50, a specimen imaging unit 60, and an information processing device 70.

The light irradiating unit (light source) 20 irradiates light to the specimen 10. The light irradiating unit 20 is an incoherent light source that emits light having a wavelength of visible light region (visible light). Specifically, the light irradiating unit 20 is a halogen lamp, LED (Light Emitting Diode), tungsten lamp, mercury lamp, etc. A coherent light source such as laser may be used as the light irradiating unit 20. In this case, the light (laser beam, or the like) emitted from the coherent light source is changed to an incoherent light with the use of a diffusion plate, and then, irradiated to the specimen 10. Further, a light source emitting infrared ray may be used as the light irradiating unit 20. In this case, since the determination of the focal position by infrared ray can be performed with non-illuminated state, the generation of an image noise caused by self-fluorescence can be prevented, and object information clearer than that obtained by visible light can be obtained. The determination of the focal position by means of infrared ray has an advantage that the determination of the focal position can be performed precisely. Light whose wavelength is partly overlapped with that of the feeble light to be detected, or light that has the same wavelength with that of the feeble light but can significantly detect the feeble light with strong light intensity and in a short period (e.g., within 0.5 second) can be used as irradiation light for determining the focal position.

The objective lens 30 is used for forming an image of the specimen 10. A variable focus lens may be employed as the objective lens 30. In order to make it possible to form an image by a feeble light, it is preferable that the square value of $(NA \div \beta)$ expressed by the numerical aperture (NA) and the projection magnification ($\beta$) of the objective lens is 0.01 or more, particularly 0.071 or more. The optical condition described above makes it possible to acquire an image by a feeble light in a practically exposure time (1 to 90 minutes) and short time. The optical condition described above can provide a feeble light image clearer than the image obtained by the exposure greater than the above-mentioned exposure, whereby the image analysis according to the feeble light image can be more advantageous.

The focal position changing unit 40 executes any one of moving any one of the position of the specimen 10 and the position of the objective lens 30 in the optical axis direction or both and changing the focal distance of the objective lens 30 or both, thereby changing the focal position of the objective lens 30.

The focal position measuring unit 50 is connected to the focal position changing unit 40 for measuring the focal position of the objective lens 30 based on at least one of the position of the specimen 10 on the optical axis, the position of the objective lens 30 on the optical axis, and the focal distance of the objective lens 30.

The specimen imaging unit 60 images the specimen 10. The specimen imaging unit 60 is specifically a high-sensitive CCD camera having an imaging device.

The information processing device 70 is specifically a commercially available personal computer, and is connected to the focal position changing unit 40, the focal position measuring unit 50 and the specimen imaging unit 60. The information processing device 70 includes a control unit 70*a* and a storage unit 70*b*. The control unit 70*a* is a CPU (Central Processing Unit) or the like that integrally controls the control unit 70*a*. The control unit 70*a* has an internal memory for storing a control program such as OS (Operating System), a program prescribing various process procedures, etc., and necessary data, and performs information processing for executing various processes based on the programs.

The control unit 70*a* controls each unit so as to repeatedly operate the focal position changing unit 40, the focal position measuring unit 50, the specimen imaging unit 60, and a later-described feature data calculating unit 70*a*1, and controls each unit provided to the control unit 70*a*. When an input device such as a keyboard or a mouse or an output device such as a TV (Television) monitor is connected to the information processing device 70, the control unit 70*a* acquires information input by the input device and outputs the information to the output device. The control unit 70*a* is composed of the feature data calculating unit 70*a*1, a focal position selector 70*a*2, a focal position determining unit 70*a*3, feature data comparing unit 70*a*4, and a focal position re-determining unit 70*a*5. The feature data calculating unit 70*a*1 calculates feature data (e.g., contrast of an imaged image, an integrated value of brightness of an imaged image, a statistical amount obtained from the brightness distribution of the imaged image, a ratio of a number of pixels having brightness exceeding a predetermined threshold value in the imaged image to the total pixel number, etc.) that characterizes the imaged image based on the imaged image taken by the specimen imaging unit 60. The focal position selector 70*a*2 selects at least one focal position from plural focal positions (focal positions measured at the focal position measuring unit 50) accumulated by the repeated execution of the units (specifically, the focal position changing unit 40, the focal position measuring unit 50, the specimen imaging unit 60, and the feature data calculating unit 70*a*1) by the control unit 70*a* based on the feature data accumulated by the repeated execution. The focal position determining unit 70*a*3 determines the focal position of the objective lens focused on the observed target region 10*a* in the specimen 10 based on the focal position selected by the focal position selector 70*a*2. The feature data comparing unit 70*a*4 compares the two feature data individually calculated beforehand at the feature data calculating unit 70*a*1. The focal position re-determining unit 70*a*5 again determines the focal position of the objective lens focused on the observed target region 10*a* in the specimen 10 based on the result of the comparison made by the feature data comparing unit 70*a*4.

The storage unit 70*b* is storage means. Specifically, a memory device such as a RAN (Random Access Memory) or ROM (Read Only Memory), a fixed disk device such as a hard disk, flexible disk, optical disk, etc., may be employed as the storage unit 70*b*. The storage unit 70*b* stores an imaged image database 70*b*1 and a focal position management file 70*b*2 as shown in the figure. The imaged image database 70*b*1 stores image identification information for uniquely identifying an imaged image, an imaged image, the focal position of the objective lens when the imaged image is taken, and the feature data of the imaged image, as associated with one another. The focal position management file 70*b*2 stores the focal position (specifically, the focal position determined by the focal position determining unit 70*a*3 or the focal position re-determined by the focal position re-determining unit 70*a*5) of the objective lens focused on the observed target region 10*a* in the specimen 10. The imaged image includes an illumination image, luminescent image and fluorescent image.

Figure 13:
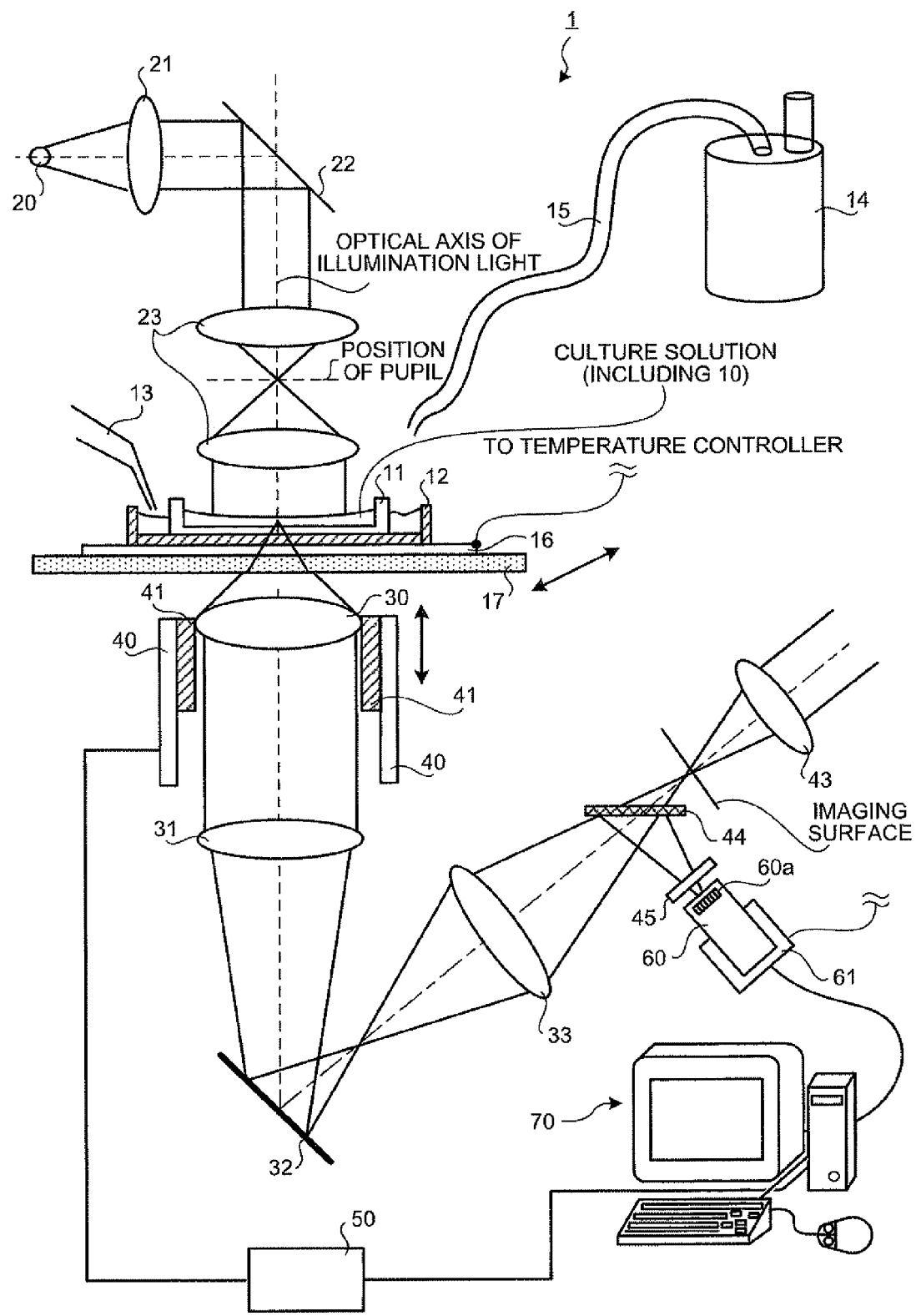
FIG. 13 is a view showing a specific example of the configuration of the focal position determining apparatus 1 according to the first embodiment.

Next, a specific example of the structure of the focal position determining apparatus 1 according to the first embodiment will be explained with reference to FIG. 13. The explanation overlapped with the aforesaid explanation may sometimes be omitted. FIG. 13 is a view showing a specific example of the structure of the focal position determining apparatus 1 according to the first embodiment. The focal position determining apparatus 1 shown in FIG. 13 has a structure with an inverted microscope as a base. Like the focal position determining apparatus 1 shown in FIG. 12, it is used for a luminescent observation of a living cell that emits feeble light. The focal position determining apparatus 1 shown in FIG. 13 includes, in addition to the aforesaid units (light irradiating unit 20, objective lens 30, focal position changing unit 40, focal position measuring unit 50, specimen imaging unit 60, information processing device 70), an illumination optical system, observation optical system, ocular lens 43, etc. Each of the units composing the focal position determining apparatus 1 will be explained below in detail.

The specimen 10 is immersed in culture solution put into a specimen container 11.

Figure 14:
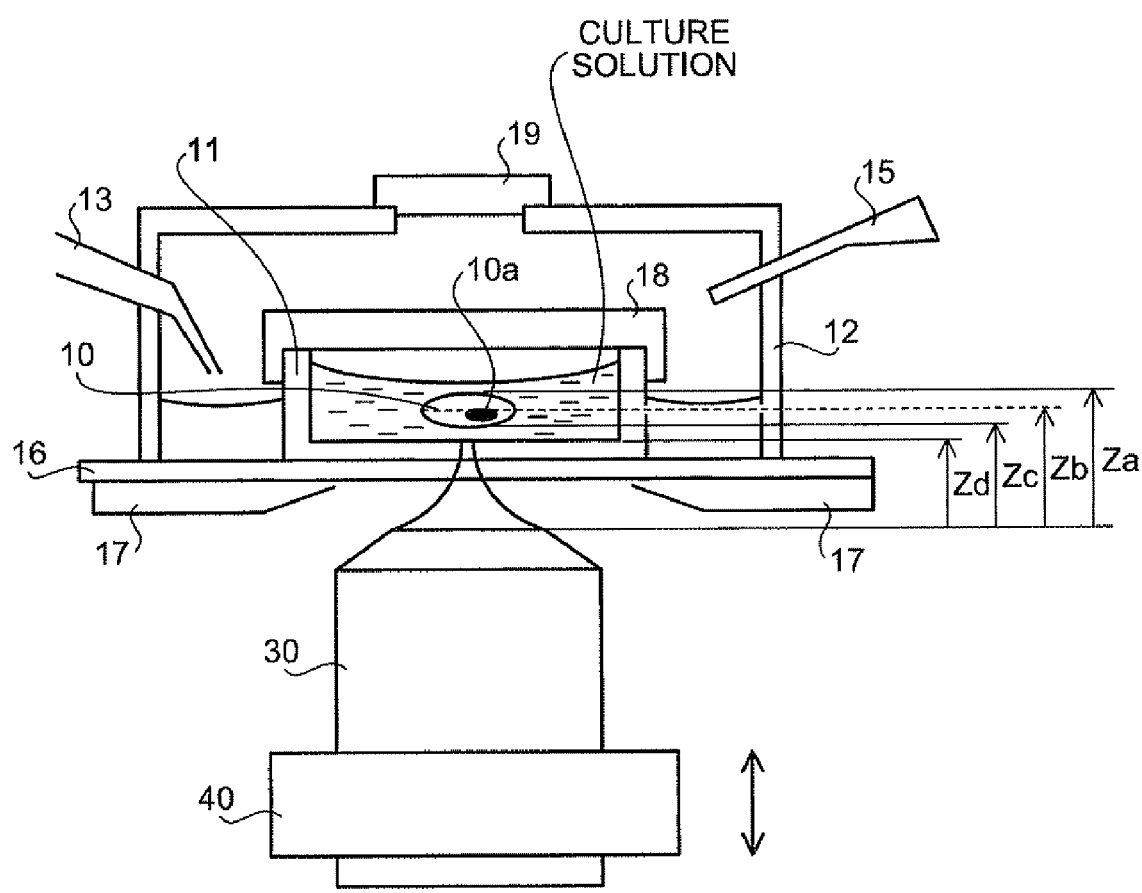
FIG. 14 is a view showing one example of configurations of components arranged in the vicinity of a specimen stage 17.

The specimen container 11 is specifically a petri dish, with at least its bottom surface being optically transparent (that can be handled with an ordinary objective lens). The bottom surface is made of a material same as a cover glass for a microscope, and has a thickness of 0.17 mm. A slide glass, or microplate can be used as the specimen container 11 instead of the petri dish. A cover 18 may be arranged on the specimen container 11 as shown in FIG. 14. Returning back to FIG. 13, the specimen container 11 is put into a water tank 12 filled with pure water supplied through a nozzle 13. The pure water is put into the water tank 12 in order to keep the humidity in the specimen container 11.

A gaseous mixture (including 5% of carbon dioxide ($CO_2$) and 95% of oxygen ($O_2$)) discharged from a gas cylinder 14 is fed from above the water tank 12 through a gas feed tube 15 with a flow rate of 50 mL/min. The water tank 12 may be formed into a shape enclosing the entire specimen container 11 as shown in FIG. 14. In this case, a detachable lid 19 is mounted to the upper part of the water tank 12. Returning back to FIG. 13, the water tank 12 is arranged on a heat plate 16.

The heat plate 16 is for setting an environment temperature, and arranged on the specimen stage 17. The heat plate 16 can perform the setting of the environment temperature at 0.5° C. intervals thanks to the control of a temperature controller (not shown) connected to the heat plate 16.

The specimen stage 17 is a plate-like member on which the specimen 10 or the like is set. The specimen stage 17 is arranged so as to be orthogonal to the optical axis (z axis) as shown in the figure. The specimen stage 17 is movable in the direction (e.g., x direction or y direction) orthogonal to the optical axis (z axis) from the position where the stage is arranged by the driving force of two stepping motors (not shown) mounted at the predetermined position of the stage so as to be orthogonal to each other (90° direction). Each of the stepping motors is controlled by a specimen stage controller (not shown) connected to the corresponding motor. The specimen stage controller is connected to the information processing device 70, whereby the specimen stage controller appropriately drives the corresponding stepping motor based on the instruction from the information processing device 70 so as to move the specimen stage 17.

The illumination optical system directs the illumination light emitted from the light source 20 to the specimen 10. The illumination optical system is composed of a collector lens 21, a deflection mirror 22 that deflects the optical axis of the illumination light, and a condenser lens 23 that projects an image of the light source 20.

Figure 15A:
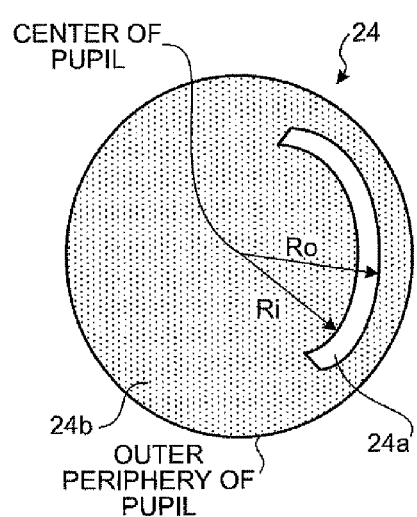
FIG. 15A is a view showing one example of a configuration of the aperture unit 24.
Figure 15B:
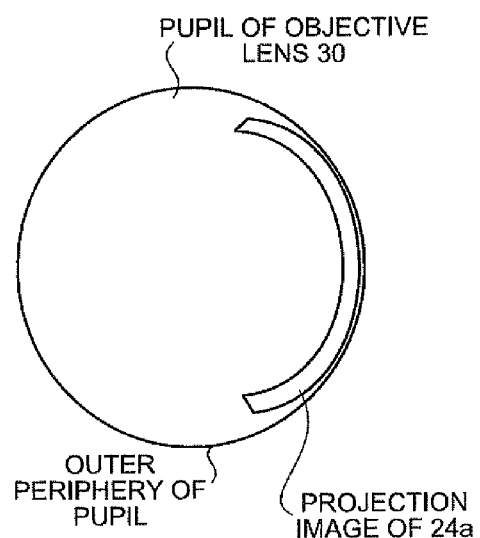
FIG. 15B is a view showing one example of a projection image of the aperture at the pupil of the objective lens 30.

An aperture unit 24 shown in FIG. 15A is detachably arranged at the pupil position of the condenser lens 23. FIGS. 15A and 15B are views showing the structure of the aperture unit 24 and one example of the projected image of an aperture at the pupil of the objective lens 30. The aperture unit 24 is composed of an aperture 24a of a partial annular zone and a light-shielding plate 24b having light shielding property. The aperture 24a is arranged relative to the optical axis so as to be decentered with respect to the center of the pupil, whereby the aperture 24a can freely laterally be shifted. The diameter of the aperture 24a is determined such that the projection image of the aperture 24a substantially touches internally the outer peripheral portion of the pupil of the objective lens 30 as shown in FIG. 15B. The width of the aperture 24a ("Ro−Ri" shown in FIG. 15A) is desirably not more than a third of the pupil radius of the objective lens 30 that is in conjugated relation. Thus, the moving amount of the objective lens 30 can appropriately be set depending upon the type of the living cell to be observed, whereby an image having the optimum contrast can be obtained.

Figure 16A:
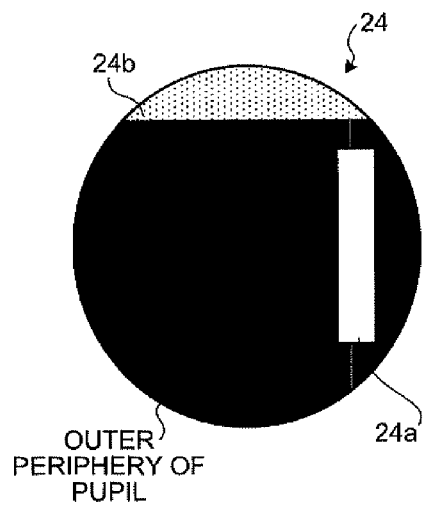
FIG. 16A is a view showing another configuration of the aperture unit 24.
Figure 16B:
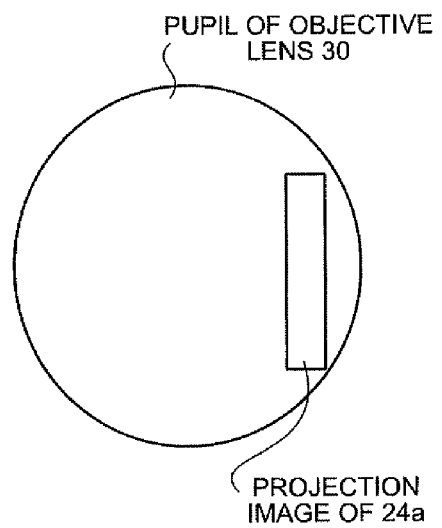
FIG. 16B is a view showing one example of a projection image of the aperture at the pupil of the objective lens 30.

The aperture unit 24 may be provided with the rectangular aperture 24a as shown in FIG. 16A. FIGS. 16A and 16B are views showing another example of the structure of the aperture unit 24 and the projection image of the aperture at the pupil of the objective lens 30. The rectangular aperture 24a is arranged at the position, apart from the central position of the pupil by a predetermined distance, as decentered relative to the center of the pupil.

When the specimen 10 is obliquely illuminated with the use of the aperture unit 24 having the rectangular aperture 24a, the image of the aperture 24a is projected on the pupil of the objective lens 30. Since the rectangular aperture 24a is not arranged cocentrically relative to the center of the pupil, an image having a high contrast can be obtained in a case where a living cell to be observed is long and slender. The oblique illumination light is incident on a living cell having a solid size, divided into transmitted light, refraction light and diffraction light, and emitted from the living cell. In the living cell, refraction light is greatly emitted from the portion that is the outline having a shape of approximately a sphere or ellipse, while transmitted light and diffraction light are greatly emitted from the flat portion. Some refraction lights refracted at the portion having the shape approximately a sphere or ellipse in the cell become greater than the NA of the objective lens 30, so that they are not taken into the objective lens 30.

Figure 17:
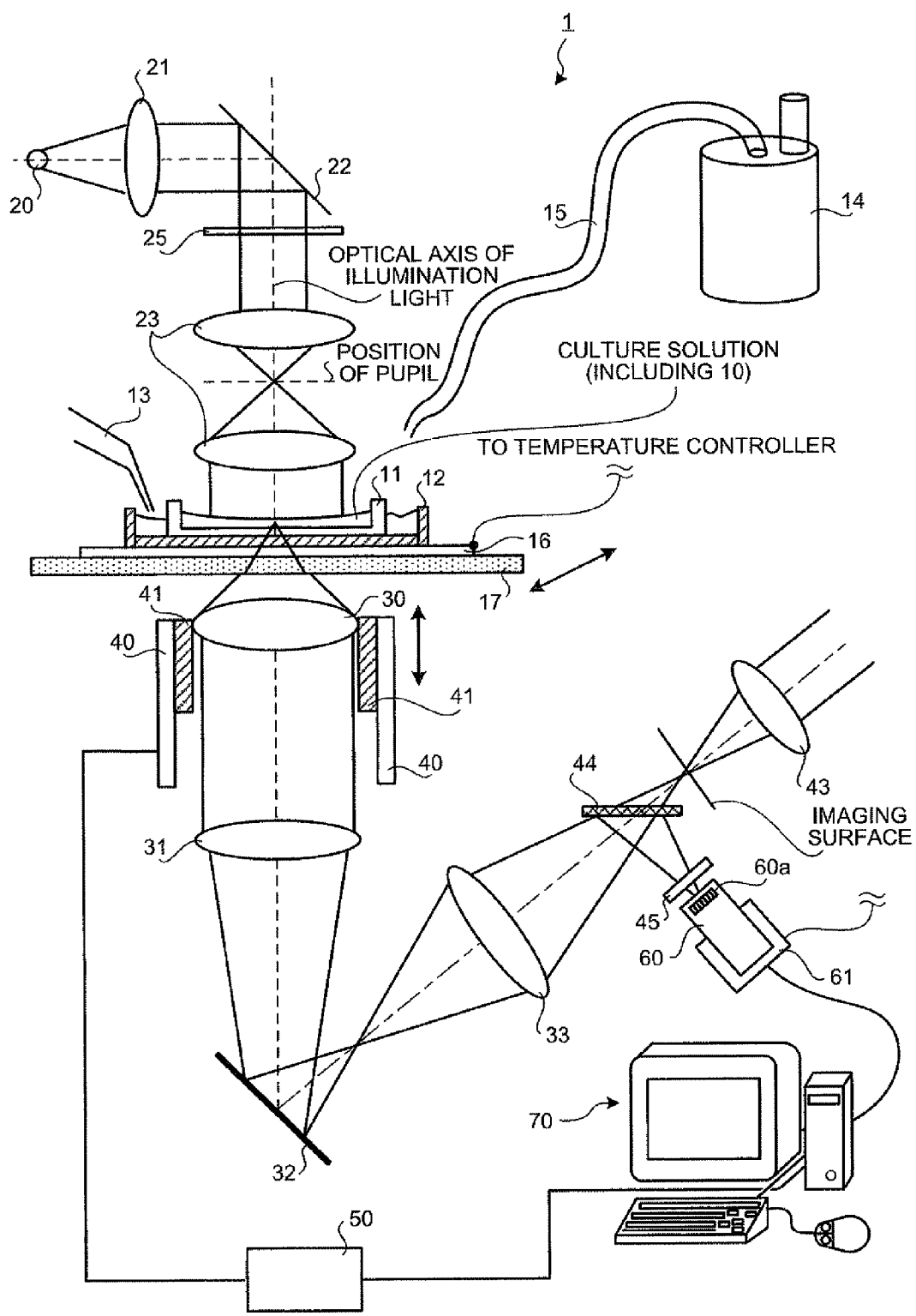
FIG. 17 is a view showing another specific example of the configuration of the focal position determining apparatus 1 according to the first embodiment.

As shown in FIG. 17, an interference filter 25 for providing the light source 20 having a quasi-monochromatic color may be arranged below the deflection mirror 22. With this structure, the illumination light emitted from the light source 20 is deflected by the deflection mirror 22, the deflected illumination light passes through the interference filter 25 to become a monochromatic light whose wavelength band width is extremely narrow, and then, directs toward the condenser lens 23. A narrow-band-pass filter may be employed instead of the interference filter.

Figure 26:
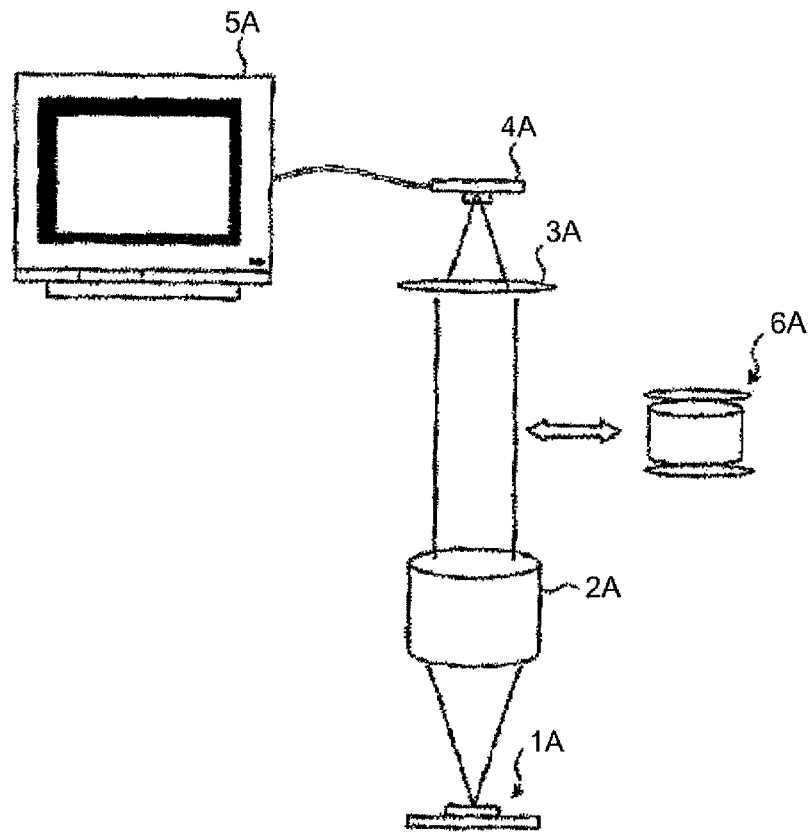
FIG. 26 is a view for showing one example of a configuration of an apparatus for executing a luminescent specimen imaging method according to the present embodiment.

Returning back to FIG. 13, the observation optical system is used for forming an image of the specimen 10, and arranged invertedly below the specimen stage 17. The observation optical system is composed of a relay lens 31 that images the image (image of the specimen 10) formed by the objective lens 30 on the imaging surface, a deflection mirror 32 that deflects the light from the objective lens 30, and a relay lens 33 that images the image (image of the specimen 10) formed by the objective lens 30 on the imaging surface with the relay lens 31, in addition to the objective lens 30. Therefore, the value of "square of (NA÷β)" that is the optical condition for the above-mentioned and later-described objective lens means the condition considering all lenses in the observation optical system. In the present invention, when the observation optical system other than the objective lens is determined, this condition is for explaining the selecting condition of the objective lens when the objective lens is replaced with an objective lens having a low magnification or high magnification, and this condition is not the optical condition determined only by the objective lens. In the present embodiment, the relay lenses 31 and 33 shown in FIG. 13 or a condenser lens 3A shown in FIG. 26 is indicated as the observation optical component other than the objective lens. The observation optical system described above is provided, whereby the cooperation with the image-capture by the feeble light can be optimized by cooperating the optical condition, which is determined by the high numerical aperture (NA) and the magnification, with the method or device to be applied.

The focal position changing unit 40 is specifically an objective lens z-axis moving (driving) mechanism that moves (drives) the objective lens 30 in the optical axis direction (z axis direction) by a rack-and-pinion mechanism (not shown). A knob included in the rack-and-pinion mechanism is rotated by a stepping motor (not shown) controlled by a computer. The objective lens z-axis moving mechanism may move the objective lens 30 in the optical axis direction by a friction roller mechanism instead of the rack-and-pinion mechanism. The focal position changing unit 40 may be configured to move the specimen stage 17 along the optical axis, instead of the structure in which the objective lens 30 is moved along the optical axis. As illustrated in the figure, an objective lens heater 41 is mounted in the objective lens z-axis moving mechanism.

The objective lens heater 41 is attached around the objective lens 30 as coming in contact with the objective lens 30 as illustrated in the figure. The objective lens heater 41 is controlled by a temperature adjusting device (not shown) connected to the objective lens heater 41. The objective lens heater 41 sets the temperature of the objective lens 30 from the outside of the objective lens 30 at 0.5° C. intervals so as to keep the temperature of the objective lens 30 constant.

The ocular lens 43 magnifies the image of the specimen 10. The ocular lens 43 is used for allowing an operator to visually observe the image of the specimen 10.

A switching mirror 44 is arranged between the ocular lens 43 and the relay lens 33 as shown in the figure. With this structure, the visual observation of the specimen 10 by the ocular lens 43 and the observation of the specimen 10 by the specimen imaging unit 60 can optionally be switched. In addition to the type of mechanically switching two optical paths, a type of separating two optical paths with the use of a half mirror may be employed as the switching mirror 44.

An infrared ray cut filter 45 is detachably mounted above the light-receiving surface of the specimen imaging unit 60 as shown in the figure for shielding infrared ray that becomes a background light. In other words, the infrared ray cut filter 45 prevents the infrared ray, which becomes the background light, from being incident on the specimen imaging unit 60, as needed.

The specimen imaging unit 60 is specifically a CCD camera having an imaging device 60a on its light-receiving surface. The pixel number of the imaging device 60a is 1360× 1024. The one having a sensitivity as high as possible is used for the CCD camera in order to be capable of detecting feeble light emitted from the specimen 10. A three-plate color camera may be used as the CCD camera in order to image a color bright-field image. The specimen imaging unit 60 is not limited to the CCD camera. For example, a CMOS (Complementary Metal Oxide Semiconductor) image sensor or SIT (Silicon Intensified Target) camera may be used as the specimen imaging unit 60. The specimen imaging unit 60 is connected to the information processing device 70 (a TV monitor connected to the information processing device 70) via a signal cable. A cooling device 61 is arranged at the bottom part of the specimen imaging unit 60 for preventing dark current emitted from the CCD camera.

The cooling device 61 is composed of a Peltier element for cooling the temperature of the specimen imaging unit 60 to 0° C. and keeping this temperature.

The information processing device 70 further has an input/output device (TV monitor, keyboard, mouser etc.). The information processing device 70 describes the image imaged by the specimen imaging unit 60 on a TV monitor.

In the focal position determining apparatus 1 shown in FIG. 13, light emitted from the light irradiating unit 20 is firstly made into parallel light by the collector lens 21, and this parallel light is projected at the position of the pupil of the condenser lens 23. The image of the light emitted from the light irradiating unit 20 illuminates the specimen 10 by the condenser lens 23 as Koehler illumination. The light illuminating the specimen 10 transmits the specimen 10 to be incident on the objective lens 30. Then, the light (measurement light) incident on the objective lens 30 forms an image of the specimen 10 by the objective lens 30, the relay lens 31 and the relay lens 32 on the imaging surface. The image of the specimen 10 formed on the imaging surface is incident intact on the ocular lens 43 and is imaged on the imaging device 60a of the CCD camera 60 by the switching mirror 44.

The explanation of the focal position determining apparatus 1 according to the first embodiment is now ended here.

3. Process of Focal Position Determining Apparatus 1

Figure 18:
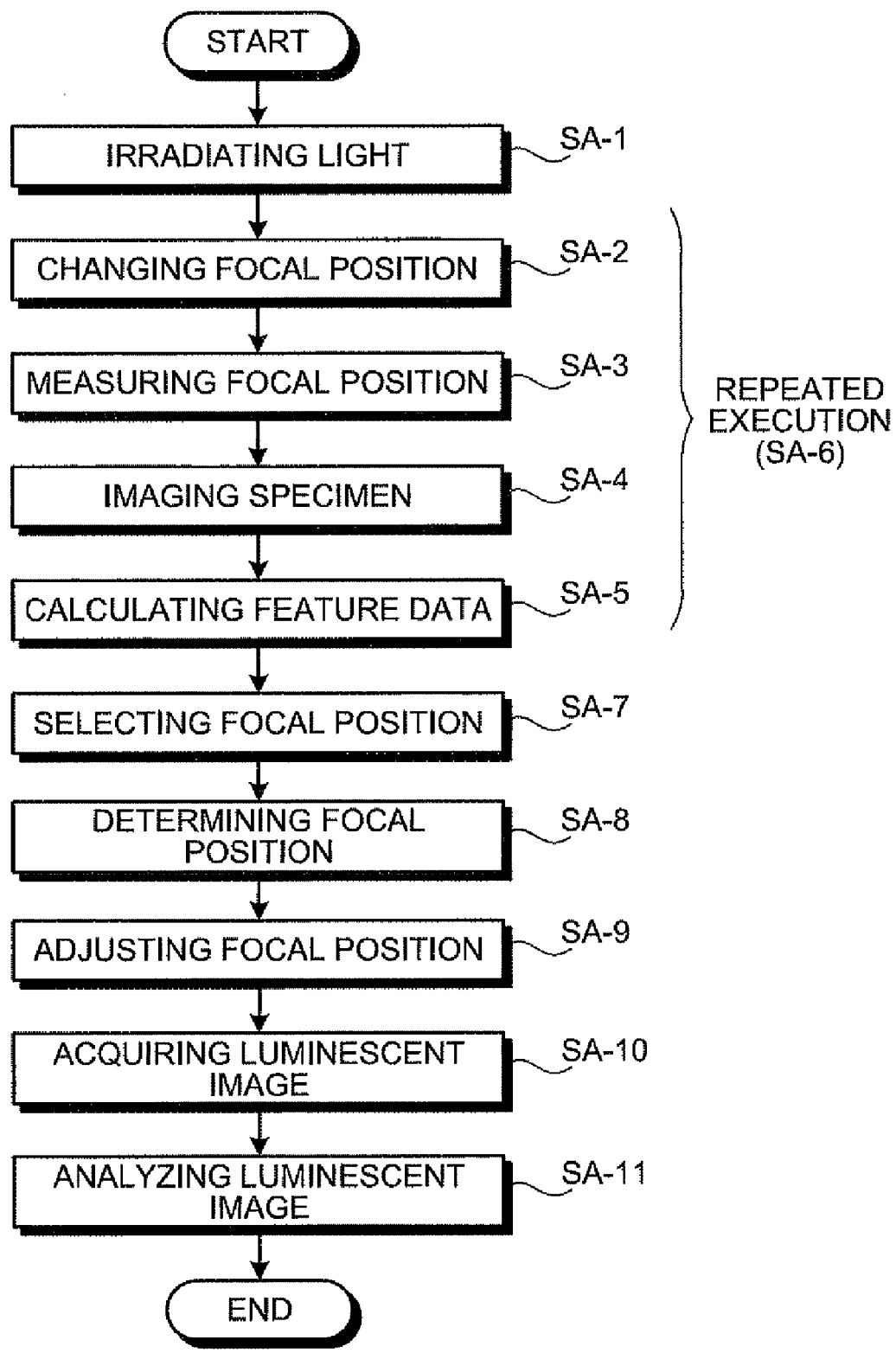
FIG. 18 is a flowchart showing one example of a focal position determining process executed by the focal position determining apparatus 1 according to the first embodiment.

Next, the focal position determining process executed by the focal position determining apparatus 1 according to the first embodiment will be explained with reference to FIG. 18. FIG. 18 is a flowchart showing one example of the focal position determining process executed by the focal position determining apparatus 1 according to the first embodiment. The focal position determining process in which a luminescence observation of a living cell is performed by using the focal position determining apparatus 1 shown in FIG. 13 will be explained here.

When an operator sets the specimen container 11 in which a living cell that is the specimen 10 is put on the specimen stage 17, and starts the focal position determining apparatus 1 and the light source 20, the focal position determining apparatus 1 performs the following process.

Firstly, the focal position determining apparatus 1 irradiates the illumination light emitted from the light source 20 to the living cell (step SA-1).

Next, the focal position determining apparatus 1 operates the objective lens z-axis moving mechanism, which is the focal position changing unit 40, by the control unit 70a of the information processing device 70, so as to move the objective lens 30 from the initial position along the optical axis by a predetermined amount by the objective lens z-axis moving mechanism. Therefore, the focal position of the objective lens 30 is changed (step SA-2).

Then, the focal position determining apparatus 1 operates the focal position measuring unit 50 by the control unit 70a of the information processing device 70 so as to measure the focal position of the objective lens 30 by the focal position measuring unit 50 (step SA-3).

Next, the focal position determining apparatus 1 operates the CCD camera, which is the specimen imaging unit 60, by the control unit 70a of the information processing device 70 so as to image the living cell by the CCD camera (step SA-4).

Then, the focal position determining apparatus 1 operates the feature data calculating unit 70a1 by the control unit 70a of the information processing device 70 so as to calculate a contrast of the imaged image by the feature data calculating unit 70a1 based on the image imaged at the step SA-4 (step SA-5).

The focal position determining apparatus 1 stores the focal position measured at the step SA-3, the image imaged at the step SA-4 and the contrast calculated at the step SA-5 in the imaged image database 70b1 of the storage unit 70b, as associated with one another, by the control unit 70a of the information processing device 70.

Next, the focal position determining apparatus 1 repeatedly executes the processes from the step SA-2 to the step SA-5 by the control unit 70a of the information processing device 70, until the focal position of the objective lens 30 that is changed at the step SA-2 exceeds the predetermined position on the optical axis (step SA-6).

Then, the focal position determining apparatus 1 operates the focal position selector 70a2 by the control unit 70a of the information processing device 70 so as to select two contrasts, among the plural contrasts stored in the imaged image database 70b1, which are the maximum, and acquires the focal position stored in the imaged image database 70b1 as associated with the selected contrast by the focal position selector 70a2 (step SA-7). In other words, the focal position determining apparatus 1 selects the focal position (substantial focal position) at the near point of the objective lens 30 and the focal position (substantial focal position) at the far point of the objective lens 30 from the plural focal positions stored in the imaged image database 70b1 based on the plural feature data stored in the imaged image database 70b1 by the focal position selector 70a2.

Then, the focal position determining apparatus 1 operates the focal position determining unit 70a3 by the control unit 70a of the information processing device 70 so as to determine the central position (the position at the approximate center) between two focal positions as the focal position of the objective lens 30 focused on the observed target region 10a in the living cell by the focal position determining unit 70a3 based on the two focal positions selected at the step SA-7 (step SA-8).

Next, the focal position determining apparatus 1 operates the objective lens z-axis moving mechanism by the control unit 70a of the information processing device 70 so as to adjust the position of the objective lens 30 by the objective lens z-axis moving mechanism in such a manner that the focal position of the objective lens 30 is focused on the central position (the position at the approximate center) determined at the step SA-8 (step SA-9). By using the focal position thus adjusted, the luminescent image serving as the feeble light image is acquired, and the luminescent image is analyzed (step SA-10, 11). The luminescent image can more quickly and correctly be analyzed, because it is analyzed together with the illumination image obtained through the irradiation of light.

As explained above, the focal position determining apparatus 1 according to the first embodiment irradiates illumination light to the living cell from the light source 20. Then, the focal position determining apparatus 1 repeatedly moves the objective lens 30 along the optical axis by a predetermined amount by the objective lens z-axis moving mechanism, and every time the objective lens 30 is moved, it measures the focal position of the objective lens 30 by the focal position measuring unit 50. The focal position determining apparatus 1 illuminates and images the living cell by the CCD camera, and calculates the contrast of the imaged image by the feature data calculating unit 70a1. The focal position determining apparatus 1 then selects two maximum contrasts, among the accumulated plural contrasts obtained by repeatedly moving the objective lens 30, by the focal position selector 70a2, and acquires the focal positions of the objective lens 30 when the images corresponding to the selected contrasts are imaged from the accumulated plural focal positions obtained by repeatedly moving the objective lens 30. Then, the focal position determining apparatus 1 determines, by the focal position determining unit 70a3, the central position (the position at the approximate center) between two focal positions as the focal position of the objective lens 30 focused on the observed target region 10a in the living cell, and moves the objective lens 30 by the objective lens z-axis moving mechanism so as to adjust the focal position of the objective lens 30 to the determined focal position. Accordingly, when the specific region in the living cell is defined as the observed target region 10a and the luminescent observation of the observed target region 10a is performed, the focal position of the objective lens 30 focused on the observed target region 10a can be determined at the time of setting the living cell, with the result that the focal position of the objective lens 30 can be focused on the observed target region 10a. Specifically, according to the focal position determining apparatus 1, the objective lens can automatically be focused on a luminescent region (a region where a bioluminescent protein is located) in a living cell without confirming the luminescence from the living cell, in a microscope that observes a living cell, which emits feeble light, with the use of magnification imaging optical means including a lens, measures luminescence from the living cell, or observes feeble luminescence from a bioluminescent protein in the living cell, for example. Accordingly, when a specimen emitting feeble light is observed with the use of magnification imaging optical means including a lens, the focal position of the objective lens can quickly and precisely be set to the target region in the specimen, compared to the manual setting. The focal position determining apparatus 1 employs an illumination image of a specimen for determining the focal position of the objective lens. This illumination image is bright and has a high contrast. Therefore, compared to the case in which the focal position of the objective lens 30 focused on the observed target region 10a in the specimen 10 is visually set, the focal position of the objective lens 30 focused on the observed target region 10a in the specimen 10 can easily and quickly be determined. Further, in the focal position determining apparatus 1, the focal positions of the objective lens 30 when the illumination image of the specimen 10 with high contrast is imaged correspond to the substantial upper and lower peripheral edge portions of the specimen 10, the central position (substantial central position) between them may be determined as the focal position of the objective lens 30 focused on the observed target region 10a in the specimen 10. Thus, the focal position of the objective lens 30 focused on the observed target region 10a in the specimen 10 can easily and simply be determined.

Since the intensity of luminescence from a living body (living cell, or the like) is extremely feeble at the time of setting the specimen when a luminescent phenomenon of the living body is measured, the feeble light cannot be detected even by a high-performance CCD camera. Specifically, the objective lens cannot be focused while confirming the observed target region (cell, or the like) in the living body like an ordinary microscopic observation. In other words, an internal structure of a living body cannot be observed at the time of setting the living body. When regions where bioluminescent protein is localized in cell (that emit feeble light) are simultaneously observed in both cells by a microscope that is used for the observation of fluorescence or luminescence (chemiluminescence or bioluminescence), the objective lens is not focused on the luminescent region of the luminescent protein localized in the cell at the focal position of the objective lens detected based on the illumination image of the phase object such as a cell, so that the observation image may be blurred. In the fluorescent observation, the position where the fluorescent intensity is the greatest in the phase object emitting fluorescence by fluorescent exciting light is determined as the focal position. In this determination method, it is necessary to reduce the number of times of the determination of the focal position as much as possible, since the phototoxicity caused by the exciting light is strong, and it is undesirable to repeatedly determine the focal position to the specimen such as a living cell having bioactivity. However, when the number of times of the determination of the focal position is reduced in a long-term fluorescent observation, the resolution of the observation image might be unstable. In view of this, in the focal position determining apparatus 1, light emitted from the light source 20, such as a halogen lamp, is irradiated to a living body so as to acquire an illumination image of the living body by a microscope, and the focal position of the objective lens 30 is determined based on the acquired illumination image as an image observation by illumination light. Specifically, a living cell is imaged under illumination for estimating the position of the inside of the living cell. Accordingly, the internal structure of the living body can be observed at the time of setting the living body. Further, when regions (that emit feeble light) where bioluminescent protein is localized in a cell are simultaneously observed in both cells, the objective lens can be focused on the luminescent region of the bioluminescent protein localized in the cell. Further, the focal position determining apparatus 1 does not determine the focal position of the objective lens by using fluorescence, a long-term fluorescent observation can be carried out.

The focal position determining apparatus 1 may select the focal position of the objective lens 30 at the near point (the focal position of the objective lens 30 when an imaged image having a high contrast is obtained at the near point of the objective lens 30) by the focal position selector 70a2 from the plural focal positions stored in the imaged image database 70b1 based on the plural feature data stored in the imaged image database 70b1 at the step SA-7, and may determine, by the focal position determining unit 70a3, the position apart upwardly of the optical axis from the selected focal position of the objective lens 30 at the near point by a distance a half the thickness of the living cell that has already been measured as the focal position of the objective lens 30 focused on the observed target region 10*a* in the living cell at the step SA-8. In other words, the focal position determining apparatus 1 may select the focal position of the objective lens 30 at the near point when an image having a high contrast is obtained in the observation under illumination, and determine the position apart upwardly of the optical axis from the selected focal position by a distance a half the thickness of the living cell as the focal position of the objective lens 30 focused on the observed target region 10*a* in the living cell. The focal position determining apparatus 1 may select the focal position of the objective lens 30 at the far point (the focal position of the objective lens 30 when an imaged image having a high contrast is obtained at the far point of the objective lens 30) by the focal position selector 70*a*2 from the plural focal positions stored in the imaged image database 70*b*1 based on the plural feature data stored in the imaged image database 70*b*1 at the step SA-7, and may determine, by the focal position determining unit 70*a*3, the position apart downwardly of the optical axis from the selected focal position of the objective lens 30 at the far point by a distance a half the thickness of the living cell that has already been measured as the focal position of the objective lens 30 focused on the observed target region 10*a* in the living cell at the step SA-8. In other words, the focal position determining apparatus 1 may select the focal position of the objective lens 30 at the far point when an image having a high contrast is obtained in the observation under illumination, and determine the position apart downwardly of the optical axis from the selected focal position by a distance a half the thickness of the living cell as the focal position of the objective lens 30 focused on the observed target region 10*a* in the living cell. Thus, compared to the case in which the objective lens 30 or the specimen 10 is moved to select the defocus position at the near point and at the far point, the focal position of the objective lens focused on the observed target region 10*a* in the specimen 10 can easily and simply be determined.

The focal position determining apparatus 1 may execute a step 1 to a step 6 described below so as to determine the focal position of the objective lens 30 focused on the observed target region 10*a* in a living cell arranged in the specimen container 11.

(Step 1) The power of the light source 20 is turned on, and the shutter of the light source 20 is opened and closed to irradiate illumination light from above the specimen container 11.

(Step 2) The focal position (corresponding to "Zd" in FIG. 14) of the objective lens 30 focused on the bottom surface (outer bottom surface or inner bottom surface) of the specimen container 11 is determined. Specifically, the objective lens 30 is moved along the optical axis by the objective lens z-axis moving mechanism by a predetermined amount, and every time the objective lens 30 is moved by the predetermined amount, the living cell is imaged under the illumination by the CCD camera. The integrated value (intensity of the output signal from the CCD camera) of the light intensity from all pixels of the imaged image is calculated by the feature data calculating unit 70*a*1. The control unit 70*a* confirms whether the calculated integrated value is the maximum value or not. When the calculated integrated value is confirmed to be the maximum value, it is considered that the objective lens 30 is focused on the bottom surface of the specimen container 11 when the imaged image, which is the original of the maximum value, is imaged, so that the focal position (corresponding to "Zd" in FIG. 14) of the objective lens 30 at the time of imaging is measured by the focal position measuring unit 50. Specifically, the maximum value of the reflection light from the bottom surface of the specimen container 11 is determined with the illumination image, while moving the objective lens 30 along the optical axis.

(Step 3) The focal position (corresponding to "Zc" in FIG. 14) of the objective lens 30 when the image having a high contrast is imaged is determined at the near point of the objective lens 30. Specifically, the objective lens 30 is further moved from the position where the objective lens is moved at the (step 2) along the optical axis by a predetermined amount by the objective lens z-axis moving mechanism, and every time the objective lens 30 is moved by the predetermined amount, the living cell is imaged under the illumination by the CCD camera. The contrast of the imaged image is calculated by the feature data calculating unit 70*a*1, and the control unit 70*a* confirms whether the calculated contrast is the maximum value or not. When it is confirmed that the calculated contrast is the maximum value, it is considered that the objective lens 30 is focused on the substantial lower end surface of the living cell when the imaged image, which is the original of the maximum value, is imaged, so that the focal position (corresponding to "Zc" in FIG. 14) of the objective lens 30 at the time of imaging is measured by the focal position measuring unit 50.

(Step 4) The focal position (corresponding to "Za" in FIG. 14) of the objective lens 30 when the image having a high contrast is imaged is determined at the far point of the objective lens 30. Specifically, the objective lens 30 is further moved from the position where the objective lens is moved at the (step 3) along the optical axis by a predetermined amount by the objective lens z-axis moving mechanism, and every time the objective lens 30 is moved by the predetermined amount, the living cell is imaged under the illumination by the CCD camera. The contrast of the imaged image is calculated by the feature data calculating unit 70*a*1, and the control unit 70*a* confirms whether the calculated contrast is the maximum value or not. When it is confirmed that the calculated contrast is the maximum value, it is considered that the objective lens 30 is focused on the substantial upper end surface of the living cell when the imaged image, which is the original of the maximum value, is imaged, so that the focal position (corresponding to "Za" in FIG. 14) of the objective lens 30 at the time of imaging is measured by the focal position measuring unit 50.

(Step 5) The position (e.g., corresponding to "Zb((Zc+Za)÷2)" in FIG. 14) at approximately the center between the focal position (corresponding to "Zc" in FIG. 14) determined at the (step 3) and the focal position (corresponding to "Za" in FIG. 14) determined at the (step 4) is determined as the focal position of the objective lens 30 focused on the observed target region 10*a* in the living cell.

(Step 6) The objective lens 30 is moved such that the focal position of the objective lens 30 is adjusted to the central position determined at the (step 5).

The focal position of the objective lens 30 corresponding to "Zc" or "Za" in FIG. 14 may be determined at the step 4 and the step 5 as described below. Specifically, every time the objective lens 30 is moved by a predetermined amount, the living cell is imaged under the illumination by the CCD camera, and the focal position of the objective lens 30 at the time of the imaging is measured. The contrasts (sum of the output signals from each pixel of the plural imaged images) of the plural imaged images taken as moving the objective lens 30 are calculated. The calculated contrasts (sum) are compared to one another so as to select the maximum contrast (sum), and the focal position of the objective lens 30 when the imaged image corresponding to the selected contrast (sum) is imaged is selected from the plural focal positions of the objective lens 30 measured as moving the objective lens 30, whereby the focal position of the objective lens 30 corresponding to "Zc" or "Za" in FIG. 14 is determined. The focal position determining apparatus 1 may be provided with a photodiode instead of the CCD camera. In this case, at the step 4 and the step 5, every time the objective lens 30 is moved by a predetermined amount, the output current of the photodiode may be amplified and converted into a voltage signal, as well as the focal position of the objective lens 30 may be measured. The intensities of the plural voltage signals converted as moving the objective lens 30 may be compared to one another so as to select the intensity of the maximum voltage signal. The focal position of the objective lens 30 corresponding to the intensity of the selected voltage signal may be selected from the plural focal positions of the objective lens 30 measured as moving the objective lens 30, whereby the focal position of the objective lens 30 corresponding to "Zc" or "Za" in FIG. 14 may be determined. In the focal position determining apparatus 1, the amount (moving amount) for moving the objective lens 30 or the specimen 10 is desirably within the range with which the image taken by the CCD camera is not blurred. Specifically, the moving amount is desirably not more than the value ($\lambda \div NA^2$: $\lambda$ is a wavelength, NA is a numerical aperture) obtained by dividing the wavelength of the light emitted from the light source 20 by the square of NA of the objective lens 30.

The focal position determining apparatus 1 may employ, as the light source 20, a light source (such as a laser) having high monochromaticity. When the monochromaticity of the light source is high, little wavelength distribution appears when illumination light is irradiated to the phase object, whereby a sharp diffraction light can be obtained. Therefore, the contrast of the image imaged at the near point and the contrast of the image imaged at the far point become extremely high compared to the case of using white light source. Accordingly, the focal position of the objective lens when the image having the maximum contrast is imaged can easily be selected.

In the focal position determining apparatus 1, an operator may visually determine two positions of the objective lens where the contrast of the image of the living cell becomes high through the ocular lens 43 while manually turning the knob of the objective lens z-axis moving mechanism, the determined focal position of the objective lens may be measured by the focal position measuring unit 50, and the central position (substantial central position) between the measured two focal positions may be determined as the focal position of the objective lens focused on the observed target region 10*a* in the living cell by the focal position determining unit 70*a*3.

According to the focal position determining apparatus 1, the position of the objective lens 30 is moved in the forward direction or rearward direction by a slight amount relative to the specimen 10 from the focusing position in an ordinary observation, whereby an image having a contrast same as that in the phase contrast observation can be obtained without using an objective lens for a phase contrast. Further, according to the focal position determining apparatus 1, it is unnecessary to consider the pupil aberration between the objective lens 30 and the condenser lens 23, whereby an objective lens having a low magnification can be used. Specifically, according to the focal position determining apparatus 1, a phase object such as a cultured cell can be observed even by using an objective lens at ×1 or ×2 magnification that cannot be used in the phase contrast observation. Therefore, an observation in a wide range, which cannot be realized in a conventional observation method, can be performed. According to the focal position determining apparatus 1, an image having a high contrast and a relief-like texture in which the phase distribution is shaded can be obtained by oblique illumination. The focal position determining apparatus 1 can switch the visual observation and the observation by the TV monitor by the switching mirror 44. By using a half mirror as the switching mirror 44, the visual observation and the observation by the TV monitor can simultaneously be performed. When the aperture is removed, the focal position determining apparatus 1 can be employed as an ordinary microscope to observe a specimen. According to the focal position determining apparatus 1, the focal position of the objective lens 30 is determined in two steps, whereby a focal position can be determined even when an objective lens having a high magnification is used. Since the focal position determining apparatus 1 does not use exciting light, the focal position determining apparatus 1 has an advantage that there is little affect by phototoxicity even if the focal position determining process is repeatedly executed to a biological specimen emitting fluorescence. In other words, in a case where a living cell is continuously observed over time, a clear image can be continuously imaged by repeating the focal position determining process. When the focal position determining process is performed by using infrared ray in the focal position determining apparatus 1, the focal position of the objective lens is adjusted and further, a dark field image of a specimen can be imaged, while maintaining the state in which the illumination by visible light is not performed. Therefore, it can effectively be prevented that noise is caused on the imaged image due to self-luminescence.

Figure 19:
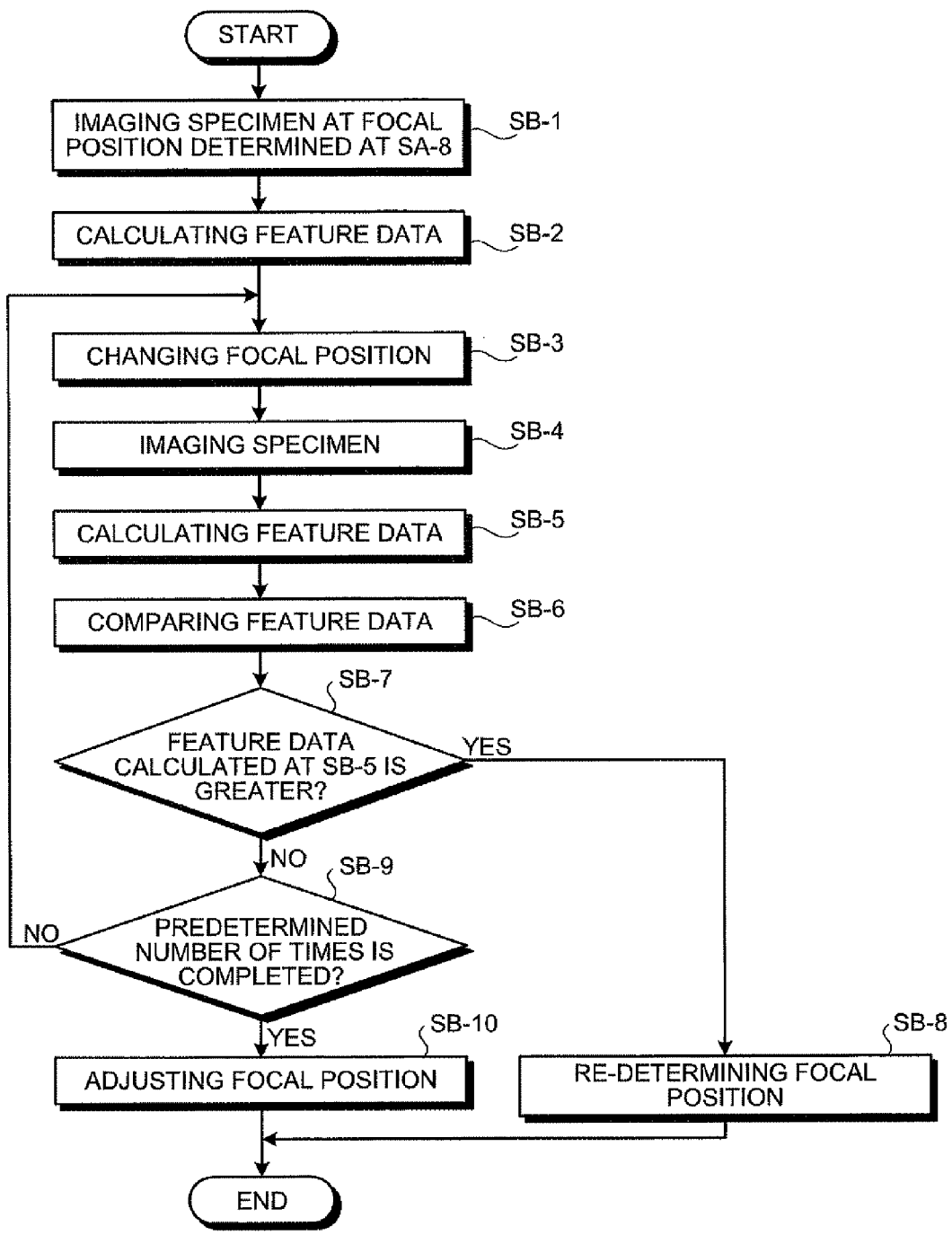
FIG. 19 is a flowchart showing one example of a focal position re-determining process executed by the focal position determining apparatus 1 according to the first embodiment.

When the intensity of the luminescence emitted from the specimen 10 is in the degree that can be detected by the CCD camera, the focal position determining apparatus 1 may re-determine the focal position of the objective lens focused on the observed target region 10*a* in the specimen 10, which focal position is determined at the time of setting the specimen 10 (focal position re-determining process). When the luminescence from the specimen 10 is observed by the objective lens 30 having high magnification (e.g., ×40 or more), the image of the specimen 10 is blurred unless the focal position of the objective lens 30 is accurately focused on the observed target region 10*a* in the specimen 10, since the focal depth becomes extremely shallow as the magnification of the objective lens 30 increases. Although the focal position determined by the aforesaid focal position determining process is focused on the approximate center of the specimen 10, it is necessary to determine the focal position of the objective lens 30 more precisely focused on the observed target region 10*a* in the specimen 10, when the luminescence from the specimen 10 is acquired with high precision. In view of this, the focal position re-determining process is executed, whereby the focal position of the objective lens focused on the observed target region 10*a* in the specimen 10 can be continuously determined not only at the time of setting the specimen 10 but also after the start of the luminescent observation of the specimen 10. As a result, the focal position of the objective lens can always be focused on the observed target region 10*a*. The focal position re-determining process executed by the focal position determining apparatus 1 will be explained with reference to FIG. 19. FIG. 19 is a flowchart showing one example of the focal position re-determining process executed by the focal position determining apparatus 1 according to the first embodiment.

Firstly, the focal position determining apparatus 1 operates the CCD camera by the control unit 70*a* so as to image the specimen 10 by the CCD camera without the illumination at the focal position (the focal position of the objective lens 30 determined at the step SA-8 in FIG. 18 and focused on the observed target region 10a in the specimen 10) determined by the focal position determining unit 70a3 (step SB-1).

Then, the focal position determining apparatus 1 operates the feature data calculating unit 70a1 by the control unit 70a so as to calculate feature data (e.g., luminescent intensity from each pixel of the luminescent image, statistical amount obtained from the luminescent intensity distribution of the luminescent image, contrast of the luminescent image) by the feature data calculating unit 70a1 based on the image (luminescent image) imaged at the step SB-1 (step SB-2).

Next, the focal position determining apparatus 1 operates the objective lens z-axis moving mechanism by the control unit 70a so as to move the objective lens 30 by the objective lens z-axis moving mechanism along the optical axis by a predetermined amount, thereby changing the focal position determined by the focal position determining unit 70a3 (step SB-3) The focal position may be changed not only by moving the objective lens 30 but also by moving the specimen stage 17.

Then, the focal position determining apparatus 1 operates the CCD camera by the control unit 70a so as to image by the CCD camera the specimen 10 without the illumination at the focal position changed at the step SB-3 (step SB-4).

Next, the focal position determining apparatus 1 operates the feature data calculating unit 70a1 by the control unit 70a so as to calculate feature data (e.g., luminescent intensity from each pixel of the luminescent image, statistical amount obtained from the luminescent intensity distribution of the luminescent image, contrast of the luminescent image) by the feature data calculating unit 70a1 based on the image (luminescent image) imaged at the step SB-4 (step SB-5).

Then, the focal position determining apparatus 1 operates the feature data comparing unit 70a4 by the control unit 70a so as to compare the feature data calculated at the step SB-2 and the feature data calculated at the step SB-5 by the feature data comparing unit 70a4 (step SB-6). In the comparison of the feature data, there may be the case in which the feature data are appropriately compared by a contrast or the case in which the feature data are appropriately compared by the statistical amount obtained from the distribution of the luminescent intensity depending upon the type or property of the specimen 10, but finally, the feature data are compared by an S/N (signal-to-noise ratio).

Next, when the feature data calculated at the step SB-5 is greater as a result of the comparison at the step SB-6 (step SB-7: Yes), the focal position determining apparatus 1 operates the focal position determining unit 70a5 by the control unit 70a so as to determine the focal position changed at the step SB-3 as the focal position of the objective lens focused on the observed target region 10a in the living cell by the focal position determining unit 70a5 (step SB-8).

On the other hand, when the feature data calculated at the step SB-5 is not greater as a result of the comparison at the step SB-6 (step SB-7: No), the focal position determining apparatus 1 confirms, by the control unit 70a, whether or not the number of times of the execution at the step SB-3 reaches the predetermined number of times (whether or not the moving amount of the objective lens 30 at the step SB-3 reaches the predetermined amount). When it reaches the predetermined number of times (step SB-9: Yes), the focal position determining apparatus 1 operates the objective lens z-axis moving mechanism by the control unit 70a so as to return the focal position of the objective lens 30 changed at the step SB-3 to the focal position determined at the beginning by the focal position determining unit 70a3 (the focal position of the objective lens 30 determined at the step SA-8 in FIG. 18 and focused on the observed target region 10a in the living cell) (step SB-10). When the number of times of the execution does not reach the predetermined number of times (step SB-9: No), the focal position determining apparatus 1 returns to the process at the step SB-3 by the control unit 70a.

The explanation of the focal position determining apparatus 1 according to the first embodiment is now ended.

Second Embodiment

Next, the structure of the focal position determining apparatus 1 according to the second embodiment will be explained in detail with reference to FIGS. 20 to 22. The explanation of the parts overlapped with those in the first embodiment may sometimes be omitted.

Figure 20:
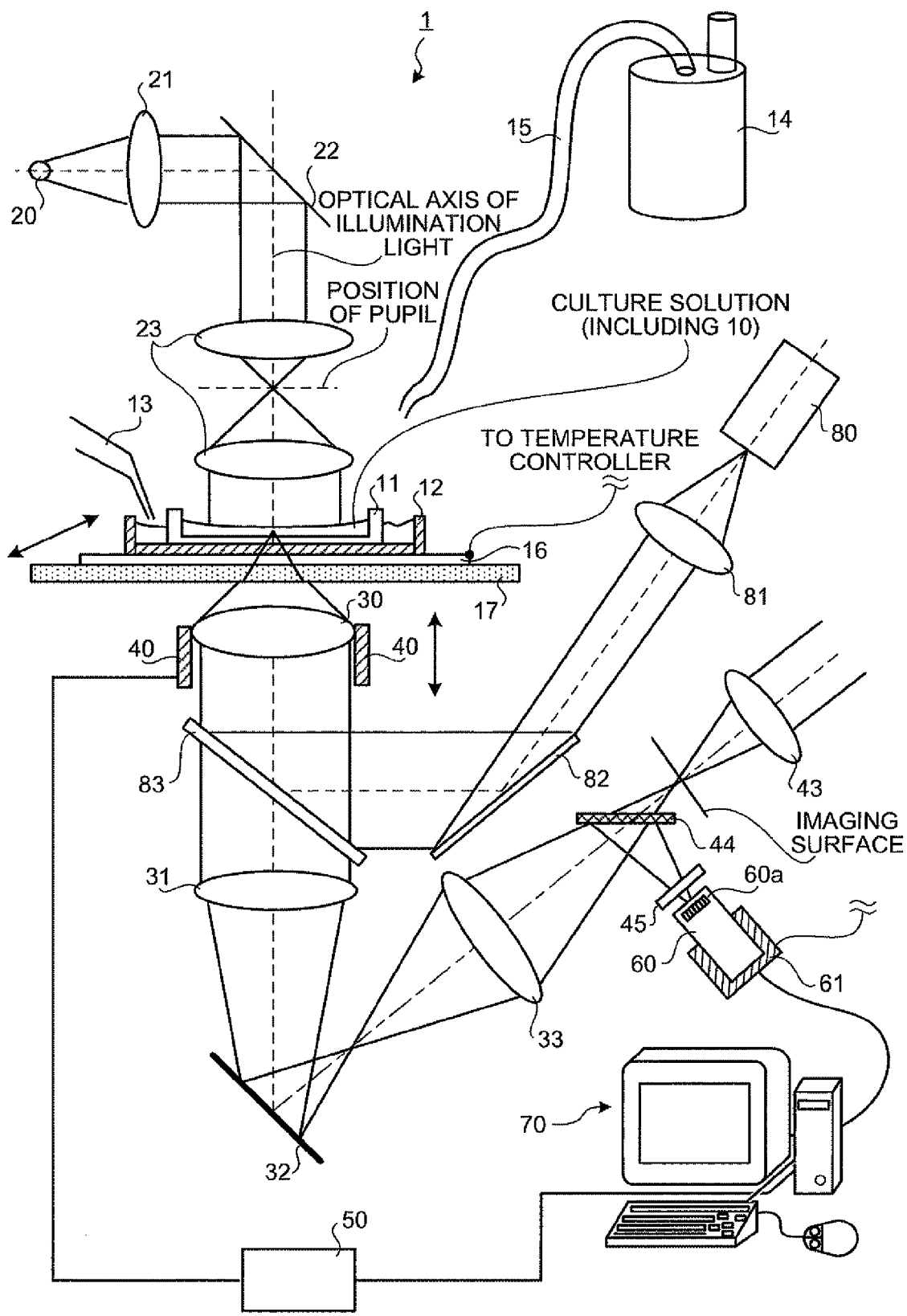
FIG. 20 is a view showing a specific example of the configuration of the focal position determining apparatus 1 according to a second embodiment.

FIG. 20 is a view showing one specific example of the structure of the focal position determining apparatus 1 according to the second embodiment. The focal position determining apparatus 1 shown in FIG. 20 has a structure with an inverted microscope as a base, and is used for observing simultaneously luminescence and fluorescence of a living cell that emits feeble light. In simultaneously observing fluorescence and luminescence, the focal position determining apparatus 1 determines the focal position of the objective lens 30 focused on the observed target region 10a in the specimen 10 at the time of setting the specimen 10 such as a living cell or tissue. As shown in FIG. 20, the focal position determining apparatus 1 has an exciting optical system including an exciting light irradiating unit (exciting light source) 80, a collimator lens 81, a deflection mirror 82 and a dichroic mirror 83.

When the specimen 10 is present in the air (when the specimen 10 is not immersed into liquid such as culture solution), the focal position determining apparatus 1 shown in FIG. 20 employs the objective lens 30 having the numerical aperture (NA) of about 0.9, while when the specimen 10 is immersed into liquid, it employs the objective lens having the numerical aperture of not less than 1.0. The specimen 10 is dyed beforehand with Rohdamine Green (RhG) that is a fluorescent pigment (fluorescent material). Instead of Rhodamine Green, usable fluorescent materials include TMR (Tetramethylrhodamine), 5-Tamra (5-carboxytetramethylrhodamine), FITC (Fluorescein-i-sothiocyanate), TOTO1, Acridine-Orange, Texas-Red, etc.

The exciting light irradiating unit 80 is a gas laser (e.g., argon laser, helium-neon laser (He—Ne laser), etc.) emitting laser beam having a wavelength in a visible light region. Specifically, the exciting light irradiating unit 80 is an argon laser having a wavelength of 488 nm and output of 10 mW. When the specimen 10 is dyed with TMR that is a fluorescent material, the argon laser having a wavelength of 514.5 nm is used as the exciting light irradiating unit 80 in order to excite the TMR. When the specimen 10 is dyed with 5-Tamra that is a fluorescent material, the He—Ne laser having a wavelength of 543.5 nm is used as the exciting light irradiating unit 80 in order to excite the 5-Tamra.

The collimator lens 81 converts the laser beam emitted from the exciting light irradiating unit 80 into annular parallel flux having a beam width.

The deflection mirror 82 deflects the optical axis of the laser beam, which is converted into the parallel flux by the collimator lens 81.

The dichroic mirror 83 is specifically a switching dichroic mirror, and introduces the laser beam deflected by the deflection mirror 82 to the objective lens 30. The switching dichroic mirror has a spectral characteristic of reflecting light having an oscillation wavelength of the exciting light source 80 and transmitting the spectrum of the fluorescent signal and the luminescent signal. The dichroic mirror 83 is housed in a holder (not shown), so that it is replaceably arranged according to the oscillation wavelength of the laser beam. If it is unnecessary to change the wavelength of the laser beam emitted from the exciting light irradiating unit 80, an ordinary dichroic mirror, not the switching dichroic mirror, may be used as the dichroic mirror 83.

In the focal position determining apparatus 1 shown in FIG. 20, the fluorescence and luminescence emitted from the specimen 10 reaches the dichroic mirror 83 through the objective lens 30. The fluorescence and luminescence having reached the dichroic mirror 83 transmits the dichroic mirror 83, and are reflected by the switching mirror 44 through the relay lens 31 and the relay lens 33 to be focused on the imaging device 60*a* on the light-receiving surface of the CCD camera 60. When the switching mirror 44 is removed from the optical path, the fluorescence and luminescence emitted from the specimen 10 reaches the ocular lens 43. Accordingly, an operator can directly observe the image of the specimen 10.

Next, another specific example of the focal position determining apparatus 1 according to the second embodiment will be explained in detail with reference to FIG. 21. FIG. 21 is a view showing another specific example of the focal position determining apparatus 1 according to the second embodiment.

Figure 21:
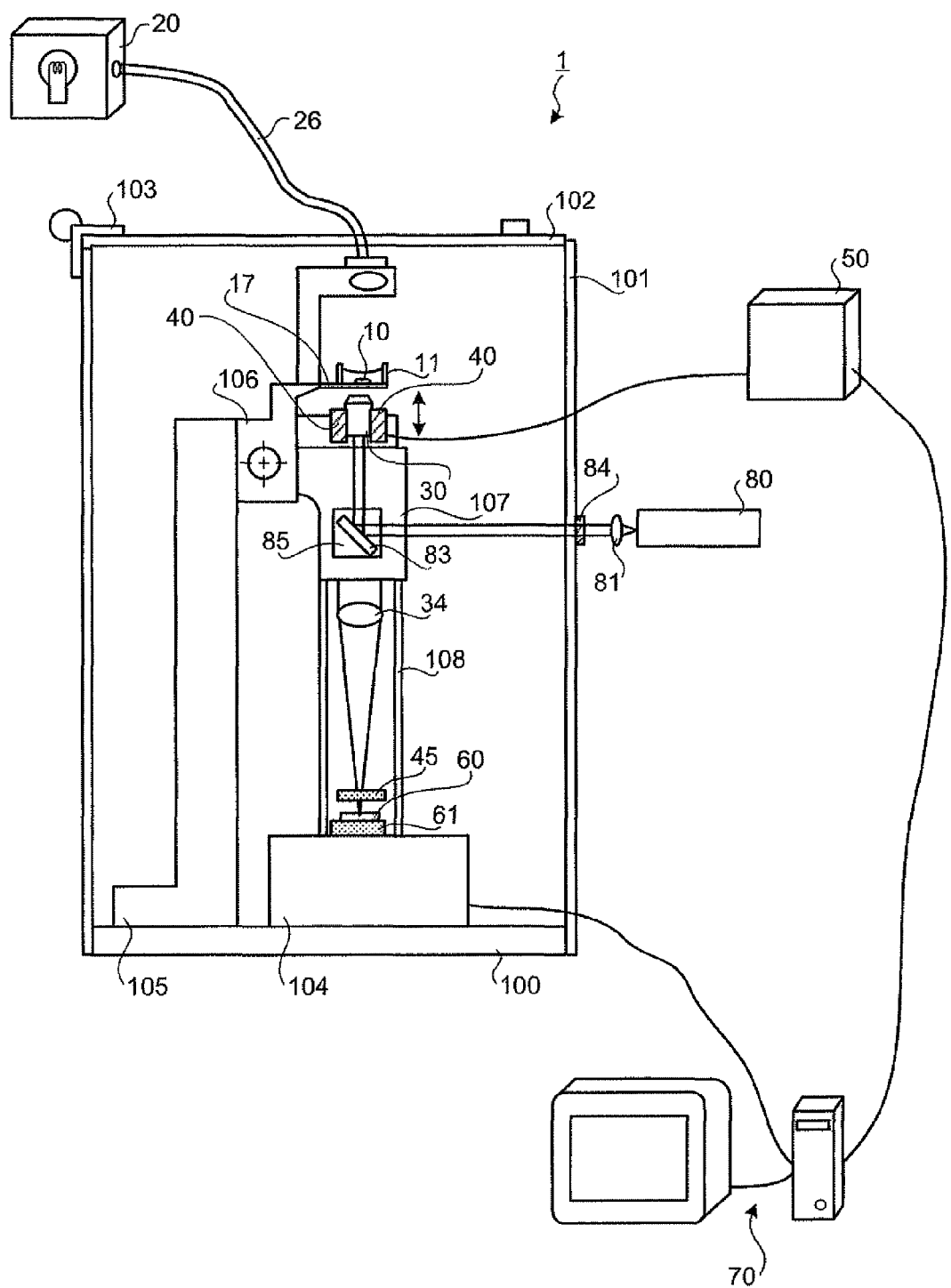
FIG. 21 is a view showing another specific example of the configuration of the focal position determining apparatus 1 according to the second embodiment.

As shown in FIG. 21, the main body (portion of the optical system) of the focal position determining apparatus 1 is fixed on a main body rack 106. The main body rack 106 is vertically movable. The main body rack 106 is attached to a column 105. The column 105 is fixed on a bottom plate 100. The observation optical system and the CCD camera 60, etc. in the focal position determining apparatus 1 are housed in a lens barrel. The lens barrel is composed of a lens barrel upper part 107 and a lens barrel lower part 108 connected to the lens barrel upper part 107. The lens barrel upper part 107 is fixed to the main body rack 106. The lens barrel lower part 108 is fixed to a base rack 104. The lens barrel is attached so as to be vertically movable. The base rack 104 is fixed on the bottom plate 100. The main body of the focal position determining apparatus 1 is enclosed by a light-shielding box 101 having light shielding property. The light-shielding box 101 is fixed to the bottom plate 100. A light-shielding lid 102 is mounted to the upper surface of the light-shielding box 101. One end of the light-shielding lid 102 is coupled to the light-shielding box 101 with a hinge 103 in order to make the lid openable and closable.

The specimen container 11 having the specimen 10 put therein is set on the specimen stage 17. As shown in FIG. 22, the specimen container 11 may be put into the water tank 12 to be set on the specimen stage 17.

Returning back to FIG. 21, a halogen lamp, metal halide lamp or the like is used as the light irradiating unit 20. Light emitted from the light irradiating unit 20 is irradiated to the specimen container 11 containing the specimen 10 on the specimen stage 17 through an optical fiber 26.

In the observation optical system, the deflection mirror 32 is not used, and instead, a relay lens 34 for imaging the image (image of the specimen 10) formed by the objective lens 30 is arranged at the lens barrel lower part 108 as shown in the figure.

Figure 22:
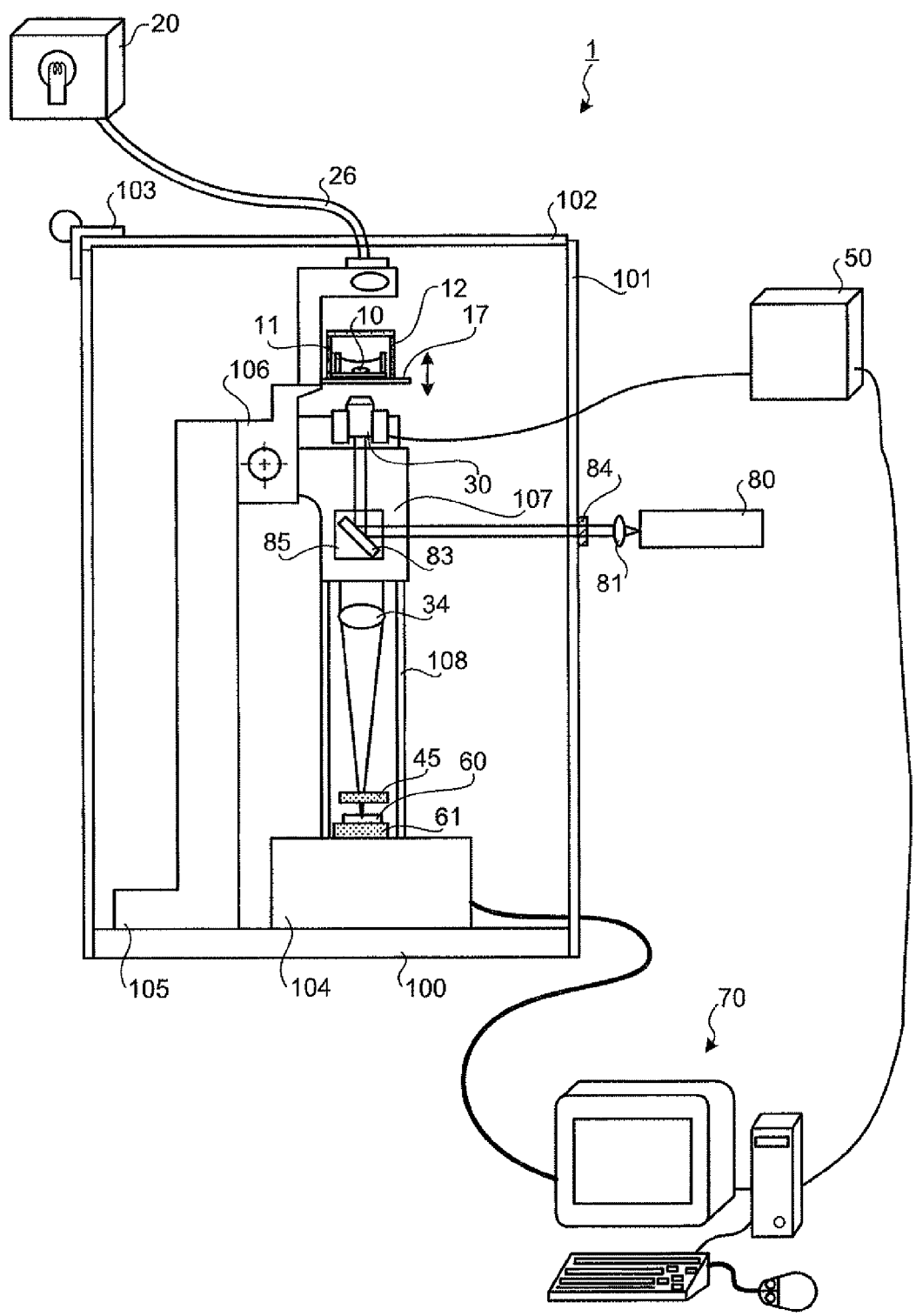
FIG. 22 is a view showing another specific example of the configuration of the focal position determining apparatus 1 according to the second embodiment.

As shown in FIG. 22, the focal position determining apparatus 1 shown in FIG. 21 may have a stage z-axis moving mechanism for moving the specimen stage 17 along the z axis as the focal position changing unit 40, instead of the objective lens z-axis moving mechanism. In FIG. 22, a Z-axis moving stage provided with the stage z-axis moving mechanism is mounted to the main body rack 106. The Z-axis moving stage is mounted below the XY specimen stage, which is movable in XY direction, so as to hold the XY specimen stage. The specimen container 11 is arranged above the Z-axis moving stage, whereby the specimen container 11 vertically moves with the vertical movement of the Z-axis moving stage, The Z-axis moving stage vertically moves by a rack-and-pinion mechanism. The operation of the rack-and-pinion mechanism is executed by turning a knob (not shown) of the rack-and-pinion mechanism by a stepping motor. The drive of the stepping motor is controlled by a computer. Thus, the operation same as that when the objective lens 30 is vertically moved can be achieved. The Z-axis moving stage may manually be moved vertically. The operation of the rack-and-pinion mechanism may be executed by turning a knob (not shown) of the rack-and-pinion mechanism.

Returning back to FIG. 21 again, the CCD camera 60 is arranged in such a manner that the center of the light-receiving surface substantially matches the optical axis. The fluorescence and luminescence emitted from the specimen (living cell) 10 transmits the dichroic mirror 83, and converges onto the light-receiving surface of the CCD camera 60 through the relay lens 34. The infrared ray cut filter 45 attached at the front surface of the CCD camera 60 is removed before starting the focal position determining apparatus 1 in order to take out infrared ray. The CCD camera 60 is connected to the information processing device 70, which processes the output signal from the CCD camera 60, via a cable.

The information processing device 70 describes and analyzes the luminescent image from the output signal from the CCD camera, measures the change over time of the intensity of the luminescence, and analyzes the output signal. The information processing device 70 further operates the CCD camera by the control unit 70*a* in order to receive the fluorescence and luminescence from the specimen 10 after the focal position of the objective lens 30 is focused on the observed target region 10*a* in the specimen 10.

The exciting light irradiating unit 80 is an argon laser having a wavelength of 488 nm and output of 10 mW, and is arranged at the outside of the light-shielding box 101 as shown in the figure. A laser inlet port 84 through which the optical fiber is inserted is formed to the light-shielding box 101. The laser beam emitted from the exciting light irradiating unit 80 passes through the collimator lens 81 and propagates in the optical fiber. The propagated laser beam reaches the dichroic mirror 83. The laser beam reaching the dichroic mirror 83 is reflected by the dichroic mirror 83 to be incident on the objective lens 30 from below. The incident laser beam is converged to be irradiated onto the specimen 10. The dichroic mirror 83 is housed in a holder 85, so that it is replaceably mounted according to the oscillation wavelength of the laser beam.

In the focal position determining apparatus 1 shown in FIG. 21, the fluorescence and luminescence emitted from the specimen 10 reaches the dichroic mirror 83 through the objective lens 30. The fluorescence and luminescence having reached the dichroic mirror 83 passes the dichroic mirror 83 to be focused on the imaging device 60*a* on the light-receiving surface of the CCD camera through the relay lens 34.

The explanation of the structure of the focal position determining apparatus 1 according to the second embodiment is now ended.

Next, the focal position determining process and the focal position re-determining process executed by the focal position determining apparatus 1 according to the second embodiment are the same as those explained in the first embodiment, so that the explanation thereof is omitted.

As explained above, the focal position determining apparatus 1 according to the second embodiment further includes the exciting optical system. In the focal position determining apparatus 1 according to the second embodiment, irradiation light is irradiated to the living cell from the light source 20. The focal position determining apparatus 1 repeatedly moves the objective lens 30 along the optical axis by the objective lens z-axis moving mechanism by a predetermined amount, and every time the objective lens 30 is moved, the focal position determining apparatus 1 measures the focal position of the objective lens 30 by the focal position measuring unit 50, images the living cell under the illumination by the CCD camera, and calculates the contrast of the imaged image by the feature data calculating unit 70a1. The focal position determining apparatus 1 then selects two maximum contrasts, among the accumulated plural contrasts obtained by repeatedly moving the objective lens 30, by the focal position selector 70a2, and acquires the focal positions of the objective lens 30 when the images corresponding to the selected contrasts are imaged from the accumulated plural focal positions obtained by repeatedly moving the objective lens 30. Then, the focal position determining apparatus 1 determines, by the focal position determining unit 70a3, the central position (the position at approximately the center) between two focal positions as the focal position of the objective lens 30 focused on the observed target region 10a in the living cell based on the acquired focal position, and moves the objective lens 30 by the objective lens z-axis moving mechanism so as to adjust the focal position of the objective lens 30 to the determined focal position. Accordingly, when the fluorescence and the luminescence of the observed target region 10a are simultaneously observed with the specific region in the living cell defined as the observed target region 10a, the focal position of the objective lens 30 focused on the observed target region 10a can be determined at the time of setting the living cell, with the result that the focal position of the objective lens 30 can be focused on the observed target region 10a.

Some of the techniques for measuring the ATP amount in the living cell as simultaneously observing the luminescent image and the fluorescent image of the living cell by using the focal position determining apparatus 1 according to the second embodiment will be explained below. Since the luminescent reaction (intensity of the luminescence) of luciferase depends upon the ATP amount, the quantification of the ATP by utilizing the luminescent reaction of luciferase has conventionally been executed. In a field of biotechnology, clinical examination, food hygiene, etc., an ATP amount in a cell has been measured with the use of luciferase. An ATP (adenosine-3-phosphoric acid) is a supply source of energy in a cell, and it is a material deeply related to a life phenomenon. On the other hand, luciferase in a firefly catalyzes the reaction for generating oxiluciferin, $CO_2$, AMP, and pyrophosphoric acid under the presence of ATP, $O_2$ and $Mg^{2+}$ with D-luciferin defined as a luminescent substrate, and emits light by this reaction.

The measurement of the ATP amount in a living cell is generally performed in steps (1A) to (1C) described below (H. J. Kennedy, A. E. Pouli, E. K. Ainscow, L. S. Jouaville, R. Rizzuto, G. A. Rutter, "Glucose generates sub-plasma membrane ATP microdomains in single islet β-cells", Journal of Biological Chemistry, vol. 274, pp. 13281-13291, 1999).

(1A) A cell or germ is dissolved to extract an ATP.
(1B) The extract is added to reaction solution containing luciferine and luciferase.
(1C) The amount of luminescence produced from the reaction solution having the extract added thereto is measured, whereby the ATP in the cell is quantified.

An ATP amount in a cell is generally measured by the steps (2A) to (2C) described below.

(2A) A luciferase gene is transduced to a cell for expression.
(2B) Luciferine is added to culture solution containing the cell.
(2C) The amount of luminescence produced from the culture solution to which luciferine is added is detected so as to quantify the ATP in the cell.

An ATP amount at a predetermined region (specifically, mitochondria) in a living cell is measured over time by the steps (3A) to (3B) described below (H. J. Kennedy, A. E. Pouli, E. K. Ainscow, L. S. Jouaville, R. Rizzuto, G. A. Rutter, "Glucose generates sub-plasma membrane ATP microdomains in single islet β-cells", Journal of Biological Chemistry, vol. 274, pp. 13281-13291, 1999).

(3A) A mitochondria localization signal gene is fused to luciferase gene, and the fusion gene is transduced to a cell. The fusion gene transduced to the cell is obtained by fusing a fluorescence-related gene that expresses fluorescent protein in addition to a transfer base sequence and a luminescence-related gene.

(3B) The amount of luminescence from the cell is measured over time on the presupposition that the luciferase is localized in mitochondria in the cell, whereby the variation over time in the ATP amount in the mitochondria in the cell is measured. Specifically, a fluorescent image of the cell to which the fusion gene is transduced is imaged, and it is determined whether luminescent protein is localized or not at the predetermined region based on the obtained fluorescent image. When it is determined that the luminescent protein is localized, the amount of luminescence from the cell is detected. Accordingly, it can be determined whether luminescent protein is localized or not at the predetermined region in the cell. Specifically, the localization of luminescent protein in the living cell to which the fusion gene is transduced is confirmed, and further, the amount of luminescence from the cell is measured. Further, it can be confirmed that the measured amount of luminescence is from the predetermined region.

When plural living cells to which the fusion gene is transduced are present within the range of an imaging field, plural fluorescent images and luminescent images of the cell are imaged, and it is determined for every cell whether luminescent protein is localized or not at the predetermined region based on the fluorescent image. Then, the imaged fluorescent image and the imaged luminescent image are overlapped with each other so as to select the cell to be measured among the cells in which luminescent protein is determined to be localized, whereby the amount of luminescence from the selected cell is measured. Thus, an individual cell is identified among plural cells, and the amount of luminescence from a predetermined region of a single cell can be measured as separated from the other cells. Moreover, the fluorescent image and the luminescent image are simultaneously obtained, whereby the localization of luminescent protein in the cell to be measured and the intensity of luminescence emitted from the cell can simultaneously be obtained. Therefore, it makes it possible to perform an analysis from which an influence caused by the difference in a physiological condition of an individual cell due to a transduction efficiency of a gene or a cell cycle is eliminated. As one example, it may be determined whether luminescent protein is localized or not at the predetermined region after the fluorescent image is taken, and when it is determined that the luminescent protein is localized, a luminescent image may be taken. The determination of the localization may be performed after a fluorescent image and a luminescent image are imaged.

The explanation of the focal position determining apparatus 1 according to the second embodiment is now ended.

Third Embodiment

1. Basic Principle of Invention

Firstly, a basic principle of the biological specimen imaging method and the biological specimen imaging apparatus according to the present invention will be explained in detail. The present invention images a biological specimen, which is stored in a storing section of a substrate having plural storing sections and emits a feeble light, through an objective lens. In the present invention, any one of the substrate and objective lens or both is moved until the desired storing section falls within the field of view of the objective lens, any one of the focal position of the objective lens at the near point and the focal position of the objective lens at the far point or both is measured, the focal position of the objective lens, which is focused on an observed target region in the biological specimen stored in the desired storing section is determined based on the measured focal position, the focal position of the objective lens is adjusted to the determined focal position, and the biological specimen is imaged through the objective lens so as to acquire the luminescent image of the biological specimen. Thus, the biological specimen stored in the storing sections of the substrate (e.g., wells of a microplate) can quickly and correctly be imaged.

In the present invention, when any one of the substrate and objective lens or both is moved until the desired storing section falls within the field of view of the objective lens, the position of any one of the substrate and the objective lens or both at the moving destination may be measured, and moving destination positional information relating to the measured position at the moving destination may be stored as associated with storing section identifying information for identifying the desired storing section. By virtue of this, if the storing section identifying information corresponding to the desired storing section is stored when any one of the substrate and objective lens or both is moved until the desired storing section falls within the field of view of the objective lens, any one of the substrate and objective lens or both can suitably be moved based on the moving destination positional information stored as associated with the storing section identifying information.

Further, the present invention executes: (1) moving any one of the substrate and objective lens or both until the desired storing section falls within the field of view of the objective lens, (2) irradiating light to the biological specimen, (3) changing the focal position of the objective lens, (4) measuring the changed focal position, (5) imaging the biological specimen, to which the light is irradiated, at the changed focal position, (6) calculating feature data, which features the imaged image, based on the imaged image, (7) repeatedly executing "changing the focal position", "measuring the focal position", "imaging the specimen", and "calculating the feature data" described above, (8) selecting at least one focal position from the plural focal positions stored by the repeated execution based on the plural feature data pieces stored by the repeated execution, (9) determining the focal position of the objective lens focused to the observed target region in the biological specimen stored in the desired storing section based on the selected focal position, (10) adjusting the focal position of the objective lens to the determined focal position, and (11) imaging the biological specimen through the objective lens so as to acquire the luminescent image of the biological specimen. With these processes, the biological specimen stored in the storing sections of the substrate (e.g., wells of a microplate) can quickly and correctly be imaged.

In the present invention, in the process of (1), when any one of the substrate and objective lens or both may be moved until the desired storing section falls within the field of view of the objective lens, the position of any one of the substrate and the objective lens or both at the moving destination may be measured, and moving destination positional information relating to the measured position at the moving destination may be stored as associated with storing section identifying information for identifying the desired storing section. By virtue of this, if the storing section identifying information corresponding to the desired storing section is stored when any one of the substrate and objective lens or both is moved until the desired storing section falls within the field of view of the objective lens, any one of the substrate and objective lens or both can suitably be moved based on the moving destination positional information stored as associated with the storing section identifying information.

2. Device Structure

A specific example of the focal position determining apparatus 1, which is a biological specimen imaging apparatus, according to the third embodiment will be explained in detail with reference to FIGS. 33 to 39. The explanation overlapped with the explanation in the first and second embodiments described above might be omitted.

Figure 33:
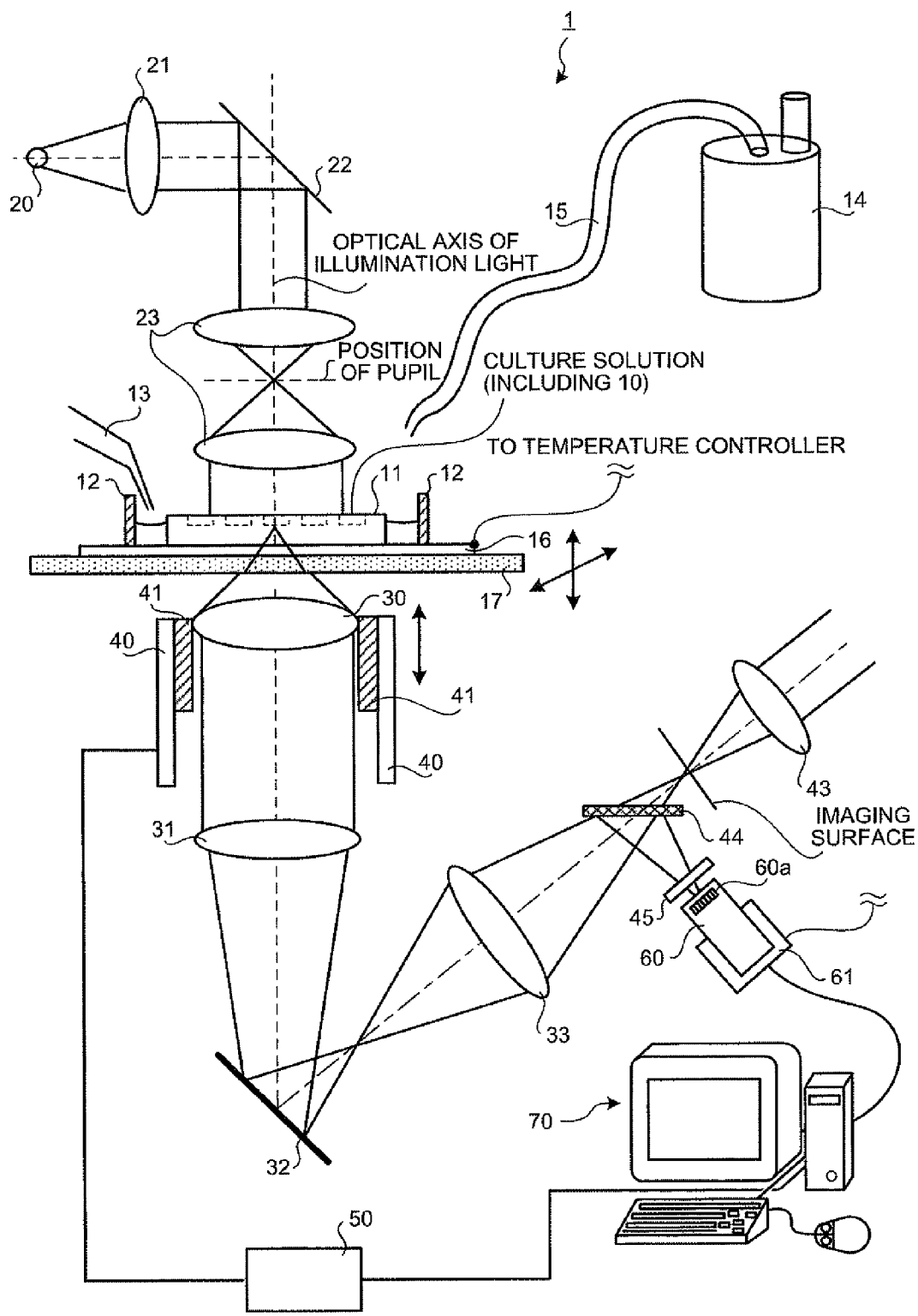
FIG. 33 is a view for showing one specific example of the configuration of the focal position determining apparatus 1 that serves as a biological specimen imaging apparatus according to a third embodiment.
Figure 34:
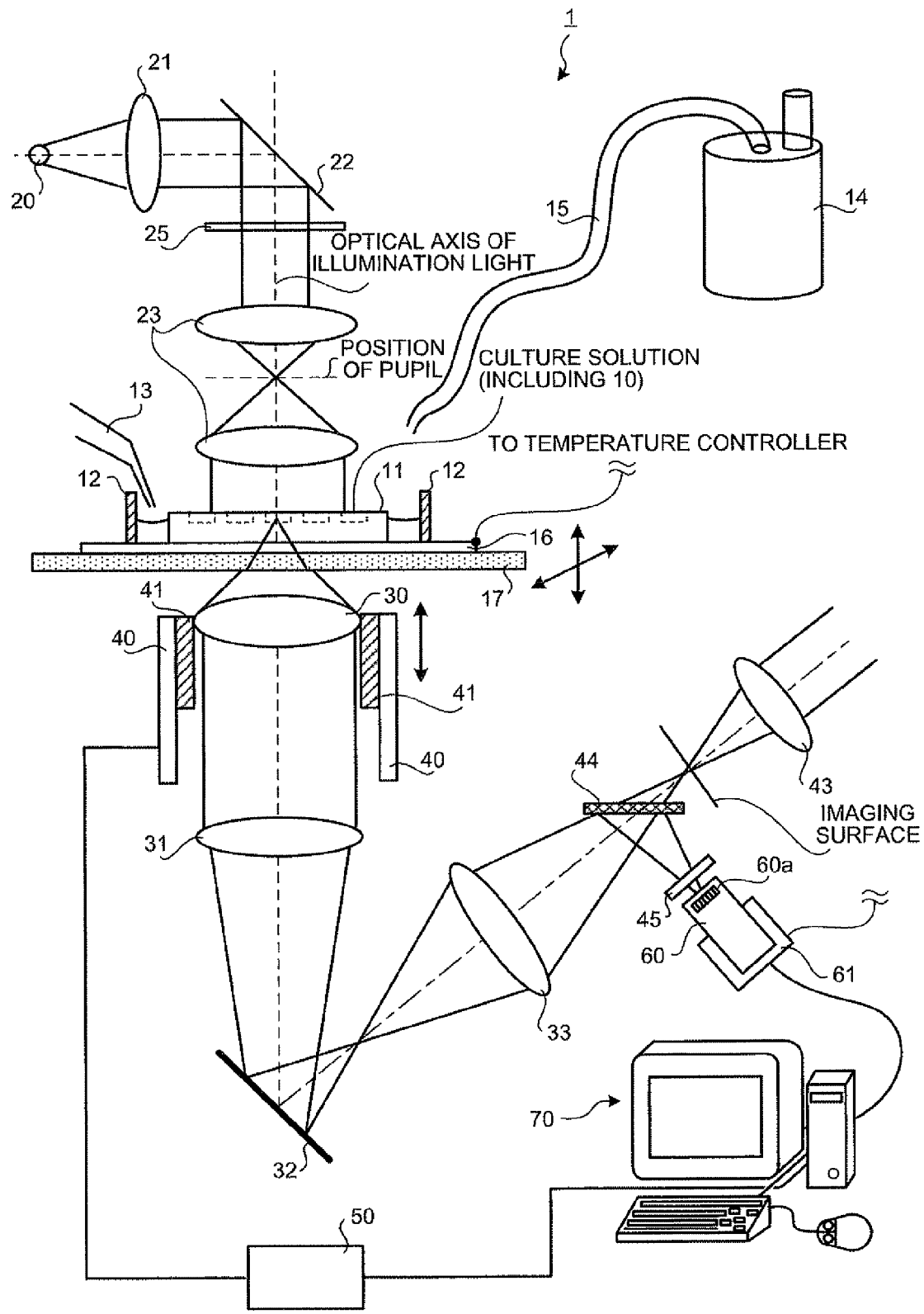
FIG. 34 is a view for showing one specific example of the configuration of the focal position determining apparatus 1 that serves as a biological specimen imaging apparatus according to a third embodiment.
Figure 35:
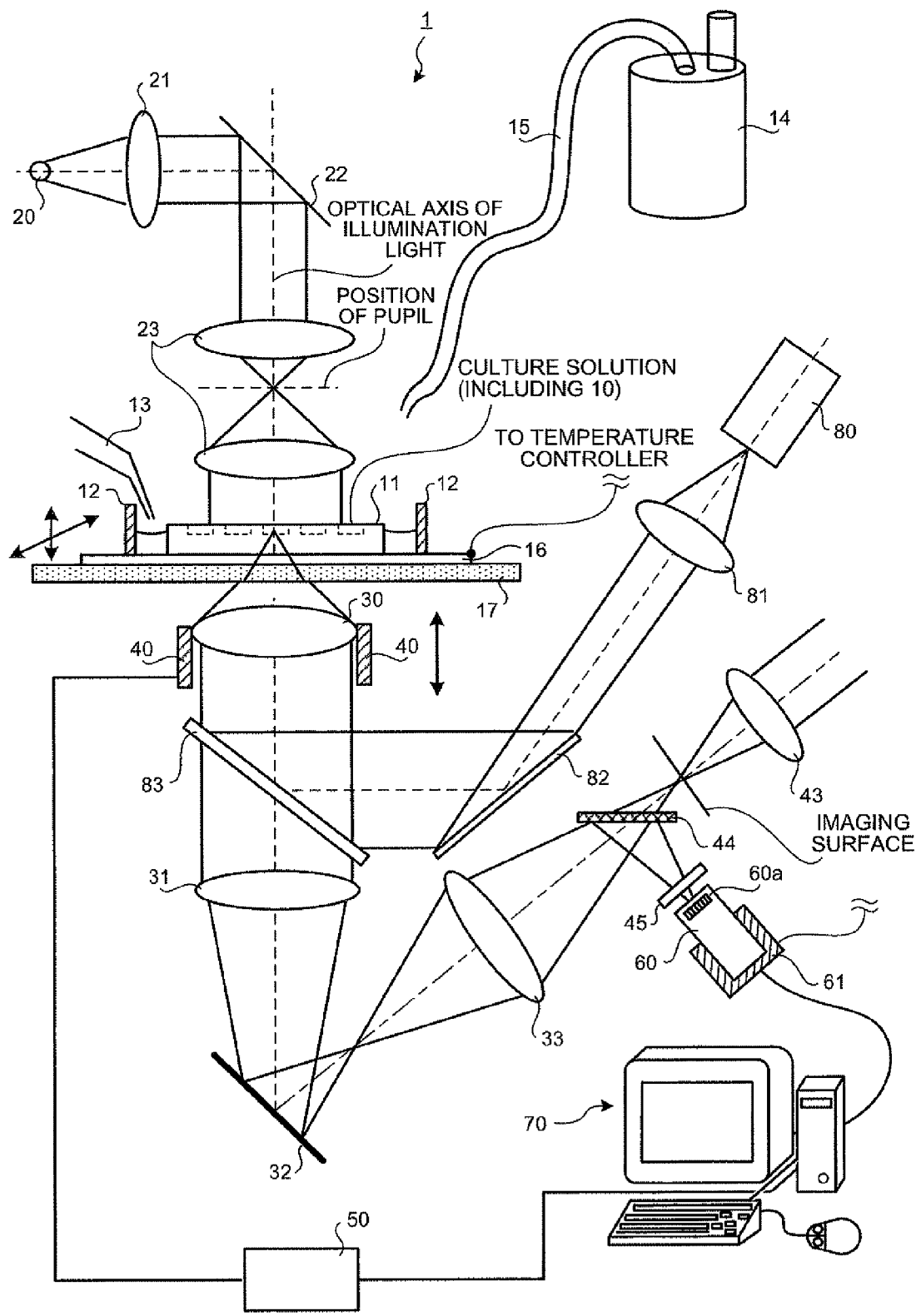
FIG. 35 is a view for showing one specific example of the configuration of the focal position determining apparatus 1 that serves as a biological specimen imaging apparatus according to a third embodiment.

FIGS. 33 and 34 are views showing one specific example of the focal position determining apparatus 1, which is the biological specimen imaging apparatus, according to the third embodiment. The focal position determining apparatus 1 according to the third embodiment shown in FIGS. 33 and 34 is obtained by changing the structure of the specimen container 11, water tank 12 and stepping motors mounted at the predetermined positions of the specimen stage 17 in the focal position determining apparatus 1 according to the first embodiment shown in FIGS. 13 and 17. FIG. 35 is a view for showing one specific example of the configuration of the focal position determining apparatus 1, which is the biological specimen imaging apparatus, according to the third embodiment. The focal position determining apparatus 1 according to the third embodiment shown in FIG. 35 is obtained by changing the structure of the specimen container 11, water tank 12 and stepping motors mounted at the predetermined positions of the specimen stage 17 in the focal position determining apparatus 1 according to the second embodiment shown in FIG. 20.

In FIGS. 33, 34 and 35, the specimen container 11 is specifically a microplate having plural wells. The bottom surface (at least the bottom surface corresponding to the wells) of the microplate is flat, and optically transparent (that can be handled by a normal objective lens). The water tank 12 is not provided with the bottom surface as illustrated, and configured to enclose the specimen container 11. The number of the stepping motor (not shown) is three, wherein each of the stepping motors is mounted to the predetermined position of the specimen stage 17 so as to be orthogonal to one another (90° direction). The specimen stage 17 is movable in the optical axis direction (z axis direction) or in the direction (e.g. r x-direction or y-direction) orthogonal to the optical axis direction from the position where the stage is mounted, by the driving forces of the stepping motors.

Figure 36:
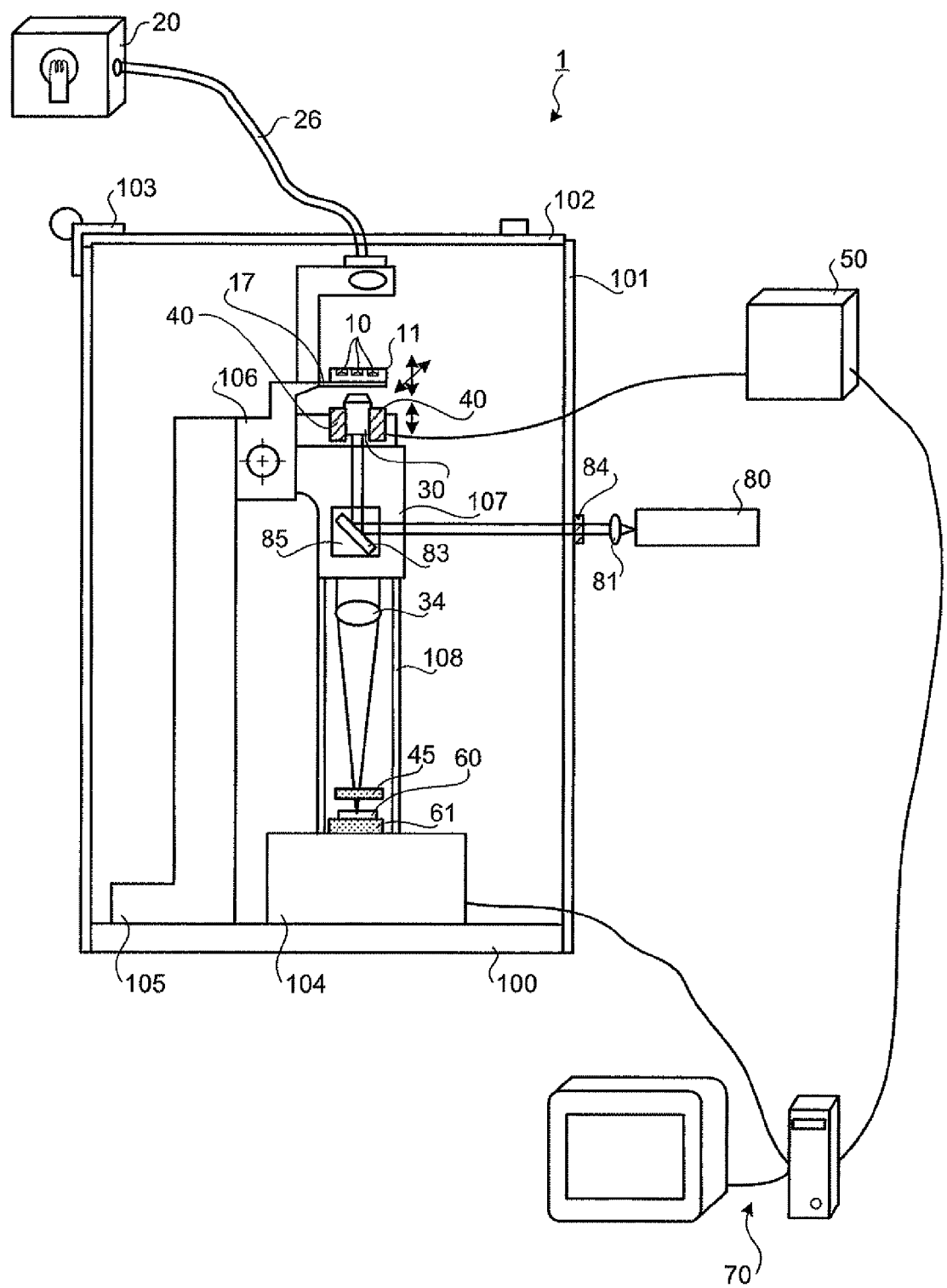
FIG. 36 is a view for showing one specific example of the configuration of the focal position determining apparatus 1 that serves as a biological specimen imaging apparatus according to a third embodiment.

FIG. 36 is a view for showing one specific example of the configuration of the focal position determining apparatus 1, which is the biological specimen imaging apparatus, according to the third embodiment. The focal position determining apparatus 1 according to the third embodiment shown in FIG. 36 is obtained by changing the specimen container 11 and the specimen stage 17 in the focal position determining apparatus 1 according to the second embodiment shown in FIG. 21.

In FIG. 36, the specimen container 11 is specifically a microplate having plural wells. The bottom surface (at least the bottom surface corresponding to the wells) of the microplate is flat, and optically transparent (that can be handled by a normal objective lens). The specimen stage 17 has a stage XYZ-axis moving mechanism for moving the stage along the optical axis (Z axis) or in the direction (XY direction) orthogonal to the optical axis.

Figure 37:
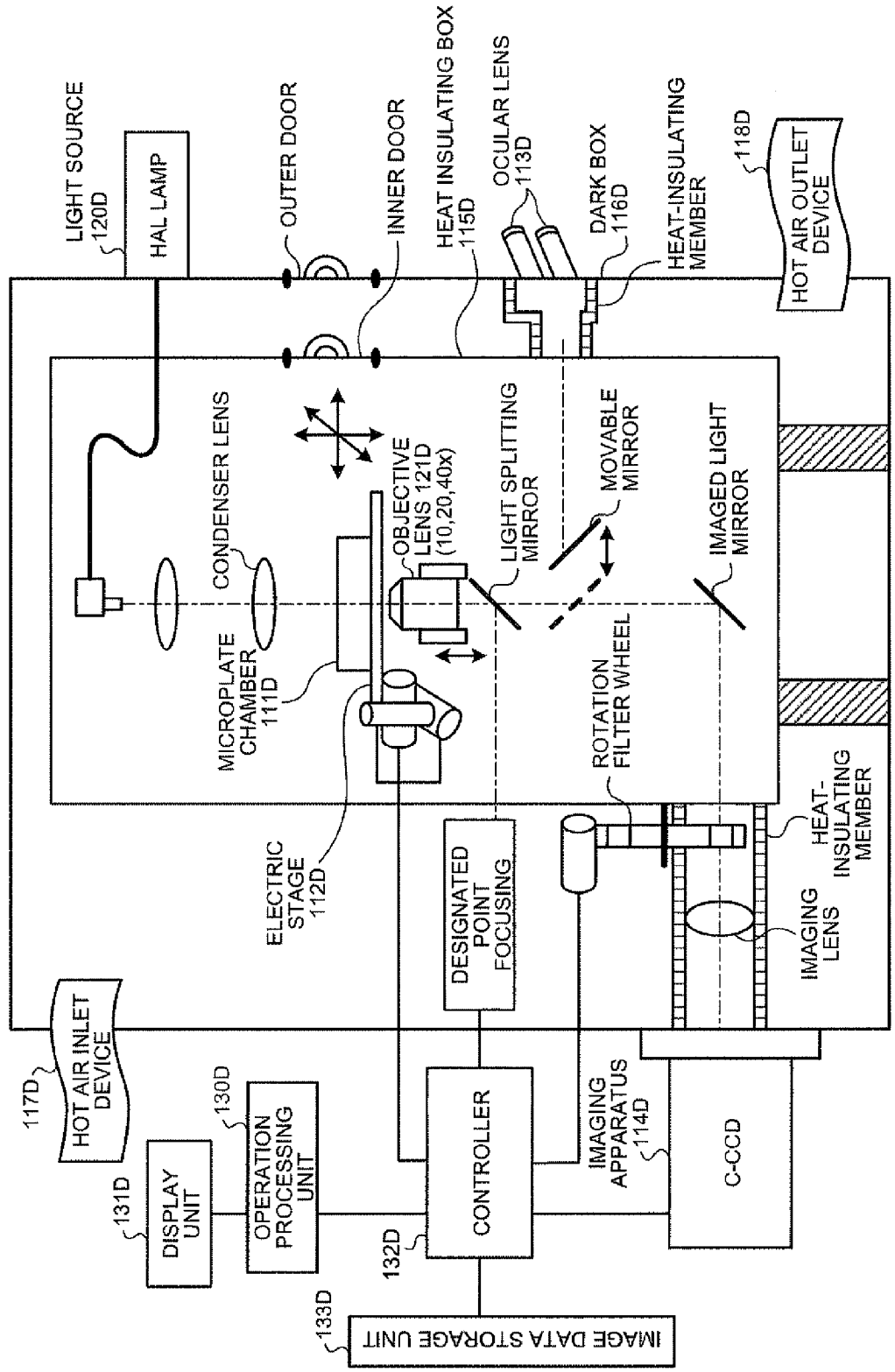
FIG. 37 is a view for showing one specific example of a configuration of an examination system according to the third embodiment.

FIG. 37 is a view for showing one specific example of a configuration of an examination system according to the third embodiment. The examination system shown in FIG. 37 has a high throughput configuration suitable for exhaustively analyzing a specimen in each of the plural containers (particularly, a large number of wells of the microplate).

Figure 38:
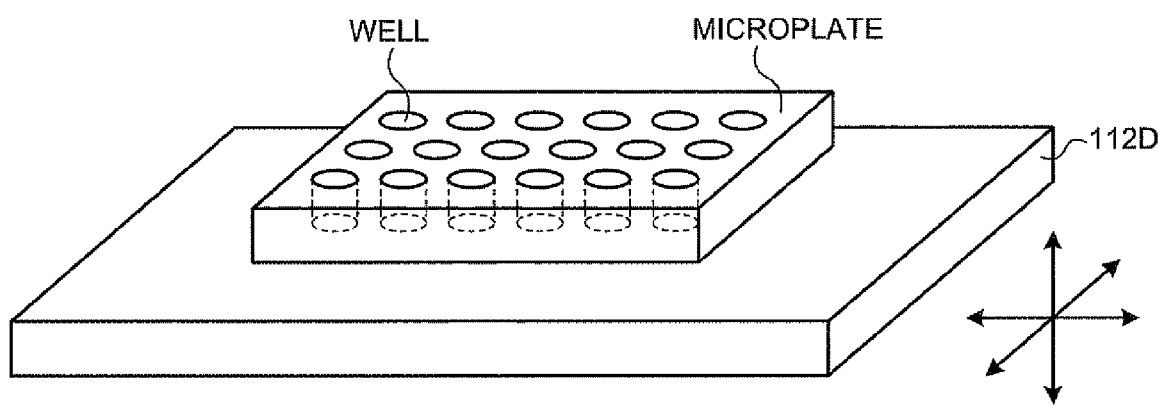
FIG. 38 is a view for showing one specific example of a microplate used in the examination system according to the third embodiment.

In the examination system shown in FIG. 37, a microplate chamber 111D that stores the microplate shown in FIG. 38 having a large number of wells arranged in a matrix is detachably fixed onto an electric stage 112D.

An illumination system for performing a bright field observation is arranged above the microplate chamber 111D. On the other hand, an observation system for observing an image of a specimen, such as a cell stored in each well of the microplate, with a bright field with naked eyes through an ocular lens 113D and an imaging system for imaging the specimen with a dark field with an imaging apparatus 114D are arranged below the microplate chamber 111D.

The specimen containing a cell or the biological tissue stored in the well has a low density to a degree in which the individual cell can be recognized, i.e., they are not overlapped with each other on an optical path. This is a difference from the measurement based on the number of cells that are overlapped with one another to have a high density, like a system, such as a luminometer, for analyzing the light emission amount of the whole well.

The microplate chamber 111D and the lens components of the illumination system are stored in a heat insulating box 115D that keeps the biological specimen, such as cell, antigen, or antibody, to have a temperature by which the activity can be maintained. The various lens components of the observation system and the imaging system are arranged outside of the heat insulating box 115D and protected by a heat insulating member (e.g., aluminum film, ceramic cylinder) having light shielding property.

The electric stage 112D is movable in the optical axis direction (Z axis) or in the direction (XY direction) orthogonal to the optical axis direction by appropriately driving three motors through the control of a controller 132D. An objective lens Z-axis driving mechanism that moves an objective lens 121D in the optical axis (Z axis) direction is provided to the objective lens 121D.

The light emitted from the specimen in the microplate chamber 111D passes through the objective lens 121D that is set to have a suitable optical condition, then, is reflected on an imaging mirror at the lowermost part, and is transmitted to the imaging apparatus 114D through an imaging lens. On the other hand, a movable mirror shown in FIG. 37 is advanced to or retreated from the optical path so as to execute the selective observation through the ocular lens 113D, whereby the light loss, which is caused when the feeble light from the specimen is detected, can be prevented as much as possible, and a high-reflective mirror that is optimum for the observation can be employed for the ocular lens 113D. The movable mirror may be driven with an automatic-switching system or with a manual operation system by means of a slide bar.

The heat insulating box 115D is further stored in a dark box 116D for blocking the influence from the external environment (light, ambient temperature, moisture, oxygen, etc.).

Thus, the whole system has a double structure. The dark box 116D has, at the position selected suitably considering the internal air-conditioning efficiency, a hot air inlet device 117D (at the left wall at the upper part of the dark box in FIG. 37) and a hot air outlet device 1118D (at the right wall at the upper part of the dark box in FIG. 37). Further, an inside door and an outside door are provided to the heat insulating box 115D and the dark box 116D so as to allow the replacement of the microplate placed onto the electric stage 112D.

A light source (halogen lamp in FIG. 37) 120D for the illumination system and an imaging apparatus (C-CCD camera in FIG. 37) 114D for the imaging system are mounted outside of the dark box 116D, so as to avoid a thermal trouble. The imaging lens for the imaging apparatus 114D and a rotating filter wheel for selecting a wavelength are arranged between the heat insulating box 115D and the dark box 116D.

As shown in FIG. 37, a laser detecting mechanism, which performs a focusing on a designated point with an infrared ray or visible light, may be mounted in order to strictly perform the observation and imaging in the microplate. When the designated point is focused, a light splitting mirror is arranged, for example, below the electric stage 112D in order to measure the reflection from the bottom surface of the microplate. The focusing on the designated point described above is not an essential constituent except for the case in which a fine image resolution is demanded. As for the light splitting mirror, it is preferable to minimize the light loss from the specimen by a dichroic mirror by means of an infrared ray. In the case of using a visible light, it is preferable to use a half mirror having a minimum reflectivity by which the focusing is possible or the aforesaid movable mirror, in order to prevent the light loss.

The image data transmitted from the imaging apparatus 114D is subject to a statistical analysis or a shape analysis by an operation processing unit 130D, and displayed onto a display unit 131D. Thus, a variety of analyses, such as the analysis performed for every well in a time-series manner or the comparison between the wells, can exhaustively executed. The numerical data can graphically be displayed onto the display unit 131D with a time series curve. The present examination system is characterized in that the image data is stored in an image data storage unit 133D connected to the controller 132D, and the image data stored in the image data storage unit 133D can be called and reproduced as a image, onto the display unit 131D according to need. Therefore, the present examination system can execute a recall function in which the data portion (measured point or data area) of the interested data of the graphical display data pieces is designated by appropriate designating means (mouse pointer, touch pen, keyboard, etc.), whereby the time series data of this portion is reproduced in a static image or a moving image. According to the present examination system, only the image data can be displayed onto the display unit 131D or the combination of the image data and the numerical data can be displayed onto the display unit 131D. In this case, the portion or area of the image of interest of the displayed images is designated by appropriate designating means, whereby the corresponding numerical value or graph can be called, or a specific numerical value or graph area can be emphasized with different colors so as to allow the specific numerical value or graph area to be easy to be confirmed. When a different specimen is stored for each of a large number of containers (e.g., by organs, by pathologies, by patients, by measurement items), the analysis can be made such that the desired order or correlation by specimens is expressed onto the display unit 131D. The variety of analyses and display form can be realized by replaceable software or an internal program so as to be capable of being executed.

In the above-mentioned configuration, various electronic controls and management and control of signal processing are exclusively performed by the controller 132D. The controller 132D may execute, on real time, a health care such as data sharing or diagnosis in a decentralized manner or with a centralized control by a host computer, by means of a remote system that is connected to the large number of examination devices or examination systems described above with a communication line (wirelessly or wiredly) so as to be communicable. Further, various useful medical databases and the controller 132D are connectable with communication in order that the latest data can be obtained on real time and the relation between the latest data and the biological system can be analyzed.

Figure 39:
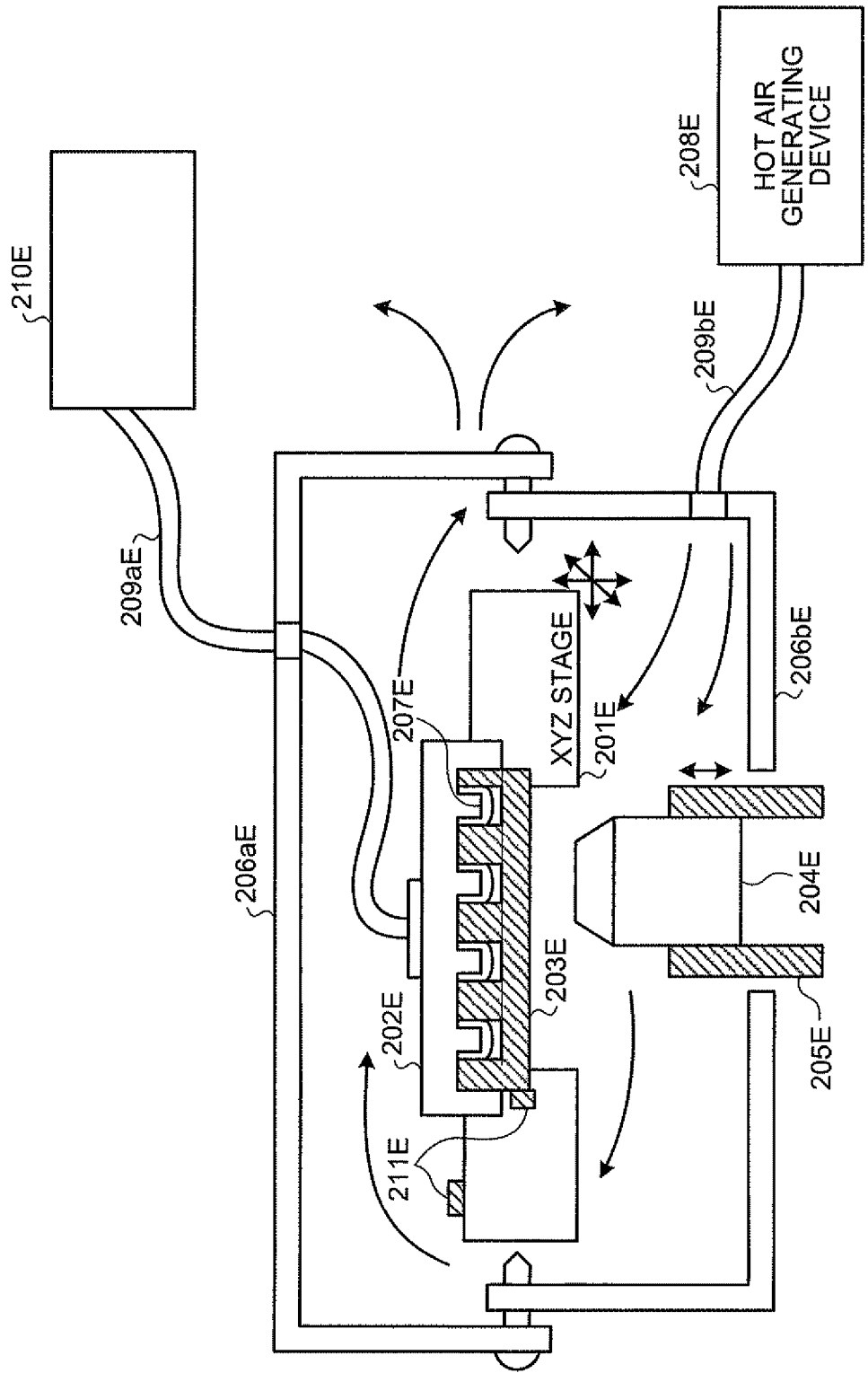
FIG. 39 is a view for showing one specific example of the configuration of a modification of the examination system according to the third embodiment.

FIG. 39 shows a modification of the examination system, which is an example of the case where an image of a specimen is formed with an objective lens. A microplate 203E that has a flat bottom surface and is made of a glass or plastic is fixed onto an XYZ stage 201E that is electrically controlled. Only the surrounding of the miscoplate 203E is brought into contact with the XYZ stage 201E in order that all wells 207E formed to the microplate 203E are exposed downward. A plate cover 202E is provided above the microplate 203E for lidding the microplate so as to cover the upper portion of the wells 207E and the microplate and fixing the microplate onto the XYZ stage 201E. A pipe not shown is formed to the plate cover 202E, whereby the plate cover 202E is connected to a gas feed unit 210E for feeding and discharging a gas (e.g., carbon dioxide, hot air) of a predetermined condition to and from each well through a soft tube 209aE. A housing 206E that houses the overall system includes an upper housing 206aE that is openable and closable for a plate replacement, reagent dispensing, ventilation, etc., and a lower housing 206bE that is a base for fixing each unit. The temperature in the housing 206E rises so as to be suitable for the biological activity by sending hot air into the housing through a tube 209bE from a hot air generating device 208E. It is preferable that the temperature of the microplate 203E and the XYZ stage 201E is controlled by a temperature sensor 211E to be a desired temperature through the controller shown in FIG. 37.

In the observation of luminescence (particularly, bioluminescence in a cell) that is an example of a feeble light, it is preferable to secure a field of view by which the individual cell can exhaustively recognized with an objective lens 204E having a low magnification (e.g., ×2 to ×20, particularly, ×4 to ×10). Therefore, this system is suitable for freely moving the microplate 203E. When a mounting error or lot difference of the microplate 203E should be considered, it is preferable to adjust the distance between the bottom surface of the microplate 203E and the objective lens 204E to a suitable distance by the illustrated Z-axis driving mechanism 205E, even for the objective lens 204E having any magnifications.

The explanation of the configuration of each unit in the third embodiment is completed here.

3. Process of Focal Position Determining Apparatus 1

Figure 40:
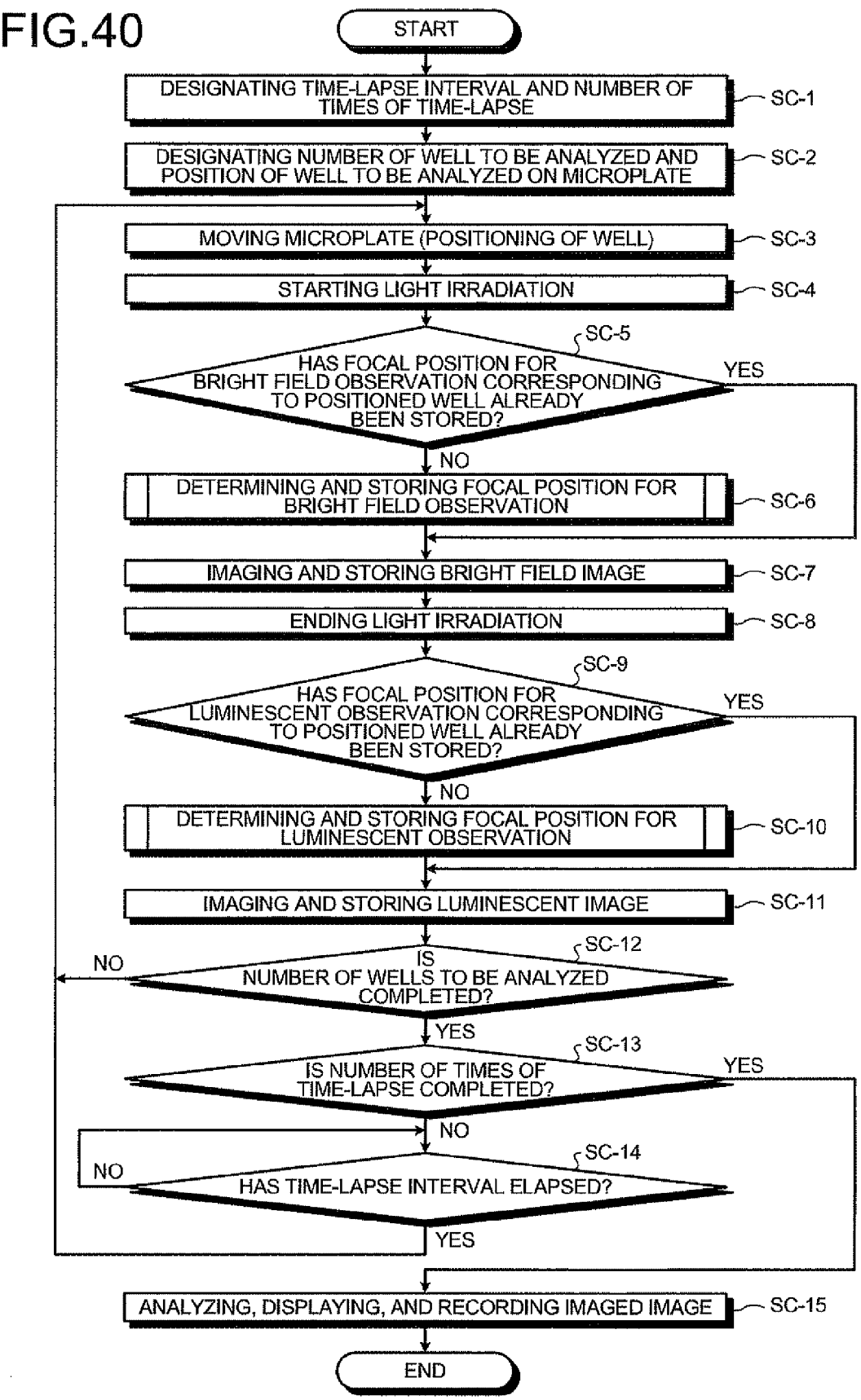
FIG. 40 is a flowchart for showing one example of a biological specimen imaging and analyzing process executed by the focal position determining apparatus 1 that serves as the biological specimen imaging apparatus according to the third embodiment.

Next, a biological specimen imaging and analyzing process executed by the focal position determining apparatus 1, which is a biological specimen imaging apparatus, according to the third embodiment will be explained with reference to FIG. 40 or other figures. FIG. 40 is a flowchart for showing one example of the biological specimen imaging and analyzing process executed by the focal position determining apparatus 1, which is a biological specimen imaging apparatus, according to the third embodiment. Explained here is the case in which a biological cell is observed in a bright field of view and a luminescence of the biological cell is observed by means of the focal position determining apparatus 1 shown in FIG. 33.

When an observer places a microplate, having a biological cell that is the specimen 10 in each well, onto the specimen stage 17, and starts the focal position determining apparatus 1 and the light source 20, the focal position determining apparatus 1 executes the processes described below.

The focal position determining apparatus 1 firstly causes the observer to designate a time interval (time-lapse interval) when a time-lapse observation of the biological cell is performed and a number of times (time-lapse number of times) for performing the time-lapse observation by the control unit 70a of the information processing device 70 (step SC-1).

Then, the focal position determining apparatus 1 causes the observer to designate the number of the wells that are subjects to be observed (wells to be observed) of the wells of the microplate, the observation order and the position of the wells to be observed on the microplate by the control unit 70a of the information processing device 70 (step SC-2).

Subsequently, the focal position determining apparatus 1 suitably operates the stepping motors mounted at the predetermined positions of the specimen stage 17 by the control unit 70a of the information processing device 70, and moves the microplate (actually, the specimen stage 17), based on the position designated at the step SC-2 (specifically, the position on the microplate of the well to be observed whose observation order is first), until the well to be observed corresponding to this position falls within the field of view of the objective lens 30, so as to perform the positioning of the well to be observed (step SC-3). At the step SC-3, after the microplate is completely moved, the position of the well at the moving destination may be measured, and the moving destination positional information relating to the measured position of the well at the moving destination may be stored as associated with storing unit identifying information for identifying the well. With this, when the well, which is the same as the well that is positioned previously, is again positioned, the same well can quickly and appropriately be positioned based on the stored moving destination positional information and the storing unit identifying information.

Then, the focal position determining apparatus 1 starts the irradiation to the biological cell with an illumination light emitted from the light source 20 in order to start the bright field observation (step SC-4).

Next, when the focal position determining apparatus 1 does not store the focal position for the bright field observation corresponding to the well to be observed that is positioned at the step SC-3 (step SC-5: No), it suitably operates each unit by the control unit 70a of the information processing device 70, and executes the focal position determining process shown in FIG. 41 so as to determine and store the focal position for the bright field observation corresponding to the well to be observed that is positioned (step SC-6). When the focal position for the bright field observation corresponding to the well to be observed that is positioned at the step SC-3 is stored (step SC-5: Yes), the program proceeds to step SC-7.

The focal position determining process executed by the focal position determining apparatus 1, which is the biological specimen imaging apparatus, according to the third embodiment will be explained with reference to FIG. 41. FIG. 41 is a flowchart for showing one example of the focal position determining process executed by the focal position determining apparatus 1, which is the biological specimen imaging apparatus, according to the third embodiment. Explained here is the case in which the focal position determining apparatus 1 shown in FIG. 33 is used.

The focal position determining apparatus 1 firstly causes the objective lens z-axis moving mechanism to operate by the control unit 70a of the information processing device 70, whereby the objective lens 30 is moved by a constant distance along an optical axis from the initial position by the objective lens z-axis moving mechanism so as to change the focal position of the objective lens 30 (step SD-1).

Then, the focal position determining apparatus 1 operates the focal position measuring unit 50 by the control unit 70a of the information processing device 70 so as to detect and store the focal position of the objective lens 30 by the focal position measuring unit 50 (step SD-2).

Next, the focal position determining apparatus 1 operates the CCD camera by the control unit 70a of the information processing device 70 so as to image and store a bright field image of the biological cell by the CCD camera, when light is irradiated, and to image and store a luminescent image of the biological cell by the CCD camera, when light is not irradiated (step SD-3).

Next, the focal position determining apparatus 1 operates the feature data calculating unit 70a1 by the control unit 70a of the information processing device 70 so as to calculate a contrast of the imaged image based on the imaged image (bright field image or luminescent image) taken at the step SD-3 by the feature data calculating unit 70a1 (step SD-4). The focal position determining apparatus 1 stores, in the imaged image database 70b1 of the storage unit 70b, the focal position detected at the step SD-2, the imaged image taken at the step SD-3, and the contrast calculated at the step SD-4, as associated with one another, by the control unit 70a of the information processing device 70.

Next, the focal position determining apparatus 1 repeatedly executes the processes from the step SD-1 to the step SD-4 by the control unit 70a of the information processing device 70, until the focal position of the objective lens 30 that is changed at the step SD-1 passes the predetermined position on the optical axis (step SD-5).

Then, the focal position determining apparatus 1 operates the focal position selector 70a2 by the control unit 70a of the information processing device 70 so as to select two contrasts, among the plural contrasts stored in the imaged image database 70b1, which are the maximum by the focal position selector 70a2, and acquires two focal positions stored in the imaged image database 70b1 as associated with the selected contrasts. Then, the focal position determining apparatus 1 operates the focal position determining unit 70a3 by the control unit 70a of the information processing device 70 so as to determine, as the focal position of the objective lens 30 focused on the observed target region 10a in the biological cell, the central position (substantial central position) between the two focal positions based on the acquired two focal positions by the focal position determining unit 70a3 (step SD-6). In other words, the focal position determining apparatus 1 selects, by the focal position selector 70a2, the focal position (substantial focal position) at the near point of the objective lens 30 and the focal position (substantial focal position) at the far point of the objective lens 30 from the plural focal positions stored in the imaged image database 70b1 based on the plural feature data pieces stored in the imaged image database 70b1, and determines, by the focal position determining unit 70a3, the central position (substantial central position) between the selected two focal positions as the focal position of the objective lens 30 focused on the observed target region 10a in the biological cell based on the selected focal position at the near point and the focal position at the far point.

The explanation of the focal position determining process is completed here.

Returning back to FIG. 40, the focal position determining apparatus 1 operates the objective lens z-axis moving mechanism by the control unit 70a of the information processing device 70, moves the objective lens along the optical axis until the focal position of the objective lens 30 is adjusted to the focal position for the bright field observation determined at the step SC-6 (or the stored focal position for the bright field observation) by the objective lens z-axis moving mechanism, operates the CCD camera by the control unit 70a of the information processing device 70, and images and stores the bright field image of the biological cell at the moved focal position by the CCD camera (step SC-7).

Next, the focal position determining apparatus 1 ends the irradiation of the illumination light emitted from the light source 20 to the biological cell in order to end the bright field observation (step SC-8).

Then, when the focal position determining apparatus 1 does not store the focal position for the luminescent observation corresponding to the well to be observed that is positioned at the step sC-3 (step SC-9: No), it suitably operates each unit by the control unit 70a of the information processing device 70 so as to execute the focal position determining process shown in FIG. 41, whereby the focal position for the luminescent observation corresponding to the well to be observed that is positioned is determined and stored (step SC-10). When the focal position determining apparatus 1 stores the focal position for the luminescent observation corresponding to the well to be observed that is positioned at the step sC-3 (step SC-9: Yes), the program proceeds to step SC-11.

Next, the focal position determining apparatus 1 operates the objective lens z-axis moving mechanism by the control unit 70a of the information processing device 70, moves the objective lens along the optical axis until the focal position of the objective lens 30 is adjusted to the focal position for the luminescent observation determined at the step SC-10 (or the stored focal position for the luminescent observation) by the objective lens z-axis moving mechanism, operates the CCD camera by the control unit 70a of the information processing device 70, and images and stores the luminescent image, which is a feeble light image, relating to the biological cell at the moved focal position by the CCD camera (step SC-11).

Then, when the bright field observation and the luminescent observation corresponding to the number of the wells to be observed designated at the step SC-2 are not completed (step SC-12: No), the focal position determining apparatus 1 suitably operates each unit by the control unit 70a of the information processing device 70 so as to repeatedly execute the processes from the step SC-3 to step SC-11 for the remaining wells to be observed to which the bright field observation and the luminescent observation are not completed.

On the other hand, when the bright field observation and the luminescent observation corresponding to the number of the wells to be observed designated at the step SC-2 are completed (step SC-12: Yes), the focal position determining apparatus 1 confirms, by the control unit 70a of the information processing device 70, the number of times of the time-lapse observations that have been executed, and when the time-lapse number of times designated at the step SC-1 is completed as a result of the confirmation (step SC-13: Yes), the program proceeds to step SC-15.

On the other hand, when the time-lapse number of times designated at the step SC-1 is not completed (step SC-13: No), the focal position determining apparatus 1 confirms, by the control unit 70a of the information processing device 70, the lapse of time from the start of the time-lapse observation, and when the time-lapse interval designated at the step SC-1 has elapsed as a result of the confirmation (step SC-14: Yes), the program returns to the step SC-3 in order to start the remaining time-lapse observations.

The focal position determining apparatus 1 then analyzes the luminescent images obtained so far at the step SC-11, displays the same, and records the same by the control unit 70a of the information processing device 70 (step SC-15). If the luminescent image is analyzed together with the bright field image acquired at the step SC-7 (specifically, the luminescent image and the bright field image are superimposed and the superimposed image is analyzed), a quicker and more correct analysis can be performed.

The explanation of the biological specimen imaging and analyzing process is ended here.

The explanation of the third embodiment is ended here.

EXAMPLE

In the present example, the objective lens was focused on plural HeLa cells in which plasmid vector was transduced, the HeLa cell, which was the subject, was selected from the plural HeLa cells, and the luminescent amount and ATP amount from mitochondria in the selected HeLa cell were measured over time, by using the focal position determining apparatus 1 according to the second embodiment. The experiment in the present example was performed according to the (step 1) to (step 7) described below.

(Step 1) A fusion gene in which fluorescent protein (GFP), mitochondria localization signal, and luciferase were combined was prepared.

(Step 2) A plasmid vector having the fusion gene therein was transduced to a HeLa cell.

Figure 23:
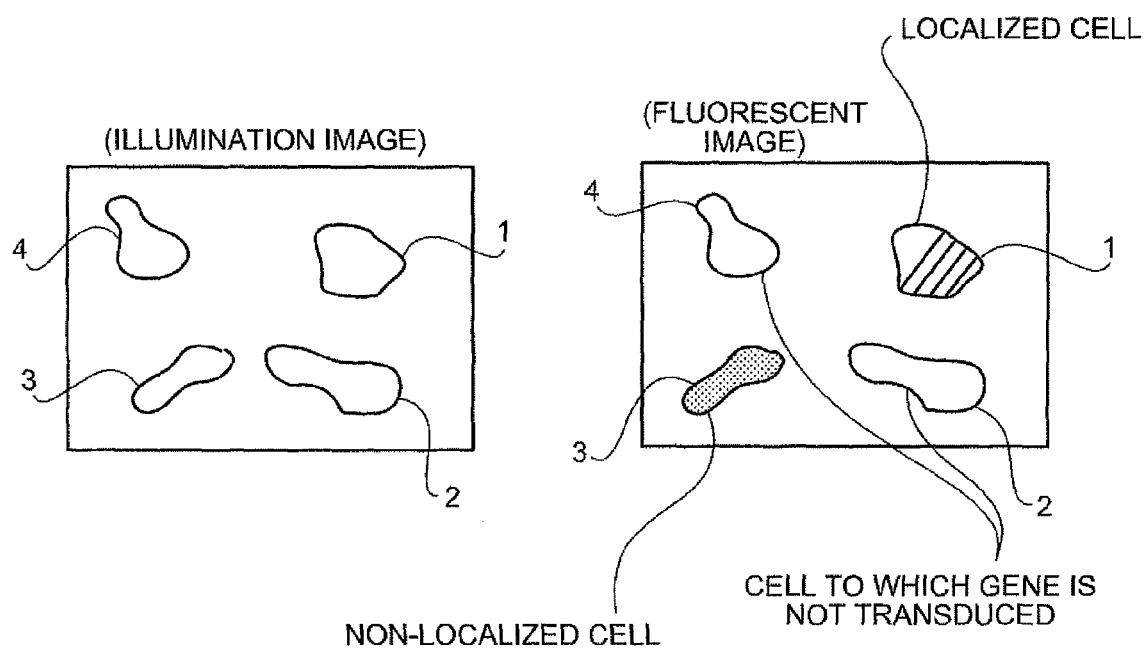
FIG. 23 is a view showing an illumination image and a fluorescent image of a HeLa cell transduced with plasmid vector.

(Step 3) With the use of the focal position determining apparatus 1, the focal position of the objective lens was adjusted to the mitochondria in the HeLa cell, and the HeLa cell was imaged by the CCD camera with the illumination and without the illumination. Then, it was determined whether GFP was localized in mitochondria or not based on the imaged images (fluorescent image) so as to confirm whether luciferase was localized or not in mitochondria (see FIG. 23). FIG. 23 is a view showing the illumination image and fluorescent image of the HeLa cell having plasmid vector transduced thereto.

(Step 4) Histamine was administered to the HeLa cell to cause the variation in the ATP amount in mitochondria via $Ca^{2+}$.

Figure 24:
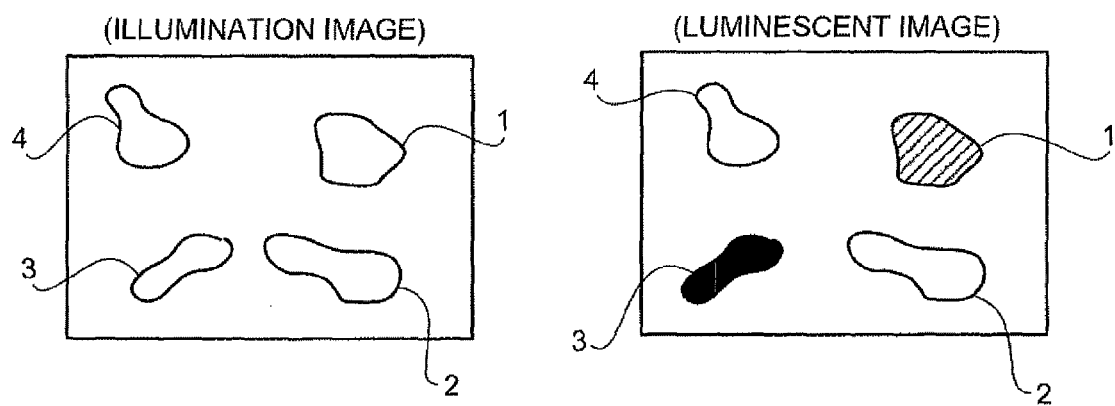
FIG. 24 is a view showing an illumination image and a luminescent image of a HeLa cell transduced with plasmid vector.

(Step 5) The HeLa cell was imaged with the illumination and without the illumination by the CCD camera, so that luminescent images in which luminescence from mitochondria in the HeLa cell was caught were obtained over time (see FIG. 24). FIG. 24 is a view showing the illumination image and luminescent image of the HeLa cell having plasmid vector transduced thereto.

(Step 6) The imaged illumination image, fluorescent image, and the luminescent image were overlapped with one another so as to select the subject HeLa cell.

(Step 7) The variation over time in the intensity of the luminescence from mitochondria in the selected HeLa cell was measured, and further, the variation over time in the ATP amount was monitored.

Figure 25:
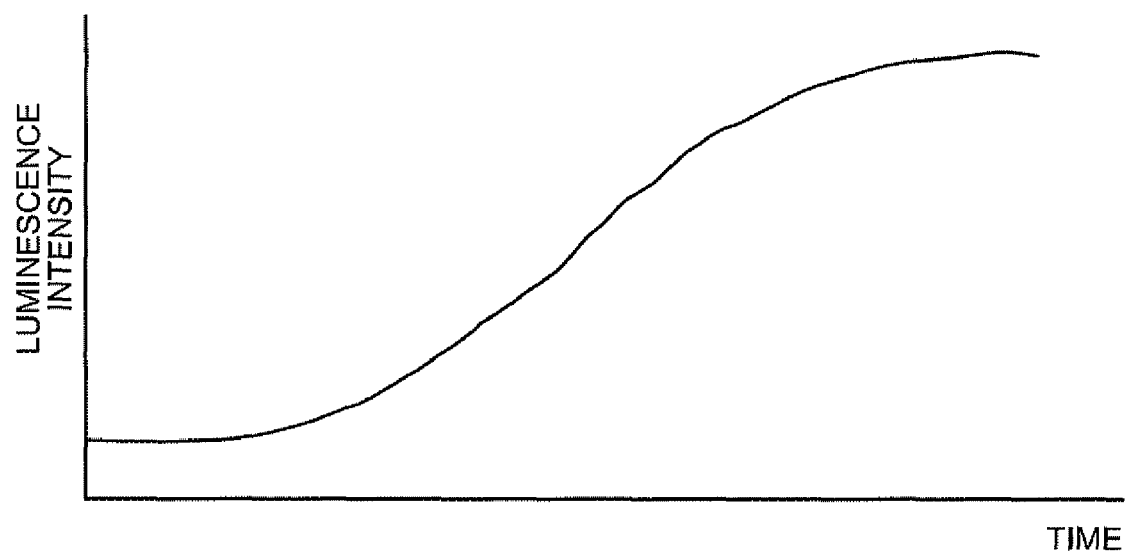
FIG. 25 is a graph showing a change, over time, of a luminescent intensity from the selected HeLa cell of No. 1.

The result of the experiment will be next explained, As shown in FIG. 23, it was confirmed that in the HeLa cell of No. 1, the fusion gene was transduced by plasmid vector and luciferase was localized in mitochondria. It was confirmed that, in the HeLa cell of No. 2 and the HeLa cell of No. 4, the fusion gene was not transduced by plasmid vector. Further, it was confirmed that, in the HeLa cell of No. 3, the fusion gene was transduced by plasmid vector, but luciferase was not localized in mitochondria. Specifically, the HeLa cell that was confirmed to have the fusion gene transduced by plasmid vector and have luciferase localized in mitochondria was only the HeLa cell of No. 1. Therefore, the HeLa cell of No. 1 was selected as the subject HeLa cell. As shown in FIG. 24, it was confirmed that the intensity of the luminescence from the HeLa cell of No. 3 was the greatest, the intensity of the luminescence from the HeLa cell of No. 1 was the second greatest, and the intensity of the luminescence from the HeLa cell of No. 2 and the HeLa cell of No. 4 were almost equal to each other. As shown in FIG. 25, the variation over time in the intensity of the luminescence from mitochondria in the HeLa cell of No. 1 could be monitored. FIG. 25 is a view showing a variation over time of the intensity of the luminescence from the selected HeLa cell of No. 1.

Next, a focal position determining method and a focal position determining apparatus advantageous for the analyzing method and analyzing apparatus of analyzing a feeble light image according to the present invention described above will be described as Additional Items. To solve the above problems and achieve the above objects, a focal position determining method according to Additional Item 1 of the present invention is a focal position determining method for determining a focal position of an objective lens focused on an observed target region in a specimen. The focal position determining method according to Additional Item 1 of the present invention includes measuring any one of the focal position of the objective lens at a near point and the focal position of the objective lens at a far point or both so as to determine the focal position of the objective lens focused on the observed target region based on the measured focal position.

a focal position determining method according to Additional Item 2 of the present invention is a focal position determining method for determining a focal position of an objective lens focused on an observed target region in a specimen. The focal position determining method according to Additional Item 2 of the present invention includes a light irradiating step of irradiating light to the specimen, a focal position changing step of changing the focal position of the objective lens, a focal position measuring step of measuring the focal position that is changed at the focal position changing step, a specimen imaging step of imaging the specimen to which light is irradiated at the light irradiating step, at the focal position changed at the focal position changing step, a feature data calculating step of calculating feature data characterizing the imaged image based on the image taken at the specimen imaging step, an executing step of repeatedly executing the focal position changing step, focal position measuring step, specimen imaging step, and feature data calculating step, a focal position selecting step of selecting at least one focal position from the plural focal positions accumulated by the execution of the executing step based on the plural feature data accumulated by the execution, and a focal position determining step of determining the focal position of the objective lens focused on the observed target region based on the focal position selected at the focal position selecting step.

The focal position determining method according to Additional Item 3 of the present invention is the focal position determining method described in Additional Item 2, wherein at the focal position selecting step, two focal positions are selected from the plural focal positions accumulated by the execution of the executing step based on the plural feature data accumulated by the execution, and at the focal position determining step, the central position between the two focal positions is determined as the focal position focused on the observed target region based on the two focal positions selected at the focal position selecting step.

The focal position determining method according to Additional Item 4 of the present invention is the focal position determining method described in Additional Item 3, wherein the two focal positions are the focal position of the objective lens at a near point and the focal position of the objective lens at a far point.

The focal position determining method according to Additional Item 5 of the present invention is the focal position determining method described in Additional Item 2, wherein at the focal position selecting step, one focal position is selected from the plural focal positions accumulated by the execution of the executing step based on the plural feature data accumulated by the execution, and at the focal position determining step, the position apart from the focal position by a predetermined distance is determined as the focal position focused on the observed target region based on the one focal position selected at the focal position selecting step and the predetermined distance.

The focal position determining method according to Additional Item 6 of the present invention is the focal position determining method described in Additional Item 5, wherein the one focal position is the focal position of the objective lens at the near point or the focal position of the objective lens at the far point.

The focal position determining method according to Additional Item 7 of the present invention is the focal position determining method described in any one of Additional Items 2 to 6, and further includes a specimen-at-focal-position imaging step of imaging the specimen at the focal position determined at the focal position determining step, a focal position feature data calculating step of calculating the feature data based on the image imaged at the specimen-at-focal-position imaging step, a determined focal position changing step of changing the focal position determined at the focal position determining step, a determined specimen imaging step of imaging the specimen at the focal position changed at the determined focal position changing step, a determined feature data calculating step of calculating the feature data based on the image imaged at the determined specimen imaging step, a feature data comparing step of comparing the feature data calculated at the focal position feature data calculating step and the feature data calculated at the determined feature data calculating step, and a focal position re-determining step of re-determining the focal position changed at the determined focal position changing step as the focal position of the objective lens focused on the observed target region when the feature data calculated at the determined feature data calculating step is greater as the result of the comparison at the feature data comparing step.

The focal position determining method according to Additional Item 8 of the present invention is the focal position determining method described in any one of Additional Items 2 to 7, wherein the specimen is a living cell or tissue.

The present invention also relates to a focal position determining apparatus. The focal position determining apparatus according to Additional Item 9 of the present invention is the focal position determining apparatus that determines a focal position of an objective lens focused on an observed target region in a specimen. The focal position determining apparatus according to Additional Item 9 of the present invention includes a light irradiator that irradiates light to the specimen, a focal position changer that changes the focal position of the objective lens, a focal position measurer that measures the focal position of the objective lens, a specimen imager that images the specimen, a feature data calculator that calculates feature data characterizing the imaged image based on the image taken by the specimen imager, a controller that controls the focal position changer, focal position measurer, specimen imager, and feature data calculator so as to repeatedly execute the focal position changer, focal position measurer, specimen imager, and feature data calculator, a focal position selector that selects at least one focal position from the plural focal positions accumulated by the repeated execution by the controller based on the plural feature data accumulated by the repeated execution, and a focal position determining unit that determines the focal position of the objective lens focused on the observed target region based on the focal position selected by the focal position selector.

The focal position determining apparatus according to Additional Item 10 of the present invention is the focal position determining apparatus described in Additional Item 9, wherein the focal position selector selects two focal positions from the accumulated plural focal positions based on the accumulated plural feature data, and the focal position determining unit determines, as the focal position focused on the observed target region, the central position between the two focal positions based on the two foal positions selected by the focal position selector.

The focal position determining apparatus according to Additional Item 11 of the present invention is the focal position determining apparatus described in Additional Item 10, wherein the two focal positions are the focal position of the objective lens at a near point and the focal position of the objective lens at a far point.

The focal position determining apparatus according to Additional Item 12 of the present invention is the focal position determining apparatus described in Additional Item 9, wherein the focal position selector selects one focal position from the accumulated plural focal positions based on the accumulated plural feature data, and the focal position determining unit determines, as the focal position focused on the observed target region, the position apart from the focal position by a predetermined distance based on the one focal position selected by the focal position selector and the predetermined distance.

The focal position determining apparatus according to Additional Item 13 of the present invention is the focal position determining apparatus described in Additional Item 12, wherein the one focal position is the focal position of the objective lens at the near point or the focal position of the objective lens at the far point.

The focal position determining apparatus according to Additional Item 14 of the present invention is the focal position determining apparatus described in any one of Additional Items 9 to 13, and further includes a feature data comparator that compares two feature data individually calculated beforehand by the feature data calculator, and a focal position re-determining unit that re-determines the focal position of the objective lens focused on the observed target region based on the result of the comparison by the feature data comparator, wherein the specimen is imaged by the specimen imager at the focal position determined by the focal position determining unit, the feature data is calculated by the feature data calculator based on the imaged image, the focal position determined by the focal position determining unit is changed by the focal position changer, the specimen is imaged at the changed focal position by the specimen imager, the feature data is calculated by the feature data calculator based on the imaged image, the feature data corresponding to the determined focal position and the feature data corresponding to the changed focal position are compared by the feature data comparator, and when the feature data corresponding to the changed focal position is greater as the result of the comparison, the changed focal position is re-determined as the focal position of the objective lens focused on the observed target region by the focal position re-determining unit.

The focal position determining apparatus according to Additional Item 15 of the present invention is the focal position determining apparatus described in any one of Additional Items 9 to 14, wherein the specimen is a living cell or tissue.

The focal position determining apparatus according to Additional Item 16 of the present invention is the focal position determining apparatus described in any one of Additional Items 9 to 15, wherein an aperture is formed at the pupil position of an illumination optical system including the light irradiator.

The focal position determining apparatus according to Additional Item 17 of the present invention is the focal position determining apparatus described in Additional Item 16, wherein the aperture is decentered relative to the optical axis.

The focal position determining apparatus according to Additional Item 18 of the present invention is the focal position determining apparatus described in any one of Additional Items 9 to 15, wherein a narrow-band-pass filter is arranged to the illumination optical system including the light irradiator.

The focal position determining apparatus according to Additional Item 19 of the present invention is the focal position determining apparatus described in any one of Additional Items 9 to 18, wherein the light irradiator emits monochromatic visible light.

The focal position determining apparatus according to Additional Item 20 of the present invention is the focal position determining apparatus described in any one of Additional Items 9 to 19, and further includes an exciting light irradiator that irradiates exciting light to the specimen.

In Additional Item described above, any one of the focal position (substantial focal position) of the objective lens at the near point and the focal position (substantial focal position) of the objective lens at the far point or both are measured, and the focal position of the objective lens focused on the observed target region based on the measured focal position is determined. When the specific region in the specimen is defined as the observed target region, and the luminescence of the observed target region is observed, the focal position of the objective lens focused on the observed target region can be determined at the time of setting the specimen, and therefore, the focal position of the objective lens can be focused on the observed target region. Further, the present invention provides an effect that, when the luminescent region in the specimen is observed, the objective lens can be focused on the luminescent region in the specimen without confirming the luminescence from the luminescent region.

The focal position determining method and focal position determining apparatus according to the present invention (1) irradiate light to the specimen, (2) change the focal position of the objective lens, (3) measure the changed focal position, (4) image the specimen to which the light is irradiated, at the changed focal position, (5) calculate feature data characterizing the imaged image based on the imaged image, (6) repeat the processes at (2) to (5), (7) select at least one focal position from the plural focal positions accumulated by the execution based on the plural feature data accumulated by the execution, (8) determine the focal position of the objective lens focused on the observed target region in the specimen based on the selected focal position. When the specific region in the specimen is defined as the observed target region, and the luminescence of the observed target region is observed, the focal position of the objective lens focused on the observed target region can be determined at the time of setting the specimen, and therefore, the focal position of the objective lens can be focused on the observed target region. Further, the present invention provides an effect that, when the luminescent region in the specimen is observed, the objective lens can be focused on the luminescent region in the specimen without confirming the luminescence from the luminescent region.

The focal position determining method and focal position determining apparatus according to the present invention select, in the above-described (7), two focal positions from the plural focal positions accumulated by the execution based on the plural feature data accumulated by the execution, and determine, in the above-described (8), the central position (substantial central position) between the two focal positions as the focal position focused on the observed target region based on the selected two focal positions. The present invention provides an effect that the focal position of the objective lens focused on the observed target region in the specimen can easily be determined.

In the focal position determining method and focal position determining apparatus according to the present invention, the two focal positions are the focal position (substantial focal position) of the objective lens at the near point and the focal position (substantial focal position) of the objective lens at the far point. The present invention provides an effect that the focal position of the objective lens focused on the observed target region in the specimen can easily and simply be determined.

The focal position determining method and focal position determining apparatus according to the present invention select, in the above-described (7), one focal position from the plural focal positions accumulated by the execution based on the plural feature data accumulated by the execution, and determiner in the above-described (8), the position apart from the focal position by the predetermined distance as the focal position focused on the observed target region based on the selected the one focal position and the predetermined distance. The present invention provides an effect that the focal position of the objective lens focused on the observed target region in the specimen can more easily be determined.

In the focal position determining method and focal position determining apparatus according to the present invention, the one focal position is the focal position (substantial focal position) of the objective lens at the near point or the focal position (substantial focal position) of the objective lens at the far point. The present invention provides an effect that the focal position of the objective lens focused on the observed target region in the specimen can more easily and simply be determined.

The focal position determining method and focal position determining apparatus according to the present invention (9) image the specimen at the focal position determined at the above-described (8), (10) calculate the feature data based on the imaged image, (11) change the focal position determined at the above-described (8), (12) image the specimen at the changed focal position, (13) calculate the feature data based on the imaged image, (14) compare the feature data calculated at (10) and the feature data calculated at (13), (15) re-determine the focal position changed at (11) as the focal position of the objective lens focused on the observed target region when the feature data calculated at (13) is greater as the result of the comparison. The present invention provides an effect that the focal position of the objective lens focused on the observed target region in the specimen can be continuously determined not only at the time of setting the specimen but also from the start of the observation of the luminescence of the specimen, with the result that the objective lens can always be focused on the observed target region. The specimen is a living cell or tissue. The present invention provides an effect that a material emitting feeble light can be used as a specimen.

In the focal position determining apparatus according to the present invention, an aperture is formed at the pupil position of an illumination optical system including the light irradiator (light source). The present invention provides an effect that a phase difference between transmitted light and diffraction light can be increased, with the result that the contrast of the imaged image can be increased. The aperture is decentered relative to the optical axis. The present invention provides an effect that a phase difference between transmitted light and diffraction light can be more increased, with the result that the contrast of the imaged image can be more increased. A narrow-band-pass filter is arranged to the illumination optical system including the light irradiator (light source). The present invention provides an effect that light emitted from a light source can be made to be monochromatic light whose wavelength band width is extremely narrow, with the result that the contrast of the imaged image can be increased. The light irradiator (light source) emits monochromatic visible light. The present invention provides an effect that, when light emitted from the light source is irradiated to the specimen, the wavelength dispersion hardly appears, so that a sharp diffraction light can be obtained, with the result that the contrast of the imaged image can be increased. An exciting light irradiator (exciting light source) that irradiates exciting light to the specimen is included. The present invention provides an effect that fluorescence and luminescence of the specimen can simultaneously be observed.

The present invention can be construed to include the invention described in Additional Items below.

Additional Item 1A: A method of analyzing a feeble light image includes, when analyzing an image of a biological specimen emitting a feeble light, determining at least one reference position relating to a target region to be analyzed of the biological specimen by using electromagnetic energy that is different from the feeble light, determining a focal position for the feeble light corresponding to the target region with respect to the reference position, forming an image according to the feeble light with the focus set to the determined focal position, extracting a numerical value of a necessary measurement parameter from the feeble light image, and evaluating the target region based on the extracted parameter numerical value.

Additional Item 2A: The method of analyzing a feeble light image described in Additional Item 1A, wherein the determination of the reference position includes the acquisition of the reference image by the electromagnetic energy.

Additional Item 3A: The method of analyzing a feeble light image described in Additional Item 2A, wherein, in the acquisition of the reference image, the image is acquired for the region of the specimen containing the target region.

Additional Item 4A: The method of analyzing a feeble light image described in Additional Item 1A or 2A, wherein the electromagnetic energy is any one of a visible light, near infrared rays, ultrasonic wave, and magnetic line, which give less damage to the living body.

Additional Item 5A: A method of analyzing a feeble light image including irradiating irradiation light, by which a biological specimen emitting a feeble light and difficult to directly be made visible, to the biological specimen so as to make the biological specimen visible, determining, as the focal position for the feeble light by the objective lens, the position corresponding to the distance required for forming an image according to the feeble light emitted from the target region to be analyzed in the biological specimen, with any one of the focal position at the near point of the objective lens receiving light from the reference image provided by the biological specimen that is made visible and the focal position at the far point of the objective lens or both defined as a reference position, focusing the objective lens onto the determined focal position for the feeble light so as to form the feeble light image of the biological specimen by accumulating the feeble light until a necessary image is obtained, and evaluating the presence or absence of the feeble light or the light intensity at the target region from the feeble light image.

Additional Item 6A: The method of analyzing the feeble light image described in Additional Item 5A, wherein it is defined that direct visualization is difficult when the exposure time for forming an optical image is 10 seconds or more.

Additional Item 7A: The method of analyzing the feeble light image described in Additional Item 5A, wherein an image signal based on the irradiation light is transmitted light or fluorescence.

Additional Item 8A: The method of analyzing the feeble light image described in any one of Additional Items 1A to 7A, wherein the focal position for the feeble light is determined for every observed region of the biological specimen.

Additional Item 9A: The method of analyzing the feeble light image described in any one of Additional Items 1A to 8A, wherein the reference position and the focal position are determined on the same beam path of the objective lens.

Additional Item 10A: The method of analyzing the feeble light image described in any one of Additional Items 1A to 9A, wherein the acquisition of the feeble light image is executed at plural times according to the examination items so as to accumulate plural feeble light images, the target regions to be observed of the accumulated plural feeble light images are collated, and the collated plural feeble light images are compared for every time.

Additional Item 11A: The method of analyzing the feeble light image described in any one of Additional Items 2A to 10A, wherein the focal positions of the reference image and the feeble light image are compared, and when they are out of range of the set distance, any one of the reference image and the feeble light image or both are again acquired.

Additional Item 12A: The method of analyzing the feeble light image described in Additional Item 11A, wherein the evaluation of the feeble light image further includes the acquisition of the measurement parameter from the reference image, and the evaluation of the feeble light parameter is executed as associated with the measurement data from the reference image.

Additional Item 13A: The method of analyzing the feeble light image described in Additional Item 12A, wherein the feeble light image is evaluated as associated with outline information of the target region in the reference image.

Additional Item 14A: The method of analyzing the feeble light image described in any one of Additional Items 1A to 13A, wherein the feeble light intensity per area corresponding to the outline of the target region is evaluated.

Additional Item 15A: The method of analyzing the feeble light image described in any one of Additional Items 1A to 13A, wherein, in the evaluation, the position or distribution of the feeble light in the outline of the target region is determined.

Additional Item 16A: The method of analyzing the feeble light image described in any one of Additional Items 1A to 15A, wherein the biological specimen is individually stored in plural storing sections, and the reference position is determined for every plural individual storing sections.

Additional Item 17A: The method of analyzing the feeble light image described in any one of Additional Items 1A to 16A, wherein the acquisition of the feeble light image is executed in a wide field of view including the plural storing sections.

Additional Item 18A: The method of analyzing the feeble light image described in Additional Item 17A, wherein the measurement parameter is acquired from the target region by any one of optically magnifying and electronically magnifying the feeble light image or both.

Additional Item 19A: The method of analyzing the feeble light image described in any one of Additional Items 1A to 17A, wherein the biological specimen is a living cell or tissue.

Additional Item 20A: The method of analyzing the feeble light image described in any one of Additional Items 1A to 19A, wherein the feeble light is a luminescence involved with the expression of a bioluminescent protein.

From the above explanation, it can be understood that the analyzing method and analyzing apparatus for analyzing a feeble light image, and the biological specimen imaging method and the biological specimen imaging apparatus according to the present invention have high industrial applicability in the luminescent observation, fluorescent observation and simultaneous observation of fluorescence and luminescence of a biological cell.

[II] Embodiments of the imaging method and imaging apparatus of a biological specimen according to the present invention will be explained in detail with reference to the drawings. It is to be noted that the present invention is not limited to the embodiments.

First Embodiment

The configuration of an apparatus for executing a luminescent specimen imaging method according to the first embodiment will be explained with reference to FIG. 26. FIG. 26 is a view for showing one example of a configuration of an apparatus for executing a luminescent specimen imaging method according to the first embodiment. As shown in FIG. 26, the apparatus for executing the luminescent specimen imaging method according to the first embodiment images a specimen 1A, which is a subject to be imaged, in a short exposure time or on a real time. It is composed of an objective lens 2A, the condenser lens 3A, CCD camera 4A and CPU 5A. The apparatus may include a zoom lens 6A as illustrated.

The specimen 1A is a luminescent specimen. For example, the specimen 1A is a luminescent protein (e.g., luminescent protein expressed from a transduced gene (luciferase gene, etc.)), luminescent cell, luminescent cell population, luminescent tissue specimen, luminescent organ, luminescent individual (animal, etc.) or the like. The specimen 1A may be a luminescent cell to which luciferase gene is transduced. The objective lens 2A is the one in which the square value of (NA÷β) represented by the numerical aperture (NA) and the projection magnification (β) is 0.01 or more, preferably 0.039 or more. The condenser lens 3A collects the luminescence reaching the condenser lens 3A from the specimen 1A through the objective lens 2A. The CCD camera 4A is a cooled CCD camera to about 0° C., and it images the specimen 1A through the objective lens 2A and the condenser lens 3A. The CPU 5A outputs the image taken by the CCD camera 4A.

Figure 27:
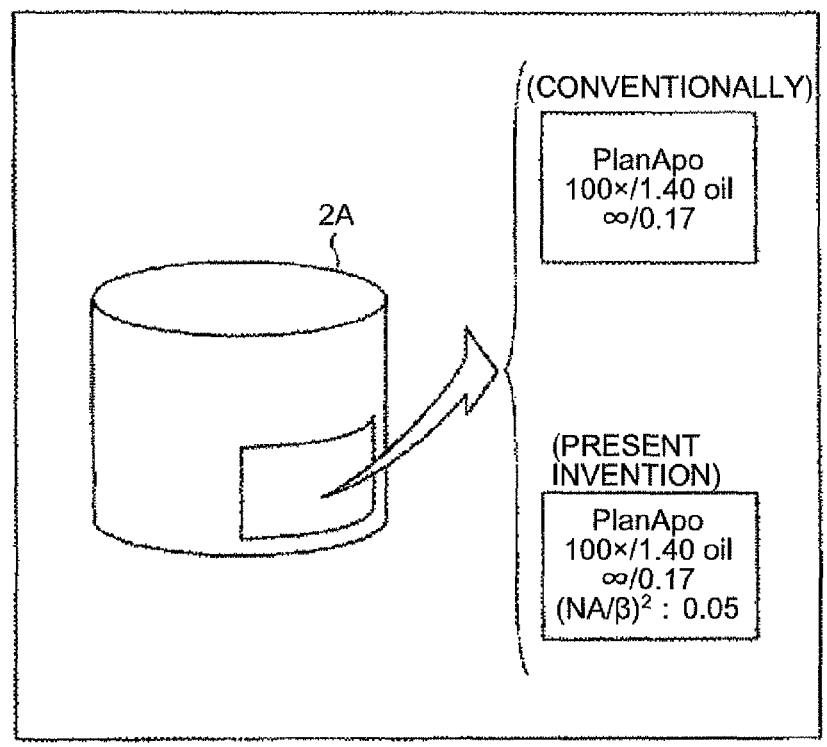
FIG. 27 is a view for showing one example of the objective lens 2A on which a square value of (NA/β) is written.

The square value of (NA/β) is written on the objective lens 2A or a packaging container (package) of the objective lens 2A. One example of the objective lens on which the square value of (NA/β) is written is explained with reference to FIG. 27. FIG. 27 is a view for showing one example of the objective lens 2A on which the square value of (NA/β) is written. On a conventional objective lens, a type of the lens (e.g., "Plan Apo"), magnification/NA oil-immersion (e.g., "100×/1.40 oil") and infinite distance/cover glass thickness (e.g., "∞/0.17") are written. However, on the objective lens (objective lens 2A) according to the present embodiment, emission aperture angle (e.g., "square of NA/β: 0.05") is written in addition to the type of the lens (e.g., "Plan Apo"), magnification/NA oil-immersion (e.g., "100×/1.40 oil") and infinite distance/cover glass thickness (e.g., "∞/0.17").

As explained above, in the apparatus for executing the luminescent specimen imaging method according to the first embodiment, the objective lens 2A has the square value of (NA÷β) represented by the numerical aperture (NA) and the projection magnification (β) of 0.01 or more, and preferably 0.039 or more. With this, a clear image can be imaged in a short exposure time or on a real time even for a luminescent specimen with reduced light emission amount such as a luminescent protein (e.g., luminescent protein expressed from a transduced gene (luciferase gene, etc.)), luminescent cell, luminescent cell population, luminescent tissue specimen, luminescent individual (animal, organ etc.) or the like. Specifically, a clear image can be imaged in a short exposure time or on a real time with a luminescent cell transduced with a luciferase gene defined as a subject to be imaged. Because the objective lens 2A has a great numerical aperture and small magnification, compared to a conventional objective lens, so that a wide range can be imaged with excellent resolution by using the objective lens 2A. Accordingly, an active luminescent specimen, a moving luminescent specimen, or a luminescent specimen distributed in a wide range can be imaged. On any one of the objective lens 2A and the packaging container (package) packaging the objective lens 2A or both, the square value of (NA÷β) represented by the numerical aperture (NA) and the projection magnification (β) (e.g., 0.01 or more, preferably 0.039 or more) is written. Accordingly, a person who observes the luminescent image can easily select an objective lens suitable for imaging the luminescent specimen in a short exposure time or on a real time by confirming the written square value of (NA÷β).

In the reporter assay using a luciferase gene, a light emission amount is conventionally measured after a cell is lysed, so that only the amount of the expression at a certain point can be caught, and further, the average value of the whole cell is to be measured. In the measurement during the culture, the change in the amount of the expression over time of a colony of a cell can be caught, but the change in the amount of the expression in an individual cell cannot be caught. In order to observe luminescence of an individual cell with a microscope, the cell should be exposed for a long time with a cooled CCD camera with a temperature level of liquid nitrogen, or a photon counting operation should be carried out with a CCD camera provided with an image intensifier, because the light emission amount from the living cell is extremely feeble. Therefore, a camera for detecting luminescence has to be expensive and large-scale. However, when the apparatus for executing the luminescent specimen imaging method according to the first embodiment is employed for observing luminescence of an individual cell exhibiting an activity of a luciferase as a reporter gene product, a quantitative image can be acquired by using a cooled CCD camera at about 0° C. without mounting an image intensifier. Specifically, when the apparatus for executing the luminescent specimen imaging method according to the first embodiment is employed, luminescence of an individual living cell can be observed with a cooled CCD camera at about 0° C., whereby the image intensifier or a device for a photon counting operation is unnecessary. In other words, a luminescent specimen can be imaged with low cost. Moreover, when the apparatus for executing the luminescent specimen imaging method according to the first embodiment is employed, luminescence of an individual cell can be observed over time while culturing the cell, so that the cell can be observed on a real time. Further, when the apparatus for executing the luminescent specimen imaging method according to the first embodiment is employed, a response to a drug or stimulus under different conditions can be monitored for the same cell.

In order to easily understand the luminescent specimen imaging method, the luminescent cell imaging method, and the objective lens according to the first embodiment, a conventional objective lens and an observation of a luminescent image using the same will briefly be explained.

In general, a spatial resolution ε in a microscopic observation is expressed by an equation 1 described below.

$$\epsilon = 0.61 \times \lambda \div NA \quad \text{(Equation 1)}$$

(In the equation 1, λ is a wavelength of light, and NA is a numerical aperture).

The diameter d of the observed range is expressed by an equation 2 described below.

$$d = D \div M \quad \text{(Equation 2)}$$

(In the equation 2, D is a number of fields, and M is a magnification. It is to be noted that the number of fields is generally 22 to 26.)

A focal distance of an objective lens for a microscope is conventionally defined as 45 mm with an international standard. Recently, an objective lens whose focal distance is 60 mm has been used. When a lens having a large NA, i.e., having a high spatial resolution is designed on the premise of this focal distance, the working distance (WD) is generally about 0.5 mm, and even in the lens designed to have a long working distance, it is only about 8 mm. When the objective lens described above is used, the observation range has a diameter of approximately 0.5 mm.

However, when a cell population, tissue or individual dispersed onto a dish or a glass-bottom dish is observed, the observation range becomes 1 to several centimeters in some cases. In order to observe this range with good resolution, the NA should be kept to be larger although the magnification is set to be low. In other words, it is necessary that the objective lens by which a wide range can be observed with the NA kept to be large has a low magnification, because the NA is a ratio of the lens diameter and the focal distance. Consequently, the objective lens described above has a large diameter. In the manufacture of a large-diameter objective lens, a high precision is demanded in uniformity of physical property of an optical material and uniformity in coating generally, or in a shape of a lens.

In the case of a microscopic observation, a transmittance of an optical system, numerical aperture of an objective lens, projection magnification on a chip face of a CCD camera, or performance of a CCD camera greatly affects a brightness of an image. The brightness of the image is evaluated by the square of the value obtained by dividing the numerical aperture (NA) by the projection magnification (β), i.e., (NA/β). In the objective lens, the relationship of the equation 3 described below is generally established between the entrance angular aperture NA and the exit angular aperture NA', and NA'² is the value indicating the brightness reaching the eyes of the observer or the CCD camera.

$$NA' = NA \div \beta \quad \text{(Equation 3)}$$

(In the equation 3, NA is an entrance angular aperture (numerical aperture), NA' is an exit angular aperture, and β is a projection magnification.)

In an ordinary objective lens, NA' is at most 0.04, and NA'² is at most 0.0016. When a brightness of an image (square value of (NA/β)) of an objective lens of an ordinary commercially available microscope is examined, it is in the range of 0.0005 to 0.002.

Meanwhile, even if a cell in which a luciferase gene is expressed to emit light is observed by using a microscope provided with an objective lens that is currently commercially available, the luminescence from the cell cannot be visually observed, and further, even if a luminescent image taken by means of a CCD camera that is cooled to about 0° C. is observed, the luminescence from the cell cannot be observed. When a luminescent specimen is observed, the irradiation of the excited light, which is required for the fluorescent observation, is unnecessary. For example, in an incident-light fluorescent observation, an objective lens has both a function as a projection lens of excited light and a function of a lens for condensing fluorescence to form an image. In order to observe a luminescence having less light amount in the form of an image, an objective lens having a large NA and a small β is required. Consequently, the objective lens of this type tends to have a large diameter. It is demanded that the objective lens of this type is easy to be designed and manufactured by simplifying the function without considering the function of projecting excited light.

In a research field utilizing a luminescent or fluorescent observation, a time-lapse or image-capture of a moving image has been demanded in order to catch the active functional expression of a protein molecule in a specimen. Recently, an observation of a moving image of one protein molecule utilizing fluorescence is carried out. In the image-capture described above, the exposure time per one frame of the image is shortened as the number of the image frame per unit time increases. In the observation described above, a bright optical system, in particular, a bright objective lens is needed. However, because the light amount of a luminescent protein is smaller than the fluorescence, the exposure time of about 20 minutes is taken for an image-capture of one frame, for example. Only a specimen in which an active change is very slow is subject to the time-lapse observation in the exposure time described above. For example, the change in the cycle cannot be observed in a cell that fissions once in about one hour. Therefore, it is important to increase a brightness of an optical system in order to efficiently form an image with less light amount while keeping high signal/noise ratio.

The objective lens according to the first embodiment fabricated considering the above-mentioned details has a larger NA and a smaller β compared to a commercially available objective lens. In case where a cooled CCD camera cooled to a low temperature of about 0 to 5° C., a luminescent image formed from a luminescent protein in an individual cell can be produced within five minutes by means of the objective lens having the square value of (NA/β) of 0.01 to 0.09, and the light emission amount for the individual cell can be measured. On the other hand, in the similar case, a luminescent image that can be recognized with naked eyes or by image analyzing software cannot be produced by an objective lens in which the square value of (NA/β) is not more than 0.007. Therefore, the square value of (NA/β) (or NA'²) of the objective lens according to the first embodiment by which a luminescent image can be produced is a significantly great value than that of a conventionally used objective lens. Specifically, it can be said that the objective lens according to the first embodiment is a bright objective lens under the condition different from the condition conventionally used. Thus, if a bright objective lens such as the objective lens according to the first embodiment is employed, the luminescence from a luminescent specimen having less light amount can be observed in the form of an image. Further, the objective lens according to the first embodiment having a large numerical aperture is mounted to a stereoscopic microscope in order to observe a darker image, whereby a luminescence of a cell can be observed in the form of an image even with a CCD camera cooled to about 0° C. without mounting an image intensifier. There is a method of increasing sensitivity by using a CCD camera cooled with a liquid nitrogen. However, in this case, the CCD camera becomes extremely expensive and large-scale. By using the objective lens according to the first embodiment, a luminescence of a cell can be observed in the form of an image even by a CCD camera cooled with Peltier cooling system. When an image is taken with a CCD camera provided with an image intensifier, a specimen is imaged in a mosaic form, so that it is extremely difficult to specify a cell emitting light (see "Current Biology, vol. 14 (2004), 2289-2295 by David K. Welsh, et al.").

The objective lens according to the first embodiment has a large diameter of about 5 cm to 10 cm. Accordingly, an active luminescent specimen, which oscillates, deforms, fissions, or moves and which cannot conventionally be the subject to be imaged, or a luminescent specimen distributed in a wide range can be defined as a subject to be imaged. According to the first embodiment, a visual field range of 1 by 1 centimeter square or more, preferably 2 by 2 to 5 by 5 centimeters square or more, in a cultured specimen (tissue or cell population) containing a cell can be observed. Accordingly, the first embodiment is preferable in that the whole or most part of various important tissues or organs (e.g., brain, suprachiasmatic nucleus, pancreas, tumor tissue, nematode, etc.) can be observed and analyzed arbitrarily in the form of a thin section or the like in a wide field of view. The above-mentioned explanation does not exclude the application of the first embodiment to a cooled CCD camera cooled to a very low temperature by means of a liquid nitrogen. This is because a high-speed imaging, which cannot be realized even with a CCD camera cooled to a very low temperature, can be realized only by an optical configuration containing the objective lens before light is received according to the first embodiment. Accordingly, when a CCD camera cooled to a very low temperature is combined with the method and apparatus of the first embodiment, sensitivity is enhanced and S/N ratio is increased, whereby an image quality can be enhanced.

The lens used as the objective lens 2A and the condenser lens 3A for imaging is, for example, a commercially available objective lens for a microscope having a specification of "Oil, ×20, NA 0.8" and "×5, NA 0.13", wherein the total magnification corresponding to the magnification Mg is ×4. The CCD camera 4A is, for example, a digital camera "DP30BW (by Olympus Corporation)" cooled to 5° C. for a microscope, and a CCD device is a ⅔ inch type having a pixel number of 1360×1024 and pixel size of 6 by 6 micrometers square.

The above-mentioned luminescent observation is carried out in a room temperature (25° C.). When a specimen is placed in an incubator, or when a part or whole of an imaging unit or an imaging apparatus is housed in an incubator, the luminescent observation is possible under an environment of 37° C.

According to the apparatus for executing the luminescent specimen imaging method according to the present embodiment, a feeble light emitted from a luciferase gene can be imaged, for example, with a cooled CCD camera cooled to 5° C. in a short exposure time such as one minute without a photon counting.

When a bright field image and an image according to a self-luminescence are overlapped with each other, the position of the luminescent luciferase gene can be observed in the form of a clear image, and further, the cell containing the luciferase gene can easily be specified.

According to the apparatus for executing the luminescent specimen imaging method according to the present embodiment, the position of the luminescent luciferase gene is specified and traced in a time-series manner, whereby the secular change in the luminescent phenomenon can be measured.

In the apparatus for executing the luminescent specimen imaging method according to the present embodiment, an imaging optical system composed of the objective lens 2A and the condenser lens 3A for imaging is an infinity corrected optical system, whereby various optical devices can be arranged between the objective lens 2A and the condenser lens 3A for observing the specimen 1A with various methods.

The apparatus for executing the luminescent specimen imaging method according to the present embodiment can be utilized as a biochip reader for optically reading a biochip such as DNA microarray, cell array, or protein array. A biochip having plural storing sections and serving as a substrate is a substrate made of glass or resin such as polystyrene, on which 2 to 1000 addressed microportions (the diameter thereof is, for example, 0.05 to 5.0 mm) are bonded at an interval of 0.1 to 1.0 mm. A variety of DNA (or RNA) pieces, synthetic oligonucleotides, cells, proteins, etc. is arranged on each of the microportions so as to examine molecular-biologically useful information such as the expression of the gene or presence of a specific gene. The fluorescence or luminescence emitted from the biochip is generally very feeble. By using the apparatus for executing the luminescent specimen imaging method according to the present embodiment, a real-time detection might be possible even if an amount of solidification to a conventional microbiochip in which a genetic or immunologic substance is formed into a solid phase is reduced. Thus, the apparatus for executing the luminescent specimen imaging method according to the present embodiment is excellent.

When a light emitted from a biochip is fluorescence, an ordinary biochip reader is a combination of a confocal optical system for a laser irradiation and a high-speed moving scanning stage. The photometry by this biochip reader is a sum of the light emission quantities at the points where spot excited light is irradiated, so that, every time the scanning width changes, the measured light amount changes. Therefore, an absolute light amount cannot be measured. When the apparatus for executing the luminescent specimen imaging method according to the present embodiment is used, the absolute light amount can be measured in the manner described below. Specifically, the stage holding the biochip is moved in increments of 0.6 mm with respect to the objective lens having a field of view with a diameter of 0.5 mm, and every time the stage is stopped, photometry is carried out. According to this embodiment, in particular, an imaging apparatus having an optical condition capable of sufficiently detecting a luminescence (chemiluminescence, particularly bioluminescence) emitting light more feeble than fluorescence can be designed according to a predetermined magnification, whereby a quantitative and high-sensitive analysis of luminescence in a biochip can be executed.

Second Embodiment

Figure 28:
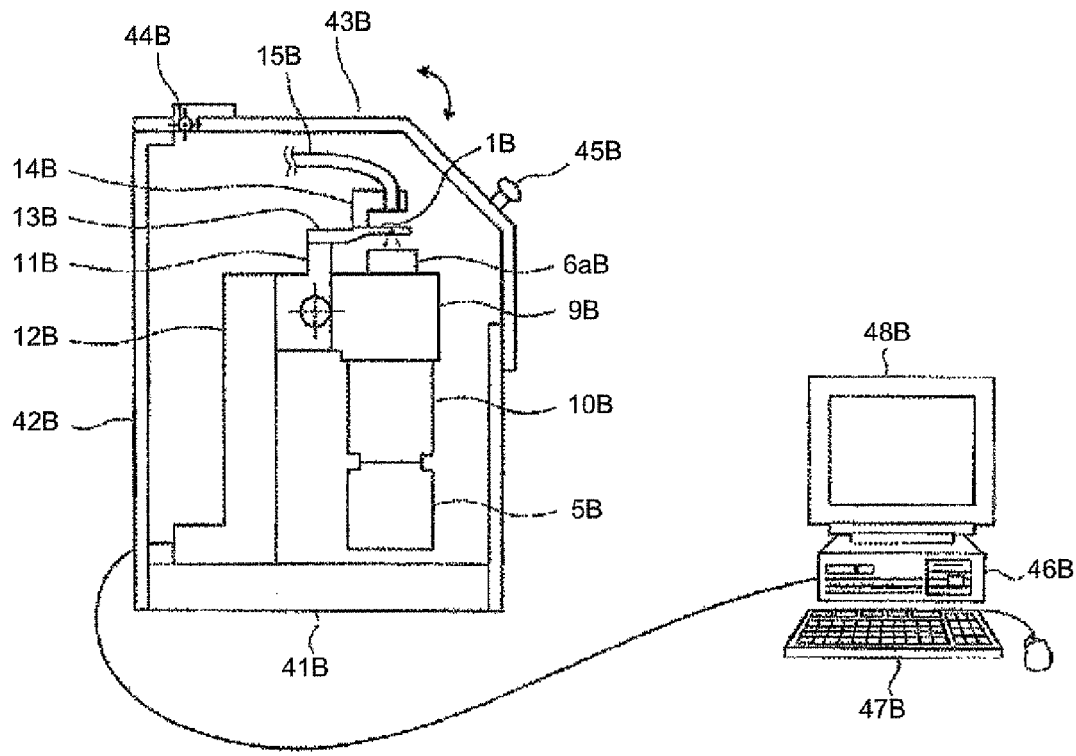
FIG. 28 is a view for showing a configuration in case where the feeble light specimen imaging apparatus shown in FIG. 26 is placed in a light-shielding apparatus so as to make an automatic control from the outside.

An apparatus (feeble light specimen imaging apparatus) for executing a luminescent specimen imaging method according to the second embodiment is of an inverted type. An inverted type feeble light specimen imaging apparatus shown in FIG. 28 is placed in a light-shielding device such as a chamber for shielding light from the outside, so that it can precisely and stably detect a feeble light without being affected by an external light. Therefore, it can clearly take an image with a self-luminescence of the specimen 1B. The light-shielding device shown in FIG. 28 forms a dark room by a base 41B, enclosure 42B and lid 43B. The feeble light specimen imaging apparatus is mounted on the base 41B in the dark room. In the light-shielding device, the lid 43B is opened about a hinge portion 44B by lifting a knob 45B, whereby the specimen 1B can be replaced.

When the feeble light specimen imaging apparatus according to the second embodiment is arranged in the light-shielding device, the feeble light specimen imaging apparatus may be remote-operated and automatically operated from the outside of the light-shielding device by a control device 46B such as a computer having an input device 47B such as a keyboard or mouse. In particular, the focusing operation and positioning operation to the specimen 1B, the imaging operation of a camera 5B or the like, the adaptation of illumination light by an illumination fiber 15B, or the like may be automatically controlled.

The positioning operation to the specimen 1B is the operation in which at least one of the imaging optical system composed of an objective lens 6aB and an imaging lens 10B and a specimen table 13B holding the camera 5B and the specimen 1B is moved in the direction substantially orthogonal to the optical axis so as to put the specimen 1B within the field of view of the objective lens 6aB. It may be processed such that the center of an Airy disk and the center of the pixel of the CCD match for every Airy disk of interest among the Airy disks formed by the imaging lens 10B, by utilizing the positioning operation described above. In this case, the Airy disk and the pixel may relatively two-dimensionally be operated so as to detect the position where the output corresponding to this pixel becomes the maximum.

The control device 46B has a display device 48B as shown in FIG. 28, wherein an image corresponding to a bright field image of the specimen 1B and an image corresponding to an image formed by a self-luminescence of the specimen 1B may be displayed on the display device 48B as overlapped with each other. The control device 46B may further include a storage unit, such as a memory, for storing these images.

Figure 29:
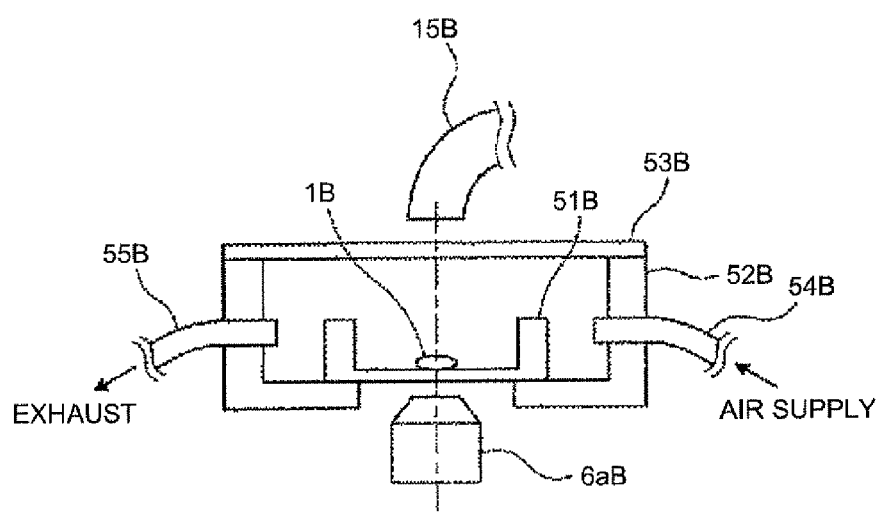
FIG. 29 is a view for showing a configuration of a container that has the sample 1B shown in FIG. 28 put therein and whose environmental condition is variable.

On the other hand, instead of the specimen table 13B, the feeble light specimen imaging apparatus according to the second embodiment may have a closed container, serving as storing means, composed of a petri dish 51B, partition 52B and transparent plate 53B as shown in FIG. 29, wherein the specimen 1B may be retained on the petri dish 51B. The closed container includes an air supply pipe 54B that supplies $CO_2$ that has a constant temperature and low humidity and is produced by an unillustrated air-conditioning device into the closed container, and an exhaust pipe 55B that exhausts the $CO_2$ in the closed container, wherein at least one of the temperature, humidity, atmospheric pressure, and concentration of $CO_2$ in the closed container can be adjusted. Instead of supplying or exhausting $CO_2$, a heat seat may be provided in the closed container so as to electrically adjust the temperature or the like in the closed container.

The feeble light specimen imaging apparatus according to the second embodiment may have illumination unit for illuminating the specimen 1B. In this case, usable illumination unit include an illumination fiber that directs illumination light from a white light source or the like, an illumination device that realizes a critical illumination by combining a white LED and a single lens, an UCD for a microscope that is a Koehler illumination device using a condenser lens, etc. The feeble light specimen imaging apparatus according to the second embodiment may have an illumination device, as illumination unit, performing a differential interference observation or phase difference observation. In this case, a ring stop, prism, objective lens, or the like, which are exclusive, should be provided.

It is preferable whether the feeble light specimen imaging apparatus according to the second embodiment is formed into an erected type optical system or inverted type optical system is suitably selected according to the type of the specimen and purpose. The erected type provides an advantage that, in the observation of a slice of a tissue with the use of a membrane in order to achieve satisfactory contact to the specimen container, the observation from above by which the membrane is not in the way is easy to be performed. In the observation of a slice of a tissue, it can be said that the technique of continuously imaging the luminescent image for a long time while culturing for a long time the slice of the biotissue including a cell layer, which is preferably sliced into substantially one layer, is an extremely significant technique. Examples of the slice of the tissues include a central tissue such as cerebellum or suprachiasmatic nucleus, various organ tissues such as pancreas or tumor of organ. When the biological specimen is a small animal or insect having light transmittance, such as nematode, the biological specimen can be observed without being sliced. Because the feeble light specimen imaging apparatus according to the second embodiment also provides an optical system having a wide field of view, a biological specimen such as a small animal or insect holding a motion ability can be observed over a long time in the form of a nontoxic luminescent image by this apparatus, which is very advantageous. On the other hand, the inverted type provides an advantage that all of the imaging systems can be arranged below the specimen table when an observer wishes to measure the feeble light under a more strict light-shielding condition. Therefore, various works on the specimen table (e.g., replacement of the petri dish, injection of reagent or the like, or opening a cover for maintenance and check) can be carried out as optically separated from the works carried out above the specimen (with the state in which the influence by an external light is not given as much as possible), so that a constant imaging condition can be maintained.

Although the CCD is employed as imaging unit in the feeble light specimen imaging apparatus according to the second embodiment, the present invention is not limited thereto. For example, an imaging device such as a CMOS and having an imaging sensitivity equal to that of a CCD cooled to about 0° C. may be employed.

Additional Item of Industrial Applicability

The luminescent specimen imaging method, the luminescent cell imaging method, and the objective lens according to the present embodiment can preferably be used in a reporter assay in which a luminescent gene such as a luciferase gene is defined as a reporter gene so as to analyze a promoter or enhancer that controls the expression of the gene or to examine the effect of effecter genes such as a transcription factor or various reagents or the like.

Subsequently, the applicable range will be described based on the gist of the present embodiment.

Example of Cell and Specimen for Image Analysis

The system and method according to the present invention can easily be adopted to form an image of various optional cells provided in various manners according to the type of the substrate. Examples of cells include bacteria, protozoan, prokaryotic cell of fungi, or eucaryotic cell, and cells from birds, reptiles, amphibians, plants, mammals (e.g., primates (e.g., man), rodents (e.g., mouse, rat), rabbit, or ungulates (e.g., bovine, sheep, pig)). The cell can be a primary cell, normal and cancered established cell line, genetically modified cell, and cultured cell. The cells contain various established cell lines voluntarily induced, various established cell lines selected from individual established cell line with respect to a desired growth characteristic or responsiveness, and plural established cell lines induced from a different patient or a different portion, although the type of the tumor is similar. The cell is generally cultured in an incubator, which is controlled to contain atmosphere of 92 to 95% moisturized air and 5 to 8% $CO_2$ and to be, for example, atmospheric temperature of 37° C., in a sterilizing environment. The cell can be cultured in a nutrient mixture including a biological fluid such as fetal bovine serum in which an ingredient is not specified, or in a serum-free medium in which all ingredients are known.

The most interested factor is to form an image of a nerve cell and neural precursor cell. A genetically modified cell (e.g., recombinant cell) can be employed as the cell to be imaged. The particularly interested factor is to form an image of a biocell, but the present embodiment aims to express a cell membrane osmosis or fixed cell in the form of an image, according to the embodiment. An image of the cell is generally formed in a specimen containing a cultured solution of which aim is any one of keeping and growing the cell or both.

In many aspects (especially, the aspects including any one of a step of returning to the same field of view of the cell and a step of returning to the same individual cell in the same field of view of the cell or both) in the present embodiment, a cell is well fixed onto the surface of the substrate (e.g., a cell is deposited onto the surface of the substrate (e.g., the substrate coated with a material having an adhesion property to the cell)) so as not to move relative to the substrate even if the substrate is operated. For example, a cell is directly deposited on the substrate (e.g., a plastic for culturing a tissue in a well) so as to fix the cell relative to the substrate, whereby the substrate can be operated without moving the cell with respect to the substrate. With this, correct return to the same field of view of the cell and correct return to the same individual cell in the field of view of the cell are possible.

The present embodiment aims generally to form an image of a single cell level, especially to form an image of a living cell. A cell may be dispersed on the surface of the substrate as an isolated single cell. For example, a cell may be in contact with another cell like the case of a single layer, or may form a thin layer like the case of a slice of a tissue. A cell that is to be imaged may be a homogeneous cell population or heterogeneous cell population (e.g., mixed cell culture). As described above, the present embodiment is capable of forming an image of a single cell or forming an image of a cell population (the cell population may include plural different cells depending on the situation).

An image of a cell may be formed by utilizing a detectable marker (e.g., a fluorescent label or luminescent (chemiluminescent, bioluminescent) label), or without using these markers. The detectable marker or the technique of using the detectable marker together with a cell has been well-known in the field of this technique. Examples of the detectable marker include a fluorophore (or fluorescence) or chemiluminescent member, or other suitable detectable markers (e.g., marker used in an FRET (fluorescent resonance energy transfer) detecting system or a BRET (bioluminescence resonance energy transfer) detecting system), etc.

The system and method according to the present embodiment is capable of forming an image of a cell population and individual cell. In particular, the system and method according to the present embodiment is capable of forming a cell population or individual cell over time in order to observe a viability of a cell (e.g., survival ratio of a cell or health of a cell), physiological property of a cell (synaptic physiological property), signal transmission, position and function of organelle, position and function of protein (including interaction and turnover), enzyme activity, expression and position of receptor, change in the surface of a cell, cell structure, differentiation, cell division, or the like. For example, according to one aspect, the system and method of the present embodiment is used so as to determine whether or not the expression of protein (e.g., role of hunting in Huntington chorea) and a level change or agglomeration in protein causes a cell death, or used for determining whether or not they are the symptoms of the cell death (e.g., whether or not they are trials for preventing the cell death by the cell, not the causes of the cell death). The particularly interested subject is a research of neurodegeneration of a nerve cell that is being cultured.

The system and method of the present embodiment is capable of forming an image of a single cell or a population of a cell on a real time at an interval of a desired period, e.g., relatively short period.

The system and method of the present embodiment can quickly form an image of a cell (e.g., form an image of a cell positioned on the adjacent well), and further, the cell can be again imaged by returning to the same field of view of the cell including the same individual cell at an interval of relatively short period. Therefore, the system and method of the present embodiment can make an observation, which cannot absolutely be performed according to a conventional method due to the length of the time taken for acquiring each image or the like. In the present embodiment, a cell phenomenon (e.g., function of a cell, survival of a cell, destiny of individual cell in the population) can be traced at an interval of relatively short period. This contrasts with a conventional study of immunocytochemistry in which only an image taken at a specific point can be obtained, information amount obtained about an advancing phenomenon (e.g., degeneration) is limited, and much time is needed. Specifically, in order to analyze neurodegeneration of 300,000 cells in the conventional study of immunocytochemistry, about six weeks are generally needed. However, by using the system and method of the present embodiment, the same analysis can be completed in the time far shorter than six weeks. When the system and method of the present embodiment are used, the work for an immunocytochemical analysis or an analysis using a microscope, which generally takes six full days if manually done, can be completed within one hour with the process of a microscope and computer.

In the system and method of the present embodiment, even when the substrate is taken out of the system, and then, again mounted to the system, the same cell population and individual cell in the cell population can correctly be specified, whereby a single cell and selected cell population can be analyzed over a long period (e.g., several hours, several days, several weeks, or period more than these).

The system and method of the present embodiment can qualitatively or quantitatively measure plural biological variables (e.g., parameters or variables of a cell function) substantially simultaneously or completely simultaneously. For example, when a cell is imaged by using a phase difference together in the system and method of the present embodiment, information relating to the change in a form of a cell or various phenomena in molecule can further be obtained. According to another aspect, in the system and method of the present embodiment, a cell can be imaged by using plural detectable markers.

Application Examples of System and Method of Present Embodiment

The system and method of the present embodiment is applicable to various settings employing a wide variety of cells. In the system and method of the present embodiment, a cell or cell population during when a tissue is cultured can be traced over an optional desired period (e.g., two hours, five hours, twelve hours, twenty-four hours, two days, four days, six days, seven days, several weeks, period to the lifetime of the cell of interest). A biological specimen represented by a cell can be imaged at an interval of a fixed period corresponding to the above-mentioned period or with another embodiment. The examples of the image formation will be described below. The present embodiment is not limited to these examples. In the examples, the specific advantages and features of the present embodiment are emphasized.

Image Formation of Cell for Preventing or Reducing Phototoxicity

Phototoxicity always becomes an important limiting factor when forming an image of a living specimen. The phototoxicity is directly related to an intensity of incident light, irradiation time, and wavelength. When a process that is gradually advancing is examined, the same cell specimen should be repeatedly irradiated. Therefore, the phototoxicity becomes a problem. In view of this, the amount of incident light necessary for detecting a usable signal is reduced by employing the system and method of the present embodiment. In the present embodiment, the phototoxicity is significantly reduced with several methods. According to the system and method of the present embodiment, a microscope is focused by irradiating a white light having a low intensity in an extremely short period, and then, a light with a high intensity is irradiated, whereby a fluorescent image having high resolution can be acquired. When an automatic focusing is not performed, the focus is adjusted by continuously irradiating fluorescence having high intensity. However, considering the time taken for the focusing of a microscope and the time taken for acquiring an image afterward, a cell might be irradiated with a high-intensity light having phototoxicity for a long time that is longer than that in the case of automatic focusing by one figure.

In the system and method of the present embodiment, after a focus is adjusted, plural adjacent fluorescent images are obtained without performing refocusing, so that they are advantageous for reducing phototoxicity. In the system and method of the present embodiment, most of the field of view of the cell receives a light necessary for the formation of an image as a significant light. Therefore, it can be said that the system and the method is optimized for acquiring a fluorescent image. Finally, in the system and method of the present embodiment, the irradiation time of the high-intensity light is substantially reduced by automation, whereby light discoloration hardly occurs, and the excited time required for forming a high-resolution image is further reduced, because the emitted fluorescence is bright.

Optical Imaging of Gene Expression by Stimulus

The present embodiment can be embodied as described below.

For example, a reporter gene (preferably, a luciferase originated from a firefly or Renilla) expressibly linked to a promoter region of a gene to which an expression is induced by a stimulus caused by the contact between a substance to the cell is transduced into a predetermined number of cells (e.g., 1 to $1 \times 10^9$, preferably $1 \times 10^3$ to $1 \times 10^6$) by using the gene transducing method described above. Next, the predetermined number of cells to which the reporter gene is transduced is cultured in a desired nutrient culture medium (e.g., D-MEM medium) by using a desired instrument that can culture the cell (e.g., petri dish, multiplate having many wells, etc.). Then, the specimen composed of the predetermined number of cells is placed onto a moisturized culture device section of a luminescent microscope that is kept beforehand at a temperature (e.g., 25 to 37° C., preferably 35 to 37° C.) that is optimum for the cell, and into which water is injected to prevent the specimen from being dried, and then, a luminescent image is recorded with a digital camera through an objective lens at a specimen observation section of the luminescent microscope. Next, a substance (e.g., compound), which is brought into contact with the cell to cause a stimulus, is added to the specimen in a desired concentration (e.g., 1 pM to 1 M, preferably 100 nM to 1 mM), whereby the luminescent image of the specimen is recorded at a desired time interval (e.g., five minutes to five hours, preferably ten minutes to one hour). Then, the brightness value in the desired area of the recorded luminescent image is acquired by using commercially available image analysis software (e.g., MetaMorph (trade mark) by Universal Imaging Corporation).

When the present embodiment is configured to image and record a bright field image in the field of view same as that of the luminescent image, the image analysis software further has a function of superimposing the luminescent image and the bright field image. Therefore, in the unclear luminescent image due to a cell or the like that rapidly moves unexpectedly (e.g., whole tissue, specific cell population, individual cell, some regions of a cell), the cell or the like can correctly be recognized by utilizing a clear image such as the bright field image. Thus, the present embodiment provides an advantage that the reliability of the analysis can stably be maintained. The image analysis software for carrying out the image analysis using the imaging method and apparatus according to the present embodiment has a recognizing function for recognizing an individual cell or the like (whole tissue, specific cell population, individual cell, some regions of a cell) in at least a luminescent image according to outline information based on a parameter such as a shape or size, and a measuring function for measuring a light emission amount emitted from the recognized cell or the like, and preferably has a function of outputting a result of the measurement, according to the instruction, from a computer controlling the imaging apparatus or from input means (keyboard, mouse, ten-key, touch panel, etc.) operated by an operator. The result of the measurement is preferably output as associated with the image information such as the recognized cell or the like. The output form can be a dummy image or numerical value according to the light emission amount. When a large number of cells are analyzed, the output form may be a graphical expression such as a normal distribution, histogram, line graph or bar graph. When the result of the time-series analysis relating to the same cell or the like is output, the output form may be a dot distribution in which the light emission quantities are dotted in the order of the lapse of time or a waveform pattern in which the light emission quantities are linked with line in the order of time. The waveform pattern is particularly suitable for luminescent data exhibiting periodicity such as a clock gene. The image analysis software may be configured to analyze the output graph or the waveform pattern singly or the correlation with the other cell or the like. Further, the image analysis software preferably includes a recall function for displaying the image of the corresponding cell or the like onto the display, when the interested area in the result of the analysis output on the display is designated through the input means. The recall function preferably includes a showing mode in which the moving image information relating to the designated cell or the like during the whole imaging period or during the specified period is shown.

Image Formation of Biocell Over a Long Period

A biocell is mostly cultured on a plastic for a tissue culture. When a biocell is examined, especially when a biocell is examined in a gradually advancing process, it is necessary to maintain the health of the biocell (e.g., nerve cell) over a period sufficient to cover the examined process. Ideally, if the cell is imaged on the culture dish that is the same dish on which the cell is originally grown with a fixed time interval, the health of the cell is maintained, and the degree of disturbance can be minimized. The cell on the dish for the tissue culture can be imaged by using an inverted microscope under a sterilizing condition. However, in the case of the inverted microscope, the image is formed through the substrate (e.g., glass or plastic) on which the cell is grown. Depending upon a wavelength (e.g., ultraviolet ray), the plastic used for culturing a tissue is poor in transmittance, and generates light scattering, compared to a glass, so that the image resolution might be reduced. However, even in case where the substrate is coated with polylysine and laminin so as to promote the deposition and differentiation of the cell, most of the cells represented by a nerve cell survive for a long time, and show healthy appearance, when they are grown on the plastic for culturing a tissue, compared to the case in which they are grown on a glass. Therefore, the object of the present embodiment is to provide a system having an optical system capable of forming a high-quality image, regardless of plastic or glass through which light is transmitted.

When an image is automatically acquired through a glass or plastic, a significant influence is given to an objective lens that can be used. Specifically, an immersion lens generally converges a lot of lights than a non-immersion (air) objective lens, but the immersion lens needs an immersion solvent. Supplying the solvent is unrealistic in the case of the automatic imaging. There are many problems in the operation for focusing by using the non-immersion lens through the substrate having various compositions and thickness. The refractive indexes of these substrates vary for every product, and are different from the refractive index of air through which the emitted fluorescence pass until it is converged to the objective lens. When an image is formed through a substance having a different refractive index, a chromatic aberration and spherical aberration occur. The numerical aperture of the lens is increased due to the aberration. The aberration is made visible in the case of ×20, becomes substantial in the case of ×40, and is hardly eliminated in the case of ×60. Finally, some specimens are present relatively apart from the bottom surface of the tissue-culturing dish, such as a cultured brain slice, and hence, it is necessary to acquire an image from various planes along a Z-axis by using an algorithm that automatically determines a focal plane. In this case, it is preferable to apply an optical deconvolution function to the luminescent image data of the present embodiment. By adopting the optical deconvolution function, a three-dimensional image can be formed based on not only a slice but also a biotissue or small creature (e.g., inset, animal, plant). In the three-dimensional image, plural specimens such as cells or the like superimposed with one another on a detection optical path can easily be identified, and further, different specimens, each being present at the position corresponding to the different distance on the detection optical path, can be quantized with high precision.

When an objective lens having a long focal distance is used, focus can be adjusted to an object that is far from the objective lens, which can prevent the objective lens and tissue-culturing plate from colliding with each other during the automatic focusing.

High-Throughput Screening Assay

The system and method of the present embodiment is particularly useful for performing a high-throughput screening assay. Examples of the assay include an identification of a substance that causes a desired response of a cell (e.g., adaptation of a cell death, internal transfer of a receptor, adaptation of activity in signal transmission path (rise or fall), adaptation of transcription activity), or analysis of a nucleic acid having a function that has not yet been found or examined (e.g., analysis in which a coding sequence of a subject of interest is transduced into a target cell, and expressed in the cell), but the present invention is not limited thereto.

When plural parameters are evaluated, markers that can be distinguished in the detection can be used to detect different variables. For example, when the screening assay includes the evaluation of the affect of the gene product coded with a polynucleotide, one type of marker is used to identify the cell that is transfected with a subject construct (e.g., a cell that is transfected with a construct of a subject of interest by using a detectable marker coded in the construct containing polynucleotide that is the subject of interest, or by using a detectable marker present on the construct transfected simultaneous with the construct of the subject of interest), a second marker is used to detect the expression of the gene product (e.g., a gene product in the detectable marker, which is provided by a fused protein produced from a gene product coded with the polynucleotide), and a third detectable marker is used to evaluate the affect of the gene product to the target cell (e.g., the viability of the cell is evaluated by the expression of the reporter gene that is under the control of the promoter, which is assumed to be adapted by the gene product of the candidate polynucleotide, or by the factor adapted by the gene product of the candidate polynucleotide). The information relating to the change in the cell form (e.g., differentiation of a cell or formation of cell structure (e.g., dendrite)) can be obtained from the phase difference image. In this case, the phase difference image is superimposed on the fluorescent image that is acquired at an interval of a predetermined selected time for every cell for comparison.

In another example for identifying a substance that modifies the activity of a receptor on a target cell by a screening assay, a bond to the receptor of the substance can be detected by using a first marker, and the activation caused by the transcription of the reporter gene can be detected by using a second marker. When used in the present embodiment, the "detectable marker" includes a molecule that emits a detectable signal when excited with a predetermined wavelength.

In the present embodiment, a cell is individually detected qualitatively or quantitatively by using plural fluorescent markers in the same assay so as to simultaneously detect or measure the plural cell responses. Many quantitative techniques for utilizing a unique characteristic of a fluorescence have been developed, and examples of these techniques include a direct fluorometry, fluorescence resonance energy transfer (FRET), fluorescence polarization method or anisotropic method (FP), time-resolved fluorometry (TRF), fluorescence life-time imaging microscopy (FLM), fluorescence correlation spectroscopy (FCS), fluorescence recovery after photobleaching (FPR), etc. The subject of interest is a marker technique that is applicable to a biocell and can be used at a desired time interval (e.g., in which the comparison between images taken at an interval of several hours or several days can be carried out) depending upon the situation. The present embodiment can change the assay using the fluorescence to an assay using a luminescence that does not need photo-excitation. If the photo-excitation is unnecessary, an optical device can be simplified, and further, measurement data that is sufficiently bright and has excellent quantitative property can be obtained at a suitable magnification under the aforesaid optical condition.

Polypeptide as Specimen

Depending upon an aspect, the specimen is "polypeptide" or "protein". These words are interchangeably used, and indicate a polymer amino acid. Examples of the polymer amino acid include genetically coded amino acid and genetically non-coded amino acid, chemically or biochemically modified (e.g., modified after translation or glycosylated) amino acid, modified amino acid, polymer polypeptide, or polypeptide having a modified peptide skeleton. Examples of "polypeptide" that can be subject to screening include the one that is an effusion protein and has a heterologous amino acid sequence, the one fused with a heterologous and homogenous reader sequence, the one having or not having N-terminal methionine residue, an immunologically tagged protein, etc. The modification to polypeptide can be carried out in order to promote the deposition onto a base material (e.g., solid phase carrier such as beads, porous substrate, capillary array). When the base material described above is used, a substance in a trace amount can be detected with a high surface area or microvolume. When the polypeptide is not taken into a cell, the polypeptide can be transduced into the target cell by a microinjection, for example.

Cell used for Screening Assay

The aforesaid cells can be used as a cell suitable for use in the screening assay in the present embodiment. Depending upon an aspect, the subject of interest is to make the assay and assay method of a recombinant cell that expresses a target gene product suitable for the detection of a candidate substance that causes an interaction with the target gene product by, for example, the bond to the target gene product, adaptation of the expression of the target gene product, or the adaptation of the biological activity of the target gene product. In the present specification, the "target gene product" means various gene products represented by a protein that is a heart of the screening of the candidate substance, but is not limited thereto. For example, the target gene product is defined as a receptor, and the assay can be adapted to the identification of the substance for modifying the activity of the receptor.

Ordinary Assay

A material and a cell are brought in contact with each other in a process in an assay, regardless of for what purpose the screening assay is carried out. In the case of a genetic material, a material is transduced into a cell, and a detection is executed for one or more variables of the cell in this process. A change in the read value of the cell parameter corresponding to the material is measured, standardized if possible, and the resultant parameter is compared to the read value for identification, whereby evaluation is done. In this evaluation, the result of the reading for identification, the basic read value obtained under the presence and absence of various factors, and the read value obtained by using the other materials (that may contain or not contain a known inhibitor in a known path) or the like can be used. Examples of a material to be analyzed include a molecule having an optional biological activity provided with an ability of directly or indirectly adjusting the subject cell parameter of the subject cell.

It is convenient to add the material into the culture solution of the cell, which is being cultured, in a form of a solution or easily-soluble form. The material can be added to a flow-through system in a form of intermittent or continuous stream. A compound can be added all at once or gradually added in a small amount in a static solution except for the time of the addition. As one example of the flow-through system, two types of fluids are used, wherein one of them is physiologically neutral solution, while the other is the same solution to which a test compound is added. The first fluid passes onto the cell, and then, the second fluid passes. In the method using only one type of solution, the test compound is added all at once in the culture solution in a specific amount around the cell. The total concentration of the component of the culture solution should not significantly vary due to the addition of the test compound or between two types of solutions in the flow-through system.

Depending upon the aspect, the composition of the material does not contain the ingredient (e.g., preservative) that can significantly affect the total composition. In this case, the composition of the material is essentially constituted by a material to be tested and a physiologically allowed carrier (e.g., water, cell culture solution). In another aspect, another material can be contained in the screening assay. Examples of the materials include a material that makes a static bond to the bond partner of the material possible, a material for reducing a nonspecific interaction or an interaction at a background, etc. It is naturally necessary to select the one, among these materials, adapted to the screening of the biocell.

As described above, plural assays employing different material concentration are simultaneously executed, whereby a differential response corresponding to various concentrations can be obtained. As is known in the technical field, a concentration within a certain range obtained by the dilution with the use of a scale of 1:10 or other logarithmic scales is used in order to determine the effective concentration of the material. This concentration can finely be controlled by performing the second series of dilution, according to need. In general, one of the concentrations plays a role of a negative control, wherein the negative control is set to a zero concentration, a concentration less than a detection level of the material, or a concentration not more than the concentration of the material that cannot provide a change by which a phenotype can be detected.

The example of the assay utilizing various aspects and features of the system and method of the present embodiment will be described below. The present embodiment is not limited to these examples.

Medicine Screening Assay

The image-forming system and method according to the present embodiment is adapted to a variety of assay systems, wherein a screening can be performed relating to a desired biological effect (e.g., adaptation of subject cell parameter) given by the candidate material to the target cell. The biological effect can be made to have a meaning when the material is used as a medicine. For example, the various materials can be examined with respect to the adaptation such as the differentation of a cell, cell death (e.g., modulation of apoptosis), signal transmission (e.g., signal transmission in a G-binding protein receptor, GTP bond, detection of the second messenger), activity of ion channel (e.g., by the evaluation of influx by means of calcium image-formation), transcription (e.g., a material affected to the expression of the target gene product is identified by using, for example, a reporter gene assay). The subject of interest is the assay that can be used together with a biocell.

In one aspect, the screening assay can be a binding assay that detects a bond to a bond partner of a candidate material in a cell, for example, the screening assay can be a screening for identifying a material acting as an agonist or antagonist ligand to the receptor. In a specific aspect, the assay can be an antagonist binding assay for evaluating a candidate material with respect to the inhibition of an activity of, for example, a known receptor ligand (e.g., known agonist or antagonist). In the latter aspect, the known ligand can be tagged so as to be detectable, and the detectable marker of the known ligand can be reduced with the reduction of the activity of the known ligand or bond.

When the candidate material is incubated with the target cell, the culture can be performed at an optional appropriate temperature, i.e., 4 to 40° C. in general. The incubation time is selected so as to make the activity optimum. The time optimum for progressing a rapid high-throughput screening can be selected as the incubation time. 0.1 to 1 hour is generally sufficient for the incubation time, but depending upon the aspect, it may be desirable that a cell is examined at an interval of this culture period or a longer suitable period.

The inventors have found that the variation pattern in the expression of the gene varies in plural cells cultured in the same petri dish. According to the optical condition pursued by the inventors, it has been found that a cell image, which can be formed within 1 to 5 minutes and can be subject to an image analysis, can be provided when the optical condition of the objective lens in the imaging apparatus represented by "square of numerical aperture (NA)/projection magnification ($\beta$) is not less than 0.071. A luminescent analyzing system for microscopically observing the luminescent image by a storage-type imaging apparatus is referred to as a luminescent microscope. The luminescent microscope preferably includes light-shielding unit provided with an opening/closing lid (or opening/closing window) for shielding light. A necessary biological specimen is set or replaced by opening or closing the light-shielding unit. According to a purpose, an operation for exerting a chemical or physical stimulus on a container storing the biological cell may be carried out manually or automatically. In the most preferred form, the luminescent microscope has mounted thereto a known or own culture device. The culture device has a function of keeping the optimum temperature, moisture, pH, open-air component, component of culture medium, and component of culture solution in order to make a long-time analysis in the system possible.

Examples of the biological specimen that is the source of the luminescent specimen include eucaryote, cell or tissue derived from cyanobacterium, etc. In a medical use, a specimen containing a cell excised from a region to be examined of mammals (especially, man) by a biopsy is particularly illustrated. In a regenerative medicine, a biological specimen having at least one region artificially modified or synthesized is particularly illustrated, wherein this specimen can be utilized for checking as to whether the biological activity is satisfactorily kept or not. In another aspect, the subject of the assay in the present embodiment can be not only a cell or biotissue derived from animals but also a cell or biotissue derived from plants or insects. In the assay, a bacillus or virus can be analyzed by every portion in the container, which cannot be executed by a conventional luminometer. In the luminometer, a countless specimen (e.g., not less than one million per one well) is superimposed in the container such as a well or petri dish, whereby a great light emission amount can quickly be obtained. In the present embodiment, an image of an individual luminescent specimen, which cannot be seen by naked eyes, is formed, so that the individual cell or biotissue can be analyzed even if the specimens are stored in the container with a density to such a degree that the individual cell can be identified. The individual analysis described above includes an analyzing method in which only a luminescent cell is statistically totaled or averaged. Accordingly, the proper evaluation relating to the interaction per one cell can be carried out. In a large number of mixedly present luminescent specimens, a cell population or tissue region having the same light emission amount or luminescent pattern can be identified.

Additional Supplementary Explanation of Terms in First Embodiment and Modification Examples of the specimen container for storing the specimen 1A include a petri dish, slide glass, microplate, flow cell, etc. The bottom of the container is naturally made of a light-transparent material (glass, plastic, etc.), and further, it is preferable that the container has a wide (or flat) bottom surface in order to easily acquire two-dimensional data. In a well or cuvette in which plural storing sections are integrated, the whole partitioning portion of each storing section is preferably formed of a light-shielding material or dye. It is preferable to provide a lid for preventing evaporation on the container, such as a petri dish, having an upper opening. Further, an anti-reflection coating or dye is preferably applied onto the inner surface of the lid so as to enhance an S/N ratio. Instead of the hard lid, a liquid lid such as mineral oil may be arranged at the upper surface of the specimen in the container. The specimen stage on which the specimen container is placed may be moved in the X-axis direction and Y-axis direction in order to change the field of view for another imaging, like a normal microscope apparatus, according to need.

The objective lens 2A may be arranged in an inverted form below the specimen 1A. The objective lens 2A may be heated by appropriate heating unit (e.g., Peltier device, warm air heater) in order that the living luminescent specimen stably functions under a thermostatic environment such as a culture condition. The objective lens 2A may further be configured to be driven in the Z-axis direction (vertical direction in FIG. 26) that is the optical axis direction. The objective lens 2A has the Z-axis driving mechanism of the objective lens, wherein the objective lens 2A is automatically driven along the Z-axis (optical axis direction). A rack and pinion mechanism or friction roller mechanism are employed as the Z-axis driving mechanism of the objective lens.

The objective lens 2A may be formed appropriately into an immersion type according to a desired magnification. Which magnification is selected is optionally set according to the size of the specimen to be evaluated (or analyzed). Specifically, the desired magnification can be a low magnification (e.g., ×5 to ×20) to such a degree that a cell or tissue can be observed, or can be a high magnification (e.g., ×40 to ×100) to such a degree that an intracellular or extracellular micromaterial can be observed.

It is preferable that the CPU 5A has a configuration for displaying image information of the luminescent specimen in a form of a moving image, so that the CPU 5A provides an analyzing method of observing a change in an activity of one or more desired cells with a real-time image. Thus, the luminescent condition per cell or per tissue can be observed in a time-series manner with an image having a sense of reality.

In the present embodiment, the method and apparatus for the time-series observation may be provided in the form of software that controls the required devices or cooperates with them, or in the form of a computer program that features the software. The method and apparatus according to the present embodiment can be electrically connected to a database that is set in the apparatus or set separately from the apparatus, whereby the analyzing result having high reliability and high quality can be provided with high speed without being restricted by an image capacity or amount of analysis information.

In the present embodiment, a luminescence (cold light) by a substrate solution as a chemically excited reagent is employed, whereby the structure for irradiating excited light is unnecessary in the detection process. In the observation using a microscope, an objective lens having a high numerical aperture is used for a luminescent specimen emitting a feeble light that cannot be seen with naked eyes, whereby the luminescent specimen can be imaged with high speed without employing a large-scale and expensive ultracooled CCD that needs to be cooled to a very low temperature (e.g., −3 to −60° C.) using a liquid nitrogen. Specifically, the apparatus in the present embodiment has, as major components, an objective lens having a high numerical aperture (high NA) and a projection magnification by which a subject is put in the observation field of view; an imaging device (e.g., CCD, CMOS) that can continuously function near a slightly low temperature (e.g., −5° C. or more) or near a room temperature (or temperature in the apparatus); holding unit for holding the subject at the position suitable for the image formation; and light-shielding unit that houses the objective lens, imaging device and holding unit so as to secure the shield of light during the image formation. When the CCD is compact and can be controlled under a slightly low temperature, the whole apparatus can be made compact, and can be designed to have a height by which a user can look down the apparatus on a desk, even if all components are stored in the same housing. Therefore, the apparatus embodying the present embodiment becomes very compact with low cost. The space in the apparatus has reduced volume due to the miniaturization, whereby the biological environment (temperature, moisture, air component) condition in the apparatus is likely to be regulated to a level suitable for the culture and microreaction. Accordingly, the apparatus has more reduced cost and high reliability. The height of the whole apparatus is reduced, with the result that the placement or removal of the luminescent specimen or stimulus process of dispensing a medicine to the specimen stored in the apparatus can easily be carried out through the suitable opening/closing window or opening/closing cover from above the apparatus.

On the other hand, the present embodiment provides a method and apparatus for forming an image with a large number of pixels (preferably many pixel number) without performing an optical scanning. In the image analysis of the formed image, image analysis software for analyzing a cell can be an industrially applicable product, singly or in a total system of a luminescent microscope, as a part of the present embodiment.

The description below relating to a high-throughput imaging apparatus is included as a single component or in combination with the embodiments described above. In the description below, the other method and apparatus that can share the content described below is not limited to the gist of the present embodiment, but includes the description of dividable embodiments.

Technical Field of High-Throughput Imaging Apparatus

The present embodiment relates to an imaging apparatus that images a large number of imaged regions, set in one or more biological specimens, in a time-lapse manner. Particularly, the present embodiment relates to a high-throughput imaging apparatus that enables a high-throughput imaging. Further, the present embodiment relates to software including a program that causes the imaging apparatus to execute the functions thereof. The preset embodiment is suitable for a research or clinical use for efficiently examining in large numbers a biological activity of a biological specimen such as a cell derived from organisms.

Background Technique of High-Throughput Imaging Apparatus

Because an organism has high complexity, it is not so easy to understand a structure and function. Therefore, a simple experimental system using a cell (i.e., cultured cell), which is the minimum unit that can reproduce a life phenomenon, is used. The use of the cultured cell enables the experiment relating to the analysis of response of hormone, which is not affected by the in-vivo other factors. Specifically, a functional analysis of a gene can be executed by a transduction or inhibition of a gene.

In order to culture a cell, it is necessary to set an environment similar to the in-vivo environment. Therefore, a medium that has a temperature of about 37° C., which is a body temperature, and is similar to intercellular fluid, is employed. The medium includes not only a nutrient source such as amino acid but also a carbonate buffer for PH control. The carbonate buffer is in equilibrium under the presence of air containing carbon dioxide having high partial pressure of 5%, and is used for an open culture such as a dish. A high-humidity environment of 95% to 100% is required in order to prevent the evaporation of water content from the medium.

A carbon dioxide incubator provided with the environmental conditions described above is used for culturing a cell. A phase-difference microscope or a differential interference microscope is used for observing the state of the cell, and a fluorescent microscope is used for observing an expression of GFP. A CCD camera and a controller (personal computer) are used for imaging and displaying a microscopic image, and a culture microscope formed by combining these microscopes has been proposed (Patent Document; JP-A-2003-29164).

Problem to be Solved in High-Throughput Imaging Apparatus

When a cell that is being cultured is observed with a microscope for a long time or over a long period, the cell is observed in a time-lapse observation manner, and the image of the cell is acquired in a time-series manner. The time-lapse is used for enabling an easy confirmation of the state of the cell, which changes over a long time, by imaging the specimen at a fixed time interval and storing the images. For example, one cell is imaged once in a required imaging time (exposure time of a camera), and then, the cell is imaged once in one hour. If the imaging of the cell is continued for 24 hours, 25 images can be obtained. After these images are obtained, they are continuously reproduced, whereby the change of the cell for every an hour can easily be confirmed. If the imaging interval is reduced to, for example, 30 minutes or 15 minutes, a cell that moves quickly can be observed.

When plural regions of a cell are to be observed, a microscope or a specimen is moved to a target position by using an electric stage attached to the microscope, and the observation is carried out. The movement to the observation position is done in synchronism with the time-lapse. The time-lapse in which plural observation positions are sequentially observed is referred to as a multipoint time-lapse. According to the luminescent specimen imaging method and the luminescent specimen imaging apparatus according to the present embodiment described above, a luminescent image can be formed in a remarkably shorter time (e.g., the required time of 1/30 or less), compared to the conventional case, by employing an objective lens that is originally discovered and has a bright numerical aperture. Therefore, a time-series evaluation with a feeble light image at an interval of 5 to 20 minutes, at an interval of less than 5 minutes under a preferable condition, and at an interval of about 1 minute at the shortest, can be realized. This makes it possible to use a luminescent image, which cannot be seen with naked eyes, as a substitute for a fluorescent image, which can be observed with naked eyes, or to use a luminescent image in cooperation with a fluorescent image. Therefore, the present embodiment provides an epoch-making technique that can be utilized for an analysis of a high-speed reaction or kinetics of a biomolecule. An excited light is unnecessary for obtaining a luminescent image. Therefore, a photosensitive test such as a circadian rhythm is naturally realized, and further, a correct and stable analysis for a long period is realized without eliminating an excessive stimulus or damage to a biological material. In a regenerative medicine, there is a possibility that the analysis using a luminescent image makes it possible to perform a therapy, diagnosis, drug discovery, or the like using a biomaterial having no biological damage.

However, when an imaging based on a time-lapse is to be carried out for a large number of cells, quite a few significant time difference might be produced between the cell that is imaged at the beginning and the cell imaged at the end. The significant time difference is frequently fatal when making a comparison between cells. There has not been found an effective method of imaging plural cells, optionally designated, so as not to produce a time difference. Conventionally, an imaging interval is manually changed so as to sequentially image plural cells, and if a malfunction occurs, the apparatus is stopped to try again. In a system in which a large number of cells are automatically analyzed, like a current cell-based assay, a throughput might be decreased sharply when an image based upon a time-lapse is used.

The application example in which the method and apparatus according to the present embodiment is improved so as to achieve an efficient time-lapse imaging operation in view of the aforesaid circumstance will be described below. The high-throughput imaging apparatus and software for the same described below are excellent inventions having patentability based on the gist of the present embodiment. The embodiments described below aim to provide the high-throughput imaging apparatus and software for the same capable of simultaneously obtaining time-lapse data from a large number of subjects to be imaged.

Unit of High-Throughput Apparatus for Solving Problem

In order to attain the foregoing object, the high-throughput imaging apparatus according to the present embodiment includes an image acquiring unit for acquiring an image of a specimen by imaging a biological specimen present at plural imaging regions; and a control unit for controlling the image acquiring unit so as to execute a time-lapse interval imaging for every imaging region, wherein the control unit has an interval imaging condition setting unit for setting a condition of an interval imaging based on the imaging time required for acquiring the image of the specimen and the number of the imaging regions. The condition of the interval imaging includes, for example, changing the imaging time, which is the time-lapse condition, according to the speed of the activity or the reaction speed of the biological specimen. According to the high-throughput imaging apparatus of the present embodiment, an appropriate exposure time can be selected from an exposure time of 1 to 20 minutes or an exposure time more than that. For the specimen whose reaction (or activity) speed is fast, the minimum exposure time can be set within the range in which a luminescent image by which an image analysis can be made can be set. On the contrary, for the specimen whose reaction (or activity) speed is slow, an exposure time that is long to such a degree that an image capacity is not surplus can be set. Preferably, an exposure time of plural stages (e.g., stage of optional combination of two or more from the group consisting of 1 minute, 5 minutes, 10 minutes, 20 minutes, and 30 minutes) or a continuous time range (e.g., optional exposure time selected from a divided scale of 1 to 3 minutes increments or selected steplessly, in an exposure time of 1 to 30 minutes) is set in the same or different imaging field of view, whereby an image analysis for every specimen or every region (or portion) in the specimen can be executed. In the luminescent image having different reaction (or activity) speed, the reproduction speed by an image reproduction unit is controlled, with the result that a moving image with a similar speed can be artificially provided. Therefore, the evaluation such as a diagnosis can be made simple and efficient. Even when there is a nonspecific variation for every specimen, the specimen can correctly be analyzed, so that there is an advantage that a final evaluation result can quickly be given. The minimum exposure time within the range in which the luminescent image to such a level that the image analysis is possible is acquired can be set for every specimen, whereby the analyzing time can be shortened, and the throughput can be enhanced. The exposure time may be selected manually or automatically.

The high-throughput imaging apparatus according to the present embodiment has an image acquiring unit for acquiring an image of a specimen by imaging a biological specimen, which is present at plural imaging regions, by an image information extracting unit that extracts different image-related information; and a control unit that controls the image acquiring unit so as to execute a time-lapse interval imaging for every imaging region, wherein the control unit has an interval imaging condition setting unit for setting an interval imaging condition based on the imaging time required to acquire the image of the specimen and the kind of the image information extracting unit. In the configuration described above, the imaging operation is efficiently executed under the imaging condition set by the control unit, whereby a large number of imaging regions can be imaged in a short period.

In the present embodiment, any organisms can be defined as a subject of the "biological specimen". The biological activity of interest is retained in an appropriate container or organism, serving as a holding unit, in a retainable state, whereby the imaging region to be imaged can be provided to the imaging unit. The container includes any storing members capable of retaining the specimen in a state in which the specimen can be imaged by desired imaging unit. Specific examples of the container include a well, petri dish, slide chamber, cuvette, etc. Examples of the organism include plants, mammals, fish, insects, bacteria, and virus. If a part of the organism is processed according to need so as to be capable of being imaged in the state in which the organism keeps its life, and the imaging region of the organism can be accessed by a suitable imaging unit, the biological specimen is retained in the organism. The biological specimen includes any regions derived from organisms. Preferably, the biological specimen is a biological cell, and more preferably, the biological specimen is a nucleated cell that can be embryologically fusioned or grown. The organism in which a cell constructs plural organs separated into different functions may be an optional organ exhibiting a biological activity of interest. The biological activity can be one or more of physiological, genetic, immunological, biochemical, and hematological activities. The "plural imaging regions" mean one or more biological specimens retained by the same holding unit or one or more kinds of regions to be imaged retained by the different holding units.

Effect of High-Throughput Imaging Apparatus

As described above, the high-throughput imaging apparatus according to the present embodiment efficiently executes the imaging operation under the imaging condition set by the control unit, whereby a large number of imaging regions can be imaged in a short period. A large number of time-lapse data pieces can simultaneously obtained, even if the number of the specimens is very large, so that the high-throughput imaging apparatus greatly contributes to the research or medical treatment involving a biological activity.

Figure 30:
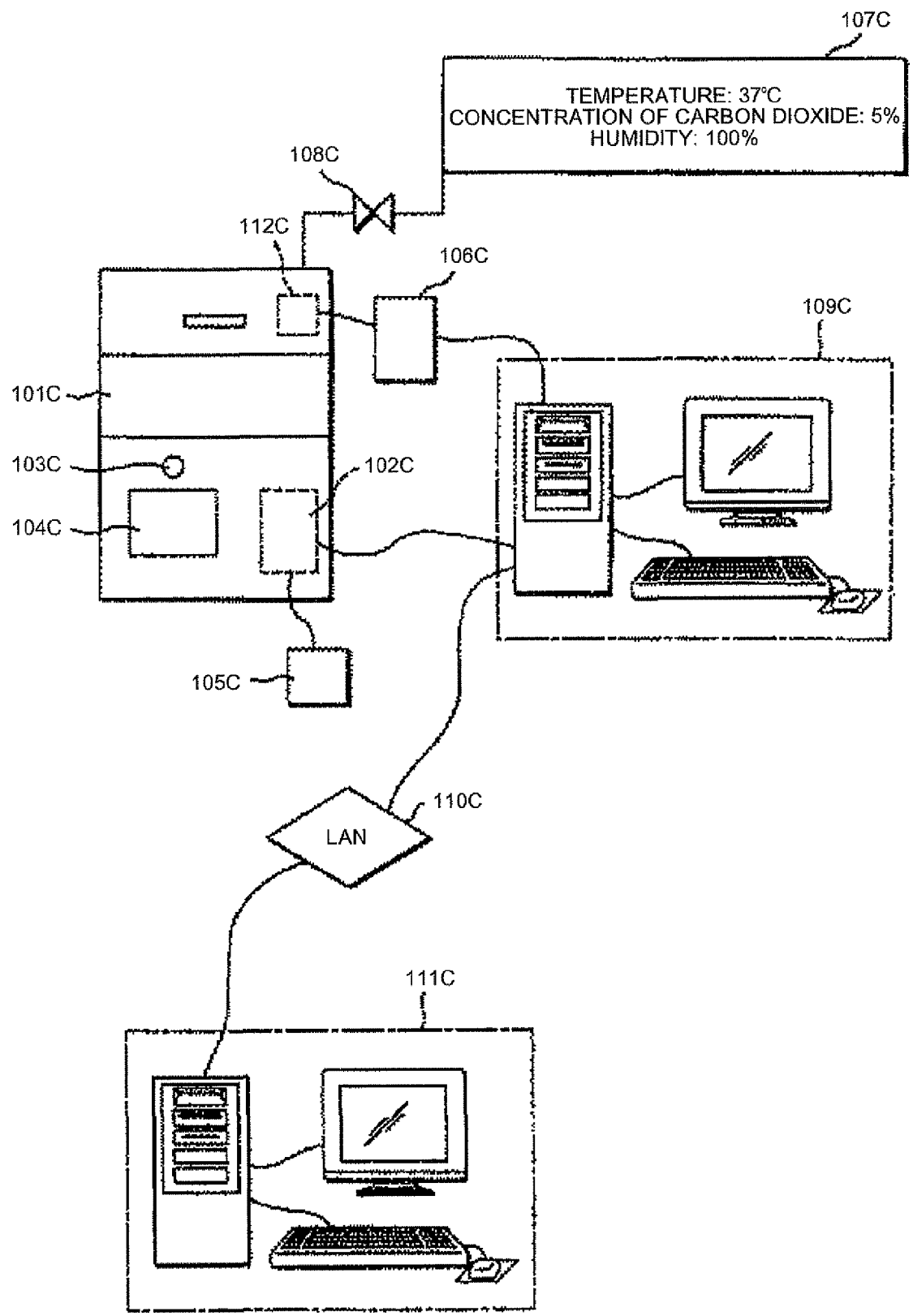
FIG. 30 is a conceptual view for showing the overall configuration of a high-throughput imaging apparatus that is an application example of the present embodiment.

A first example of the present embodiment will be explained with reference to FIG. 30. FIG. 30 is a conceptual view for showing an overall configuration of the apparatus according to the present embodiment. A main body 101C of a culture microscope is formed by integrating an incubator chamber in which a cell is cultured and a microscope portion for observing the cell. The main body 101C of the culture microscope has incorporated therein a controller 102C that controls later-described units. The controller 102C is arranged in the main body 101C of the culture microscope so as to make the space of the culture microscope compact. However, the controller 102C may be arranged outside of the main body 101C of the culture microscope when there is an influence of heat generated from the controller 102C. The main body 101C of the culture microscope includes an alarm buzzer 103C and an alarm display device 104C. The alarm buzzer 103C can make an alarm sound when a trouble occurs during an experiment. The alarm display device 104C can display an alarm, an instruction of operation or the like when a trouble occurs, like the alarm buzzer 103C. In particular, the alarm display device 104C has a touch panel 104aC having a function of an operation panel. An operator can select the operation by touching the touch panel 104aC according to the instruction displayed on the alarm display device 104C.

Figure 31:
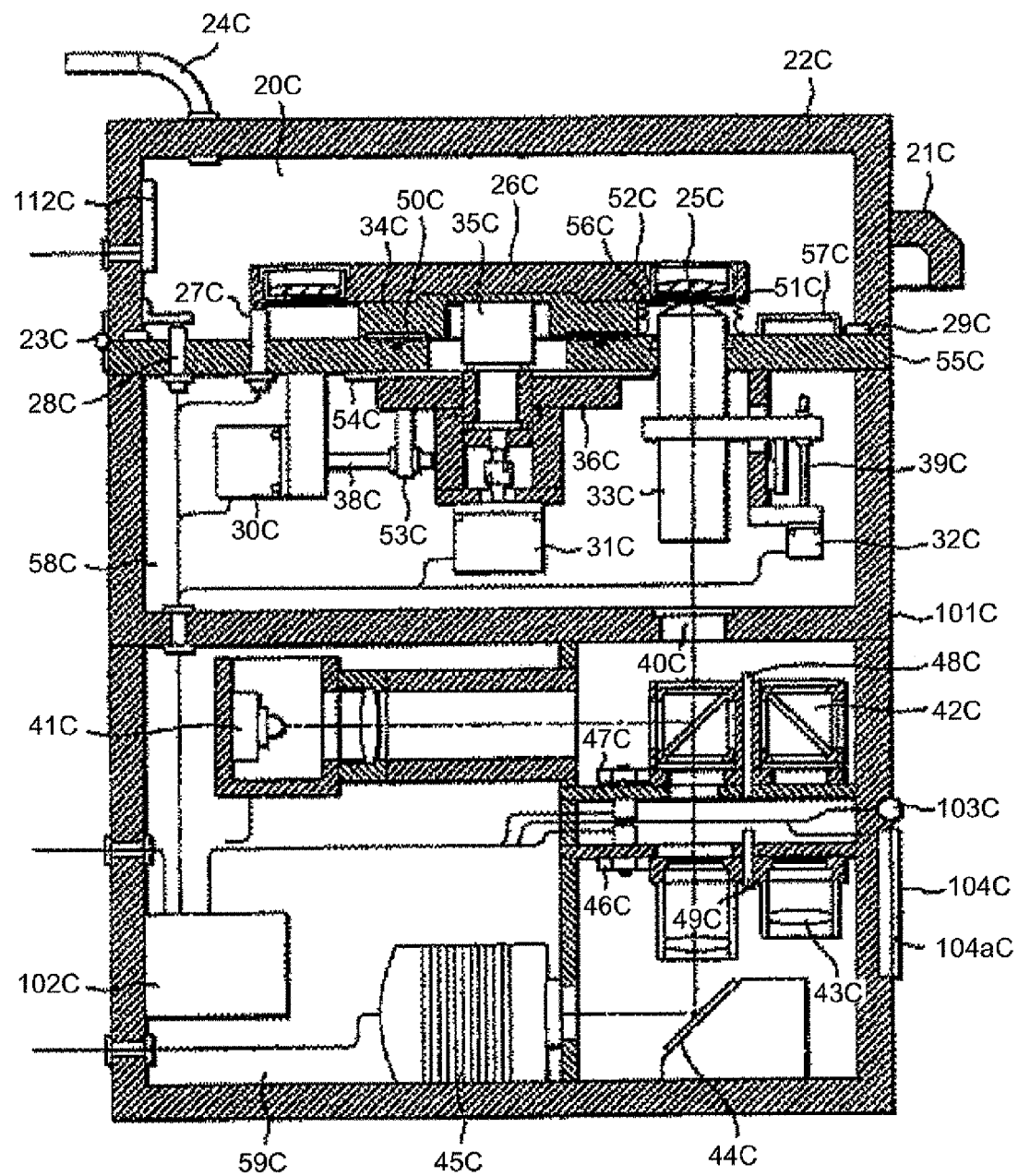
FIG. 31 is an internal structural view of an imaging apparatus according to the present invention in which a culture apparatus and a microscope apparatus, which can be applied to the present embodiment, are integrated.

A focus handle joystick 105C is connected to the controller 102C. The Z-axis direction (i.e., the direction in which a specimen is focused) of the microscope portion described below can be moved by the focus handle, and R-stage and θ-stage can be moved by the joystick. The θ-stage is an electric stage movable in the rotating direction about an axis, while the R-stage is an electric stage movable in the direction of one axis perpendicular to the central axis of the θ-stage. These are employed for downsizing the apparatus, but an ordinary XY stage may be employed. In particular, an R-stage motor 30C and θ-stage motor 31C shown in FIG. 31 are driven and controlled through the controller 102C based on the condition set by a later-described interval imaging condition setting unit of the apparatus in the present embodiment.

The main body 101C of the culture microscope has a temperature-control heater 112C in the incubator chamber, and a temperature controller 106C for controlling the heater 112C is provided.

The controller 102C and the temperature controller 106C are connected to a computer 109C (personal computer in FIG. 30) with an interface such as RS-232C, so that they can be controlled by the computer 109C. Various units (memory, operation circuit, display unit, input unit, etc.), which are necessary as the interface, are included.

A tank 107C that stores air mixture (in which temperature, moisture and concentration of carbon dioxide (carbon dioxide concentration) are controlled respectively to be, for example, 37° C., 95 to 100%, and 5%, wherein each numerical value is a normal value, and adjustable) supplied into the incubator chamber of the main body 101C of the culture microscope is mounted at the outside as illustrated. The air mixture can be supplied into the incubator chamber by opening or closing an electromagnetic valve 108C. In the present embodiment, air mixture is put into the tank 107C. However, the tank 107C is filled with only carbon dioxide, and an unillustrated water tank for keeping the temperature may be mounted into the incubator chamber. Further, the carbon dioxide can be supplied into the incubator chamber with the tank 107C not kept to be 37° C. The electromagnetic valve 108C may be controlled by the computer 109C.

The computer 109C is connected to a network 110C such as LAN, Internet, etc. The network 110C is connected to a remote computer 111C, whereby the remote computer 111C (personal computer in FIG. 30) can control the computer 109C through the network 110C. Accordingly, the time-lapse interval imaging executed by the main body 101C of the culture microscope can be monitored by the remote computer 111C or the computer 109C can function as a searchable database that can store a large amount of imaging data pieces. A user of the remote controller 111C may be a party concerned. However, it is preferable that an operation agreement is signed with an external specialized dealer doing a system operation in order to smoothly continue the use of the complex and wide variety of time-lapse imaging. The remote computer 111C may be a portable image receiver that mainly monitors at optional time, such as the time when a user leaves a room, the time when a user goes home, at the time of assertion, or during the vacation, so long as the remote computer 111C is at the place other than the site where the apparatus is installed (examination room, experiment room, etc.). A portable remote computer 111C can make an immediate operation, such as reading a desired image, or grasping abnormality with a buzzer, lamp, abnormal mark, etc. at the time of alarming. In any cases, in the remote computer 111C connected to the main body 101C with a communication unit, an access control is preferably made by a suitable authentication unit (e.g., password, ID of a person who is in charge, electronic key, biometrix (fingerprint, iris, vein, etc.)). It is further preferable that an access person to whom a suitable authentication is performed can make a remote control so as to change the interval imaging condition through the remote computer 111C. As described above, the remote computer 111C enables a monitoring or some operations even if a user does not go to the site where the apparatus is installed. Therefore, the present embodiment can provide a utilizing system excellent in greatly reducing a load of a user (e.g., man-hour, cost, moving time).

FIG. 31 is a view for showing an internal configuration of the main body 101C of the culture microscope according to the present embodiment. An incubator chamber 20C is hermetically closed from the outside by a lid 22C, and the temperature, moisture, and concentration of carbon dioxide ($CO_2$) of the culture environment in the incubator chamber 20C are kept to be constant or positively controlled. The air mixture is supplied from the tank 107C through an air pipe 24C. The unnecessary air is discharged from an unillustrated pipe. The lid 22C can be opened and closed by a handle 21C about a hinge 23C. When the lid 22C is opened, a lid open/close sensor 28C is operated so as to inform the open/close of the lid 22C of the controller 102C.

The heater 112C is provided in the incubator chamber 20C. When an unillustrated temperature sensor detects that the temperature in the incubator chamber 20C becomes not more than a predetermined temperature (e.g., 37° C.), the heater is automatically operated to keep the temperature. Although only one heater 112C is illustrated in FIG. 31, the heater may be mounted to the lid 22C or the whole base 55C so as to reduce the temperature variation in the incubator chamber 20C.

A circular tray 26C has plural specimen mounting holes 52C, into which plural specimen containers 25C can be mounted. The plural specimen containers 25C are held with respect to the circular tray 26C serving as a holding table of a transporting unit of the apparatus. In the present invention, even when plural specimen containers are held at the different positions of the plate-like holding table, like the circular tray, at the transporting unit, it can be referred to as "substrate storing plural specimen containers". The specimen container 25C can be taken out from the circular tray 26C in the upward direction. When the specimen container 25C is mounted to the circular tray 26C, the bottom surface of the specimen container 25C comes in contact with an annular projection 51C of the specimen mounting hole 52C of the circular tray 26C so as to prevent the specimen container 25C from falling off. The specimen container 25C can be positioned to the circular tray 26C. The bottom surface of the specimen container 25C is made of a transparent glass or resin, so that it can be observed from an objective lens 33C. Depending upon the material or surface shape of the specimen container 25C, an improved container is preferably used in which a central part or substantially all bottom surface of the specimen container 25C corresponding to the imaging field of view is recessed, and a transparent window, which has high light transmittance, is formed to be smooth, and is made of a glass or the like, is bonded to this portion.

A suitable specimen container lid 57C for covering the specimen container 25C may be covered for preventing the evaporation of water contents from the specimen. When the specimen container 25C is taken out from the incubator chamber 20C for the replacement of the medium, and then, put into the incubator chamber 20C with the specimen container 25C cooled, moisture might be adhered onto the specimen container lid 57C covering the specimen container 25C. A space for storing a spare specimen container lid 57C is formed in the incubator chamber 20C in order to replace the specimen container lid to which moisture is adhered, when moisture is adhered onto the specimen container lid 57C. The specimen container lid 57C placed in the storage space is not cooled because it is placed in the incubator chamber 20C during the replacement of the medium. The specimen container 25C is made of a bottom surface material and an upper surface material that are transparent and through which the specimen can be observed, such as a glass, and two members (member A and member B) having a large heat capacity, such as a metal. The bottom surface material and the member A are bonded to be fixed, while the upper surface material is bonded to the member B. The member A and the member B are detachable. With this structure, it can be prevented that the moisture is adhered onto the upper surface material and the bottom surface material.

The circular tray 26C can be detached from a rotation base 34C. When the circular tray 26C is detached, a circular tray detachment sensor 27C is operated so as to give to the controller 102C the information as to the detachment of the circular tray 26C. The circular tray detachment sensor 27C illustrated in FIG. 31 is a type of depressing a button. However, any sensors can be employed so long as it can detect the detachment of the circular tray 26C. The circular tray 26C, serving also as a specimen table, preferably has an admixture unit (not shown) for appropriately admixing a predetermined solution, such as a reagent, added into the specimen container 25C or replaced. The admixture unit can spread the liquid in the specific specimen container 25C completely in the container with pivot or vibration (ultrasonic vibration or shaking).

The rotation base 34C is attached to a θ rotation axis 35C so as to be capable of intermittently rotating or stopping the circular tray 26C in the predetermined rotating direction one tray by one tray with the rotation of the θ stage motor 31C. The rotation period made of the rotation and stop of the circular tray 26C is driven and controlled through the controller 102C based on the condition set by the interval imaging condition setting unit of a later-described apparatus according to the present embodiment. The modification of the rotation period is as follows. Specifically, the rotation period is set to be the period in which the circular tray 26C stops at the rotation distance longer or shorter by one tray from the number of all the specimen containers 25C on the same circumference of the circular tray 26C. With this, almost all the specimen containers 25C can make one rotation every time the circular tray intermittently moves, although the circular tray 26C seems to intermittently move one container by one container. During each of the circumferential movements, it can be monitored whether the medium state relating to the specimen container 25C is good or not.

A lead screw 38C is rotated by the R-stage motor 30C, so that a linear movement base 36C attached to a nut 53C is laterally moved. The linear movement base 36C includes a linear guide 54C, so that the linear movement base 36C can be moved in the linear direction. The 74 rotation axis 35C is mounted rotatably with respect to the linear movement base 36C. When the linear movement base 36C laterally moves, the rotation base 34C can also move laterally. Thus, a stage on which a specimen can be moved in R 74 coordinate system can be realized.

The base 55C separates the incubator chamber 20C and a motor chamber 58C. Bach section is closed so as to prevent high-humidity air in the incubator chamber 20C from entering the motor chamber 58C. A flat type sheet 50C is sandwiched between the rotation base 34C and the base 55C, so that they are slidable.

A bellows 56C is mounted to enclose the portion where the objective lens 33C is exposed in the incubator chamber 20C. The end face of the bellows 56C is fixed and closed to the leading end of the objective lens 33C and the base 55C for bonding. Thus, high-humidity air is prevented from entering in the motor chamber 58C from the gap between the base 55C and the objective lens 33C.

The objective lens 33C can be moved vertically by turning the lead screw 38C by a Z-stage motor 32C. The specimen is brought into focus by vertically moving the objective lens 33C. Even if the objective lens 33C vertically moves, the bellows 56C can be extended or contracted, because it is made of a soft resin such as rubber. Therefore, the sealed state can be maintained.

A microscope chamber 59C keeps a temperature to such a degree that the optical member does not expand due to the temperature change. An unillustrated heater is used for keeping the temperature.

The controller 102C is mounted to the microscope chamber 59C. Wirings to each unit are connected to the controller 102C. An LED illumination 41C is an illumination for observing fluorescence, and it illuminates a specimen through a fluorescent cube 42C, window 40C, and the objective lens 33C. The light from the specimen passes through the objective lens 33C, window 40C, and fluorescent cube 42C, passes through a magnification changing lens 43C, and is incident on a CCD camera 45C with the optical path bent at an angle of 90 degrees by a mirror 44C. The mirror 44C is mounted to secure the installation space of the CCD camera 45C. If there is the installation space of the CCD camera 45C, it is unnecessary to bend the optical path.

Instead of the LED illumination 41C, a mercury lamp not shown, optical fiber and the like can be used as a light source. In the case of the mercury lamp, a shutter is mounted to turn on/off the incident of light, because it cannot be turned on or off with high speed like the LED illumination 41C. This can be controlled by the controller 102C. Light may be incident on the CCD camera 45C without passing through the magnification changing lens 43C. Specifically, the magnification changing lens 43C may suitably be mounted to or removed from the optical path extending toward the CCD camera 45C from the objective lens 33C.

The fluorescent cube 42C is rotatable about an axis 48C so as to change to a fluorescent cube having a different wavelength. The fluorescent cube 42C can be electrically rotated through the drive of a cube turret motor 47C. This can be controlled by the controller 102C.

The magnification changing lens 43C is rotatable about an axis 49C so as to change to a lens having a different magnification. The magnification changing lens 43C can be electrically rotated through the drive of a lens turret motor 46C. This can be controlled by the controller 102C. The magnification changing lens 43C may be one zoom lens having a zoom function incorporated therein. Alternatively, it has a configuration that it is only replaced with a lens having a specification of a desired magnification according to need.

Figure 32:
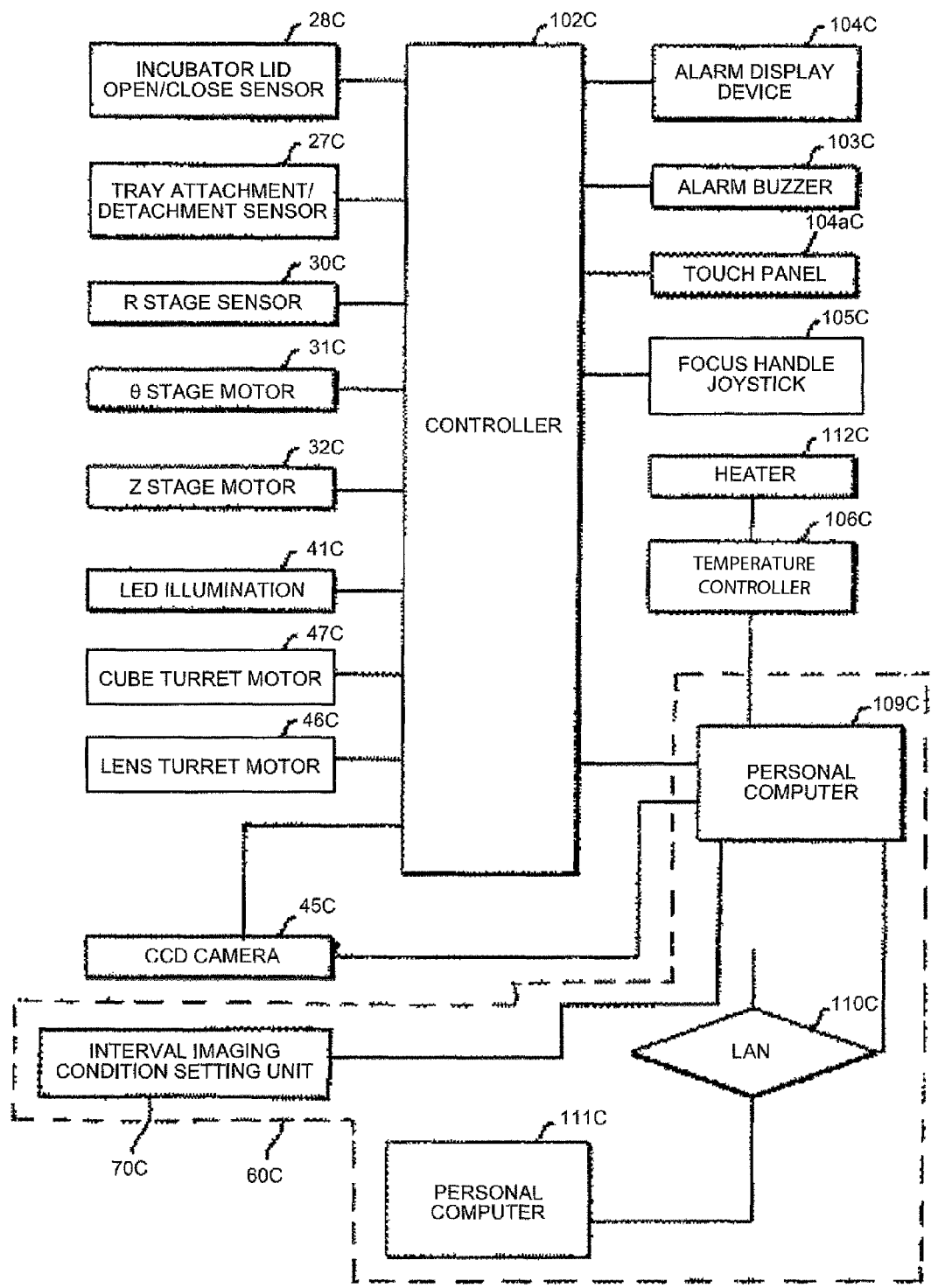
FIG. 32 is a block diagram of an electrically controllable unit in the high-throughput imaging apparatus.

FIG. 32 is a block diagram showing units, among the units illustrated in FIGS. 30 and 31, which are controllable by an electrical method. The explanation of the units explained at FIGS. 30 and 31 is omitted. Each unit is connected to the controller 102C, so that it can be controlled by an operator from a user interface of the computer (personal computer) 109C. A high-sensitive CCD camera employing a cooled CCD is used as the CCD camera 45C, and it is directly connected to the computer 109C. The heater 112C is connected to the computer 109C through the temperature controller 106C. If the controller 102C has the function of the temperature controller 106C, the heater 112C may be controlled via the controller 102C.

The characteristic configuration in FIG. 32 is that an interval imaging condition setting unit 70C for setting the imaging condition relating to the set specimen container 25C is connected to the controller 102C through the computer 109C in an external control system 60C that externally controls the units in the main body 101C of the apparatus. Another feature is that the controller 102C is connected to the CCD camera 45C, serving as the imaging unit, for driving and controlling the imaging operation of the CCD camera 45C. Therefore, the external control system 60C including various interfaces such as an input unit or a display unit involved with the computer 109C, the interval imaging condition setting unit 70C, the controller 102C serving as the internal control system, the CCD camera 45C serving as the imaging unit, and various motors 30C and 31C for the circular tray 26C that retains the specimen containers 25C can be cooperated with one another.

The setting content by the interval imaging condition setting unit 70C will be explained here. The interval imaging condition setting unit 70C provides an apparatus coping with various scenes described below.

Apparatus 1: A high-throughput imaging apparatus comprising an image acquiring unit that acquires an image of a specimen by imaging a biological specimen present at plural imaging regions, and a control unit that controls the image acquiring unit so as to perform a time-lapse interval imaging for every imaging regions, wherein the control unit has an interval imaging condition setting unit that sets a condition for the interval imaging for every imaging regions based on the imaging time required to obtain the image of the specimen and the number of the imaging regions.

Apparatus 2: The high-throughput imaging apparatus, according to the apparatus described in the Apparatus 1, wherein the condition of the interval imaging has a setting in which plural imaging regions are imaged by changing the plural imaging regions plural times.

Apparatus 3: The high-throughput imaging apparatus, according to the apparatus described in the Apparatus 2, wherein an image signal transmitted from the image acquiring unit is integrated for every imaging regions to form an image.

Apparatus 4: The high-throughput imaging apparatus, according to the apparatus described in the Apparatus 1, wherein the condition for the interval imaging includes a surplus time for performing different processes other than the time required for imaging.

Apparatus 5: The high-throughput imaging apparatus, according to the apparatus described in the Apparatus 4, including a light-shielding unit for performing a light-shield in order to keep the imaging regions to be an optical environment in which an imaging is possible by the image acquiring unit, and a processing unit for performing a process other than the imaging by the image acquiring unit by temporarily canceling the optical environment by the light-shielding unit.

Apparatus 6: The high-throughput imaging apparatus, according to the apparatus described in any one of the Apparatus 1 to Apparatus 5, including a moving unit that moves the image acquiring unit relative to the plural imaging regions.

Apparatus 7: The high-throughput imaging apparatus, according to the apparatus described in the Apparatus 6, wherein plural biological specimens are sequentially arranged along a circumference of a circular tray, and the circular tray can be rotated or stopped according to the imaging condition of the control unit.

Apparatus 8: The high-throughput imaging apparatus, according to the apparatus described in the Apparatus 7, wherein the rotation period of the circular tray is set such that the circular tray is stopped after it passes through the plural imaging regions.

Apparatus 9: The high-throughput imaging apparatus, according to the apparatus described in the Apparatus 8, wherein the rotation period of the circular tray includes a long-distance rotation mode by one rotation±one imaging region.

Apparatus 10: The high-throughput imaging apparatus, according to the apparatus described in the Apparatus 9, including a reference information acquiring unit that acquires different reference information relating to all the imaging regions on the circular tray during the long-distance rotation in the long-distance rotation mode.

Apparatus 11: The high-throughput imaging apparatus, according to the apparatus described in any one of the Apparatus 1 to Apparatus 4, wherein the image acquiring unit includes an imaging magnification changing unit that can change the imaging magnification in the imaging, wherein the interval imaging condition is set in accordance with the imaging magnification by the imaging magnification changing unit.

Apparatus 12: The high-throughput imaging apparatus, according to the apparatus described in any one of the Apparatus 1 to Apparatus 4, wherein the image acquiring unit includes a light-receiving device that receives an optical signal obtained from the imaging regions, wherein the interval imaging condition is set in accordance with the light-receiving ability of the light-receiving device.

Apparatus 13: A high-throughput imaging apparatus including an image acquiring unit that images a biological specimen, which is present at plural imaging regions, by an image information extracting unit, which extracts different image relating information, so as to obtain an image of the specimen, and a control unit that controls the image acquiring unit so as to perform a time-lapse interval imaging for every imaging regions, wherein the control unit has an interval imaging condition setting unit that sets a condition for the interval imaging for every imaging regions based on the imaging time required to obtain the image of the specimen and the kind of the image information extracting unit.

Apparatus 14: The high-throughput imaging apparatus, according to the apparatus described in the Apparatus 13, wherein the image information extracting unit extracts different image relating information simultaneously or continuously for the same imaging region.

Apparatus 15: The high-throughput imaging apparatus, according to the apparatus described in the Apparatus 14, including an image synthesizing unit that synthesizes the different image relating information, which is extracted by the image information extracting unit, as associated with the specimen on the imaging region.

Apparatus 16: The high-throughput imaging apparatus, according to the apparatus described in any one of the Apparatus 13 to Apparatus 15, wherein the image information extracting unit is a combination of two or more of transmitted light, fluorescence, bioluminescence, chemiluminescence, Raman spectroscopy, and infrared ray.

Apparatus 17: The high-throughput imaging apparatus, according to the apparatus described in any one of the Apparatus 1 to Apparatus 16, including a culture unit that continuously cultures a cell in the biological specimen, wherein the control unit sets the interval imaging condition in accordance with the imaging period during each culture period relating to the cell present in the plural imaging regions.

The information of the specimen relating to the specimen container 25C set to each of the specimen mounting holes 52C is stored in the memory incorporated in the computer 109C. The information of the specimen is read out when setting the time-lapse interval imaging condition so as to determine the imaging condition, whereby the controller 102C executes the imaging. The information relating to the determined imaging condition is reported to the computer 109C through the controller 102C, wherein it can be stored in the memory in the computer 109C as associated with the information of the specimen and can suitably be displayed on the user interface.

An individual ID of the specimen container 25C at the circular tray 26C is given to the user interface of the computer 109C. The computer 109C is programmed such that the corresponding imaging apparatus and the circular tray are operated through the ID. The input unit (optical mouse, keyboard, touch panel, electric pen, etc.) of the user interface promotes the computer 109C to set the imaging condition based on the information selected by the user for every ID.

In a series of steps indicated by the following each step, the apparatus is in a stand-by state for the observation, the GUI is displayed (S1), and the origin of the stage is set (S2). The specimen container that a user intends to observe can be input, and the apparatus is in a stand-by state for the input (S3). Thereafter, the user preferably depresses the arrow buttons at the "Stage/Rθ" and "Stage/Z" in the GUI, in order to search a cell that the user intends to perform a time-lapse image, while displaying the image of the cell in the specimen container 25C as a live image window. Then, the user selects the position by the input unit on the display screen. Specifically, in this example, any one of the aforesaid bright field image and luminescent image or both are firstly displayed, and then, a desired cell, cell population, tissue region, or specific region in the cell is designated. Preferably, the current imaging result or analyzing result can be displayed in an optional imaging period even during the time-lapse imaging. In order to realize this, it is preferable to perform a control in which the luminescent image obtained during the time-lapse imaging is analyzed one by one so as to quickly provide a result.

Subsequently, the apparatus is in a stand-by state for the observation condition relating to the selected observation position (S4), and the user inputs the desired observation condition (S5). The user inputs the observation condition (e.g., the wavelength of the feeble light according to the type of the reagent to be used or experiment condition, detection sensitivity, brightness in the bright field observation, etc.) in accordance with the demand in the same manner as described above. In the example of employing the fluorometry together as shown in FIG. 31, it is determined which one is used, LED-G (green) or LED-B (blue), or the brightness of the LED illumination 41C is determined. Alternatively, the user selects the fluorescent cube corresponding to the selected wavelength by the "Cube" button at the GUI, or determines the magnification changing lens corresponding to the button of the number at the "Lens" button. Further, the user determines the imaging condition of the camera as to the exposure time of the CCD camera or as to whether or not the AE is executed by the "Camera Control" button on the GUI, determines the name of the file into which the imaged image is stored by the "Image File Name" button, or sets all parameters required as the observation condition, such as the interval time of the time-lapse or the period of the experiment, by the "Time-Lapse" button. The interval time of the time-lapse is the sum of the time of the movement of the electric stage, imaging time, and control time for the first imaging of the multipoint in the case of executing the multipoint time-lapse (including the case of only one point), and the stand-by time immediately before the second imaging of the multipoint is started.

Then, when the input imaging condition is stored (S6), the computer resets the interval time of the time-lapse or resets the imaging time so as to be capable of completely image the imaging regions of a desired number, because the time-lapse interval imaging cannot correctly be performed when the sum of the movement time of the stage or the exposure time of the camera is longer than the interval time of the time-lapse. For example, the time, which is slightly longer than the sum of the movement time of the stage and the exposure time of the camera, is automatically calculated by clicking the automatic adjustment button on the GUI, and this time can be set as the interval time of the time-lapse. By setting the stand-by time to be approximately zero, the imaging can be switched to a time-lapse imaging having continuity. After the setting at the specific observation position is ended (S7), which means the preparation for the observation is ended, the apparatus is in the state in which the imaging can be started. When the storage of the input condition is canceled to re-input the condition, or the setting for another observation position is to be performed, the program returns to S3 to repeat the input.

As described above, according to the multipoint time-lapse shown in this example, each of the desired subjects to be observed can automatically and completely be observed under a high-throughput and appropriate imaging condition.

In the aforesaid example, the case in which the fluorescent microscope is employed together is explained. However, in the present embodiment, a luminescent image may exclusively be imaged. In this case, the irradiation optical system can be removed, because it is unnecessary to irradiate the excited light. A fluorescence-labeled cell or the like may be observed simultaneous with or separate from an image of a luminescence-labeled cell or the like. Examples of the luminescent marker include bioluminescence (or chemiluminescence) that emits a feeble light, which cannot be observed with naked eyes even by using a microscope.

Examples of the bioluminescence (or chemiluminescence) include a cell or tissue to which DNA, containing a luciferase gene as a reporter gene linked to the downstream of a promoter in a gene region of a specific interest, is transduced. When the cell or tissue in which the luciferase is expressed as the reporter is employed, the secular change of the transcription can be detected on real time by detecting the luciferase activity at the desired expression region.

A preferable embodiment is a cell or tissue derived from vertebrates in which the transduced luminescent gene is expressed so as to have a circadian rhythm in a peripheral tissue. The peripheral tissue includes a liver, lung, and skeletal muscle, but the invention is not limited thereto. It is reported that the peripheral tissues have a circadian rhythm with a phase difference of 7 to 12 hours. It is considered that the delay pattern of the circadian rhythm reflects a normal coordinate of a biorhythm of complex mammals constituted by many organs.

Accordingly, the information analyzed by the present embodiment can be said to be useful for elucidating a jet lag or a mechanism of sleep disorder, which are related to the circadian rhythm, and for developing a model of mammals that are used for the screening and test of a compound useful for a therapy of a disorder of circadian rhythm.

Various tests or screenings can be executed by using a transformer or transgenic mammals containing the DNA of the present embodiment in which a reporter gene is expressed. When the expression of the reporter gene in the tissues or cells is detected under various optional conditions, the effect of the stimulus or compound modifying the expression of the reporter gene can be evaluated, and can be screened. The stimulus includes a temperature, light, motion, and other shocks. There is no limitation on the used compound. The present embodiment is particularly applicable to a test or screening method of a compound, which modifies the expression derived from a promoter of a clock gene (e.g., Period 1) transduced to the transformer or transgenic mammals in the present embodiment, by using the transformer or transgenic mammals.

There is no limitation on the organs to be measured, and examples of the organs include a central nerve system (CNS) and peripheral nerve system (PNS) containing a subthalamic suprachiasmatic nucleus (SCN), and other peripheral tissues non-limitatively containing a liver, lung, or skeletal muscle. More specifically, the present embodiment is useful for evaluating a phase relationship and synchronized mechanism of the expression of the clock gene "Period 1" in the SCN or peripheral tissue. When a feeble light image for every different desired lapses of time is obtained continuously or intermittently by the luminescent microscope of the present embodiment, the pattern of the activity of the clock gene or the response pattern in the intracellular substance according to a drug or the like, for example, can exhaustively be evaluated based on the analysis data in which a light intensity of one or more same cells per time is exhaustively analyzed. Further, when an exhaustive evaluation is not performed to the cell, among the recognized cells, that does not exhibit a predetermined light intensity or light distribution, the cells that should not be analyzed are excluded to execute a correct evaluation. By calculating the total value or average of the light intensities of all cells that are subject to the image analysis, the evaluation of the whole analyzed cells can be executed, in addition to the evaluation of the individual cell. When two or more cells, which are subject to the image analysis, are classified into same or different cell group according to any one of the light intensity and the pattern of the light intensity or both, the activity of the clock gene can be evaluated for every analyzed pattern. Depending upon the situation, the activity or change of the activity of the clock gene can be checked in detail for each of the cells having different patterns. According to the present embodiment, an analysis can be carried out with a variety of combinations for variation parameters such as a waveform shape (e.g., amplitude length, width of period) or strength of the waveform (e.g., expression amount, activity speed) of the period of the expression pattern of the clock gene. The result of the analysis of the period of the expression pattern of the clock gene provides important information for a research use or industrial (medicine, agriculture, etc.) use such as diagnosis, therapy, growth (or biological development), whereby the present embodiment performs a great role.

The apparatus according to the present embodiment includes a holding unit that holds a biological specimen containing a large number of cells in a state in which an image thereof can be acquired; a feeble light image acquiring unit that accumulates optical data relating to an emission of a feeble light from the biological specimen so as to acquire image information that can be analyzed; and an image analyzing unit that recognizes the individual cell by morphologically analyzing the image information and exhaustively evaluates the light intensity of the feeble light relating to the recognized cell. The holding unit is configured such that a plate formed by integrating plural wells is held so as to be capable of being addressed, whereby the image analyzing unit can perform the evaluation between the plural wells in the same field of view or in a predetermined order. Therefore, the apparatus according to the present embodiment can compare or correlate the result of the evaluation of the activity by a different specimen, different drug or the like. In this case, the holding unit may be configured such that plural independent containers are held so as to be capable of being addressed. By virtue of this configuration, the field of view is not limited to the field of view of the feeble light imaging unit, and the image analyzing unit can perform the evaluation for a large number of containers. The apparatus of the present embodiment may include a control unit that performs the evaluation according to the time when the image information is acquired, whereby the apparatus can carry out a variety of time-analyses such as the analysis for the same cell according to the lapse of time, or comparison and analysis of cells (same or different cells) at different times when a specific activity is shown. The apparatus of the present embodiment may include a display unit that displays the result of the analysis by the image analyzing unit as associated with the image information. By virtue of this configuration, the image corresponding to the result of the analysis, which a user wishes to see as an image, of the results of the analysis, can be displayed. When the display unit has a configuration for displaying a moving image of the desired image information, the change in the activity of one or more desired cells can be observed with a real-time image by the apparatus of the present embodiment. It is preferable that, in the display of the moving image, the feeble light images of the same cell at different times are superimposed by an image processing so as to enhance a sense of reality. In the display of the moving image, plural time-series images of the same cell are displayed in parallel (or only some portions are shifted) with a frame feed, so as to observe all images for every time.

In the present invention, an illumination light for obtaining a transmitted light image (bright field image) may be replaced by an excited light for inducing a fluorescent image. In this case, the step of performing an imaging of the fluorescent image induced after the illumination of the excited light as the illumination light may be explained as the imaging of the illumination image.

The present embodiment includes embodiments and application examples involved with any one of the feeble light imaging method and imaging apparatus or both according to the present embodiment and an embodiment of software for the imaging apparatus described below.

Aspect 1: A biological examination device provided with the aforesaid imaging apparatus (e.g., endoscope, CT scanning measurement device).

Aspect 2: An analyzing apparatus provided with the aforesaid imaging apparatus (e.g., luminometer, cytometer).

Aspect 3: A biochip manufacturing apparatus provided with the aforesaid imaging apparatus.

Aspect 4: An analyzing service of image data according to the aforesaid feeble light imaging method.

Aspect 5: A management system of image information according to the aforesaid feeble light imaging method.

Aspect 6: A feeble light multi-imaging method in which, in the aforesaid feeble light imaging method, two imaging cameras connected to an optical filter, which corresponds to two (or three or more) wavelengths, are arranged, light beam from a specimen is divided into two (or n that is three or more) by a light separating device, and two types (or three or more types) of feeble light data pieces are accumulated simultaneously by each camera so as to acquire feeble light images for each of the wavelengths that are perfectly synchronized.

Aspect 7: A feeble light multi-imaging method in which, in the aforesaid feeble light imaging method, light beam from a specimen is divided into two (or n that is three or more) by a light separating device, which corresponds to two (or three or more) wavelengths, each of the light beams for every wavelength after the separation is imaged on an imaging area for every wavelength set on the same (or different) imaging devices (e.g., CCD), and two (or three or more types) of feeble light data pieces in all imaging areas are simultaneously accumulated so as to acquire feeble light images for each of the wavelengths that are perfectly synchronized.

Aspect 8: An imaging apparatus for executing the feeble light multi-imaging method described in the Aspect 6 or the Aspect 7.

Software 1: Software for a high-throughput imaging apparatus including a program for causing the control unit and the image acquiring unit to function so as to execute an interval imaging under a set interval imaging condition, in the apparatus described in the Apparatuses 1 to 17.

Software 2: Software for executing the apparatus, service or system described in the Aspects 1 to 8.

It can be construed that the invention include the invention described in Additional Items described below.

Additional Item 1B: An imaging method of a biological specimen in which an optical condition determined by a high numerical aperture (NA) and a magnification and a method or an apparatus to be applied are cooperated so as to optimize the cooperation with an imaging of a feeble light.

Additional Item 2B: The imaging method of a biological specimen, in the imaging method of a biological specimen described in Additional Item 1B, wherein the imaging includes a step of setting an interval condition so as to obtain plural images of the biological specimen at different times.

Additional Item 3B: An imaging apparatus using the imaging method of a biological specimen described in Additional Item 1B or 2B.

Additional Item 4B: The imaging apparatus, in the imaging apparatus described in Additional Item 3B, which is controlled to cooperate with software for analyzing a cell emitting a feeble light.

Additional Item 5B: The imaging method of a biological specimen, in the imaging method of a biological specimen described in Additional Item 1B or 2B, including suitably improvement or modification.

Additional Item 6B: The imaging apparatus, in the imaging apparatus described in Additional Item 3B or 4B, including suitably improvement or modification.

[I] An analyzing method of analyzing a feeble light image according to one aspect of the present invention includes, when analyzing an image of a biological specimen emitting a feeble light, a step of determining at least one reference position relating to a target region to be analyzed of the biological specimen by using an electromagnetic energy that is different in type from the feeble light to the target region, a step of determining a focal position for the feeble light corresponding to the target region with respect to the reference position, a step of focusing to the determined focal position so as to execute the formation of an image with the feeble light, a step of extracting necessary numerical values of a measurement parameter from the feeble light image, and a step of evaluating the target region based on the extracted parameter values. In the analyzing method of analyzing a feeble light image according to another aspect of the present invention, an acquisition of a reference image by the electromagnetic energy is included in the step of determining the reference position. In the analyzing method of analyzing a feeble light image according to still another aspect of the present invention, an image is acquired with respect to a specimen region including the target region in the acquisition of the reference image. In the analyzing method of analyzing a feeble light image according to still another aspect of the present invention, the electromagnetic energy is any one of visible light, near-infrared rays, ultrasonic wave, and a magnetic line which give less damages to a living body.

One aspect of the present invention is a analyzing method of analyzing a feeble light image in which irradiation light, which is easy to be visible, is irradiated to a biological specimen that emits a feeble light, which is difficult to be visible directly, so as to make the biological specimen visible, a position corresponding to a distance necessary for making an image with the feeble light emitted from a target region to be analyzed of the biological specimen is determined as a focal position for a feeble light by an objective lens with any one of a focal position at a near point of the objective lens and a focal position at a far point of the objective lens receiving light from the reference image provided by the biological specimen that is made visible or both defined as a reference position, with respect to the reference image, the feeble light is stored until a necessary image is formed by focusing the objective lens onto the determined focal position for a feeble light so as to form a feeble light image of the biological specimen, and the presence or absence of the feeble light or a light intensity at the target region is evaluated from the formed feeble light image. In the analyzing method of analyzing a feeble light image according to another aspect of the present invention, it is defined that direct visualization is difficult when the exposure time for forming an optical image is 10 seconds or more. In the analyzing method of analyzing a feeble light image according to still another aspect of the present invention, an image signal based on the irradiation light is transmitted light or fluorescence.

As the analyzing method of analyzing a feeble light image according to still another aspect of the present invention, in the analyzing method of analyzing the feeble light image described above, the determination of the focal position for the feeble light is preferably executed for every observed region of the biological specimen. Further, in the analyzing method of analyzing a feeble light image according to still another aspect of the present invention, the reference position and the focal position are determined on the same beam path of the objective lens.

As the analyzing method of analyzing a feeble light image according to still another aspect of the present invention, in the analyzing method of analyzing the feeble light image described above, it is preferable that plural feeble light images are stored by executing the acquisition of the feeble light image at plural times according to the examination items, the observed target regions in the stored plural feeble light images are collated, and the collated plural feeble light images are compared every period.

As the analyzing method of analyzing a feeble light image according to still another aspect of the present invention, in the analyzing method of analyzing the feeble light image described above, it is preferable that the acquisition of any one of the reference image and the feeble light image or both is executed again when the focal positions of the reference image and the feeble light image are out of the set distance range as a result of the comparison of the focal positions of the reference image and the feeble light image. In the analyzing method of analyzing a feeble light image according to still another aspect of the present invention, the acquisition of the measurement parameter from the reference image is included in the evaluation of the feeble light image, wherein the evaluation of the feeble light parameter is performed as associated with the measurement data from the reference image. As the modification, the analyzing method of analyzing a feeble light image according to still another aspect of the present invention may be configured to evaluate the feeble light image as associated with outline information of the target region in the reference image so as to extract the evaluation capability relating to the feeble light to the fullest by combining image processings using two or more of different images.

In the analyzing method of analyzing a feeble light image according to still another aspect of the present invention, the intensity of the feeble light per area corresponding to the outline of the target region is evaluated. The analyzing method of analyzing a feeble light image according to still another aspect of the present invention may be configured such that the position or distribution of the feeble light in the outline of the target region is determined in the evaluation.

The analyzing method of analyzing a feeble light image according to still another aspect of the present invention is such that the biological specimen is individually stored in plural storing sections, and the determination of the reference position is executed for each storing section. Examples of the storing sections include a microplate in which wells that are plural storing sections are integrally formed. The case in which plural storing sections are separately mounted, and each of them is conveyed as needed is included. The present invention provides an analyzing method suitable for evaluating a feeble light from a biological specimen stored in the plural storing sections. When the analyzing method of analyzing the feeble light described above in which the feeble light image is acquired in a wide angle of view including plural storing sections is employed as the analyzing method of analyzing the feeble light image according to still another aspect of the present invention, it becomes unnecessary to acquire the feeble light image for each storing section, and further, the evaluation can be made without missing the change in the feeble light for each storing section. In the analyzing method of analyzing the feeble light image according to still another aspect of the present invention, the measurement parameter from the target region is acquired by any one of optically magnifying and electrically magnifying the feeble light image or both.

In the analyzing method of analyzing a feeble light image according to still another aspect of the present invention described above, the biological specimen is a living cell or tissue, which makes a cytological or genetical analysis possible, thus preferable. In the analyzing method of analyzing a feeble light image according to still another aspect of the present invention, the feeble light is a luminescence involved with the expression of a bioluminescent protein, which makes the analysis of an expression of a gene for every cell possible, thus preferable.

The present invention also relates to a biological specimen imaging method. One aspect of the present invention is the biological specimen imaging method in which a biological specimen which is stored in a storing section of a substrate having plural storing sections and emitting a feeble light is imaged through an objective lens. The biological specimen imaging method according to one aspect of the present invention includes moving any one of the substrate and the objective lens or both until the desired storing section falls within the field of view of the objective lens, measuring any one of a focal position at a near point and the focal position at a far point of the objective lens or both, determining the focal position of the objective lens focused on an observed target region in the biological specimen stored in the desired storing section based on the measured focal position, adjusting the focal position of the objective lens to the determined focal position, and imaging the biological specimen through the objective lens.

Another aspect of the present invention is the biological specimen imaging method, wherein, when any one of the substrate and the objective lens or both are moved until the desired storing section falls within the field of view of the objective lens, the position of any one of the substrate and the objective lens or both at the moving destination is measured, and moving destination positional information relating to the measured position at the moving destination is stored as associated with storing section identifying information for identifying the desired storing section.

The present invention also relates to a biological specimen imaging method. One aspect of the present invention is the biological specimen imaging method in which a biological specimen which is stored in a storing section of a substrate having plural storing sections and emitting a feeble light is imaged through an objective lens. The biological specimen imaging method according to one aspect of the present invention includes a moving step of moving any one of the substrate and objective lens or both until the desired storing section falls within the field of view of the objective lens, a light irradiating step of irradiating light to the biological specimen, a focal position changing step of changing the focal position of the objective lens, a focal position measuring step of measuring the changed focal position at the focal position changing step, a light-irradiated specimen imaging step of imaging the biological specimen to which the light is irradiated at the light irradiating step at the changed focal position at the focal position changing step, a feature data calculating step of calculating feature data which characterizes the imaged image based on the imaged image at the light-irradiated specimen imaging step, an executing step of repeatedly executing the focal position changing step, the focal position measuring step, the light-irradiated specimen imaging step, and the feature data calculating step, a focal position selecting step of selecting at least one focal position from the plural focal positions stored by the repeated execution at the executing step based on the plural feature data pieces stored by the repeated execution, a focal position determining step of determining the focal position of the objective lens focused to the observed target region in the biological specimen stored in the desired storing section based on the focal position selected at the focal position selecting step, a focus adjusting step of adjusting the focal position of the objective lens to the determined focal position at the focal position determining step, and a luminescent image acquiring step of imaging the biological specimen through the objective lens so as to acquire the luminescent image of the biological specimen.

Another aspect of the present invention is the biological specimen imaging method, wherein, at the moving step, any one of the substrate and objective lens or both are moved until the desired storing section falls within the field of view of the objective lens, the position of any one of the substrate and the objective lens or both at the moving destination is measured, and moving destination positional information relating to the measured position at the moving destination is stored as associated with storing section identifying information for identifying the desired storing section.

The present invention also relates to a biological specimen imaging apparatus. One aspect of the present invention is the biological specimen imaging apparatus that images a biological specimen which is stored in a storing section of a substrate having plural storing sections and emitting a feeble light through an objective lens. The biological specimen imaging apparatus according to one aspect of the present invention includes a mover that moves any one of the substrate and objective lens or both until the desired storing section falls within the field of view of the objective lens, a light irradiator that irradiates light to the biological specimen, a focal position changer that changes the focal position of the objective lens, a focal position measurer that measures the focal position of the objective lens, a specimen imager that images the biological specimen, a feature data calculator that calculates feature data which characterizes the imaged image based on the image imaged by the specimen imager, a controller that controls the focal position changer, the focal position measurer, the specimen imager, and the feature data calculator so as to repeatedly execute the focal position changer, the focal position measurer, the specimen imager, and the feature data calculator, a focal position selector that selects at least one focal position from the plural focal positions stored by the repeated execution by the controller based on the plural feature data pieces stored by the repeated execution, and a focal position determining unit that determines the focal position of the objective lens focused to the observed target region in the biological specimen stored in the desired storing section based on the selected focal position by the focal position selector.

The biological specimen imaging apparatus according to another aspect of the present invention further includes a moving destination position measurer that measures the position of any one of the substrate and the objective lens or both at the moving destination when any one of the substrate and the objective lens or both are moved by the mover, a storage unit that stores the moving destination positional information relating to the position at the moving destination measured by the moving destination position measurer as associated with storing section identifying information for identifying the desired storing section.

According to the analyzing method of analyzing a feeble light image of the present invention, a biological specimen can quickly and correctly be analyzed. Further, according to the biological specimen imaging method and the biological specimen imaging apparatus of the present invention, a biological specimen stored in each storing section provided to a substrate (e.g., each well of a microplate) can quickly and correctly be imaged. According to the biological specimen imaging method and the biological specimen imaging apparatus of the present invention, when any one of the substrate and the objective lens or both are moved until the desired storing section falls within the field of view of the objective lens, the position of any one of the substrate and the objective lens or both at the moving destination is measured, and moving destination positional information relating to the measured position at the moving destination is stored as associated with storing section identifying information for identifying the desired storing section. Therefore, any one of the substrate and the objective lens or both can be moved until the desired storing section falls within the field of view of the objective lens based on the moving destination positional information and the storing section identifying information.

[II] In an imaging method of a biological specimen according to one aspect of the present invention, an optical condition determined by a high numerical aperture (NA) and a magnification and a method or an apparatus to be applied are cooperated so as to optimize the cooperation with an imaging of a feeble light. It is preferable that the imaging includes a step of setting an interval condition so as to obtain plural images of the biological specimen at different times. In the aforesaid method, at least a cell emitting a feeble light is included, whereby an analysis of an image including the cell is possible. One aspect of the present invention is an imaging apparatus employing the method. This apparatus preferably cooperates with software for analyzing a cell emitting a feeble light.

In a luminescent specimen imaging method embodying the imaging apparatus and imaging method described above, in the luminescent specimen imaging method for imaging a luminescent specimen, an objective lens in which the square of $(NA \div \beta)$ represented by a numerical aperture (NA) and a projection magnification ($\beta$) is 0.01 or more, and preferably 0.039 or more, is used. One aspect of the present invention can be embodied as the luminescent cell imaging method, wherein, in the luminescent cell imaging method for imaging a luminescent cell to which a luciferase gene is transduced, an objective lens in which the square of $(NA \div \beta)$ represented by a numerical aperture (NA) and a projection magnification ($\beta$) is 0.01 or more, and preferably 0.039 or more, is used.

One aspect of the present invention relates to an objective lens. The objective lens according to one aspect of the present invention is used for the luminescent specimen imaging method for imaging a luminescent specimen, wherein the square of $(NA \div \beta)$ represented by a numerical aperture (NA) and a projection magnification ($\beta$) is 0.01 or more, and preferably 0.039 or more.

One aspect of the present invention relates to an objective lens. The objective lens according to one aspect of the present invention is used for the luminescent cell imaging method for imaging a luminescent cell to which luciferase gene is transduced, wherein the square of $(NA \div \beta)$ represented by a numerical aperture (NA) and a projection magnification ($\beta$) is 0.01 or more, and preferably 0.039 or more.

One aspect of the present invention relates to an objective lens. The objective lens according to one aspect of the present invention is used for the luminescent specimen imaging method for imaging a luminescent specimen, wherein the square of (NA÷β) represented by a numerical aperture (NA) and a projection magnification (β) is written on any one of the objective lens and a packaging container that packages the objective lens or both.

In a luminescent specimen imaging method embodying the imaging apparatus and imaging method according to the present invention, an objective lens in which the square of (NA÷β) represented by a numerical aperture (NA) and a projection magnification (β) is 0.01 or more, and preferably 0.039 or more, is used. Therefore, the present invention provides an effect that a clear image can be taken in a short exposure time or on a real time, even in the case of a luminescent specimen having a small light emission amount (e.g., luminescent protein (e.g., luminescent protein expressed from the transduced gene (e.g., luciferase gene)), luminescent cell, luminescent cell population, luminescent tissue material, luminescent individual (e.g., animal or organ)). In a luminescent cell imaging method embodying the imaging apparatus and imaging method according to the present invention, an objective lens in which the square of (NA÷β) represented by a numerical aperture (NA) and a projection magnification (β) is 0.01 or more, and preferably 0.039 or more, is used. The present invention provides an effect that a clear image can be taken in a short exposure time or on a real time with a luminescent cell to which a luciferase gene is transduced defined as an imaging subject.

An objective lens is used in a luminescent specimen imaging method and luminescent cell imaging method embodying the imaging apparatus and imaging method according to the present invention, wherein the square of (NA÷β) represented by a numerical aperture (NA) and a projection magnification (β) is 0.01 or more, and preferably 0.039 or more. The present invention provides an effect that a clear image can be taken in a short exposure time or on a real time, even in the case of a luminescent specimen having a small light emission amount (e.g., luminescent protein (e.g., luminescent protein expressed from the transduced gene (e.g., luciferase gene)), luminescent cell, luminescent cell population, luminescent tissue material, luminescent individual (e.g., animal or organ)). Specifically, the present invention provides an effect that a clear image can be taken in a short exposure time or on a real time with a luminescent cell to which a luciferase gene is transduced defined as an imaging subject.

The objective lens used in the luminescent specimen imaging method and the luminescent cell imaging method, which embody the imaging apparatus and the imaging method of the present invention, has a large numerical aperture and small magnification, compared to a conventional objective lens. Therefore, a specimen can be imaged in a wide range with an excellent resolution by using the objective lens. Accordingly, a moving luminescent specimen or a luminescent specimen distributed in a wide range can be defined as an imaging subject. The square (e.g., 0.01 or more, preferably 0.039 or more) of (NA÷β) represented by a numerical aperture (NA) and a projection magnification (β) is written on any one of the objective lens and the packaging container (package) that packages the objective lens or both. Therefore, a person who observes a luminescent image can easily select an objective lens suitable for imaging the luminescent specimen in a short exposure time or on a real time by confirming the written square of (NA÷β).

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A biological specimen imaging method in which a biological specimen, which is stored in a storing section of a substrate having plural storing sections, emits a feeble light in an observed target region that is imaged through an objective lens, the method comprising:
    moving any one of the substrate and the objective lens or both until the desired storing section falls within the field of view of the objective lens,
    measuring any one of a focal position at a near point and the focal position at a far point of the objective lens or both under irradiated light, wherein the focal position at the near point is at the portion of the biological specimen closest to the objective lens and the focal position at the far point is at the portion of the biological specimen furthest from the objective lens;
    determining a central position between the focal position at the near point and the focal position at the far point as the focal position of the objective lens focused on the observed target region in the biological specimen stored in the desired storing section based on the measured focal position, and
    adjusting the focal position of the objective lens to the determined focal position so as to image the biological specimen through the objective lens.

2. The biological specimen imaging method according to claim 1, wherein, when any one of the substrate and the objective lens or both are moved until the desired storing section falls within the field of view of the objective lens, the position of any one of the substrate and the objective lens or both at the moving destination is measured, and moving destination positional information relating to the measured position at the moving destination is stored as associated with storing section identifying information for identifying the desired storing section.

3. A biological specimen imaging method in which a biological specimen which is stored in a storing section of a substrate having plural storing sections and emits a feeble light in an observed target region that is imaged through an objective lens, the method comprising:
    a moving step of moving any one of the substrate and objective lens or both until the desired storing section falls within the field of view of the objective lens;
    a light irradiating step of irradiating light to the biological specimen;
    a focal position changing step of changing the focal position of the objective lens;
    a focal position measuring step of measuring the changed focal position at the focal position changing step;
    a light-irradiated specimen imaging step of imaging the biological specimen to which the light is irradiated at the light irradiating step at the changed focal position at the focal position changing step;
    a feature data calculating step of calculating feature data which characterizes the imaged image based on the imaged image at the light-irradiated specimen imaging step;
    an executing step of repeatedly executing the focal position changing step, the focal position measuring step, the light-irradiated specimen imaging step, and the feature data calculating step;
    a focal position selecting step of selecting at least one focal position from the plural focal positions stored by the repeated execution at the executing step based on the plural feature data pieces stored by the repeated execution;

a focal position determining step of determining a central position between the focal position at a near point and the focal position at a far point as the focal position of the objective lens focused to the observed target region in the biological specimen stored in the desired storing section based on the focal position selected at the focal position selecting step, wherein the focal position at the near point is at the portion of the biological specimen closest to the objective lens and the focal position at the far point is at the portion of the biological specimen furthest from the objective lens;

a focus adjusting step of adjusting the focal position of the objective lens to the determined focal position at the focal position determining step; and a luminescent image acquiring step of imaging the biological specimen through the objective lens so as to acquire the luminescent image of the biological specimen.

4. The biological specimen imaging method according to claim 3, wherein, at the moving step, any one of the substrate and objective lens or both are moved until the desired storing section falls within the field of view of the objective lens, the position of any one of the substrate and the objective lens or both at the moving destination is measured, and moving destination positional information relating to the measured position at the moving destination is stored as associated with storing section identifying information for identifying the desired storing section.

5. A biological specimen imaging apparatus that images a biological specimen which is stored in a storing section of a substrate having plural storing sections and emits a feeble light in an observed target region through an objective lens, the apparatus comprising:

a mover that moves any one of the substrate and objective lens or both until the desired storing section falls within the field of view of the objective lens;

a light irradiator that irradiates light to the biological specimen;

a focal position changer that changes the focal position of the objective lens;

a focal position measurer that measures the focal position of the objective lens under irradiated light;

a specimen imager that images the biological specimen;

a feature data calculator that calculates feature data which characterizes the imaged image based on the image imaged by the specimen imager;

a controller that controls the focal position changer, the focal position measurer, the specimen imager, and the feature data calculator so as to repeatedly execute the focal position changer, the focal position measurer, the specimen imager, and the feature data calculator;

a focal position selector that selects at least one focal position from the plural focal positions stored by the repeated execution by the controller based on the plural feature data pieces stored by the repeated execution; and a focal position determining unit that determines a central position between the focal position at a near point and the focal position at a far point as the focal position of the objective lens focused to the observed target region in the biological specimen stored in the desired storing section based on the selected focal position by the focal position selector, wherein the focal position at the near point is at the portion of the biological specimen closest to the objective lens and the focal position at the far point is at the portion of the biological specimen furthest from the objective lens.

6. The biological specimen imaging apparatus according to claim 5, further comprising:

a moving destination position measurer that measures the position of any one of the substrate and the objective lens or both at the moving destination when any one of the substrate and the objective lens or both are moved by the mover; and a storage unit that stores the moving destination positional information relating to the position at the moving destination measured by the moving destination position measurer as associated with storing section identifying information for identifying the desired storing section.

\* \* \* \* \*